United States Patent [19]

Johnson

[11] 4,222,274
[45] Sep. 16, 1980

[54] ULTRASOUND IMAGING APPARATUS AND METHOD

[76] Inventor: Steven A. Johnson, 136 N. First West, Preston, Id. 83772

[21] Appl. No.: 942,740

[22] Filed: Sep. 15, 1978

[51] Int. Cl.[2] .......................................... G01N 29/00
[52] U.S. Cl. ...................................... 73/607; 73/626; 128/660
[58] Field of Search ................ 73/596, 599, 600, 602, 73/606, 607, 609, 618, 620, 621, 622, 624, 625, 626, 627, 628, 633, 634, 640; 128/660; 340/1 R, 3 R, 5 MP; 367/7, 13, 103, 104, 105, 138

[56] References Cited

U.S. PATENT DOCUMENTS

| | | | |
|---|---|---|---|
| 3,805,596 | 4/1974 | Klahr | 73/602 |
| 3,885,224 | 5/1975 | Klahr | 73/602 |
| 4,047,520 | 9/1977 | Soldner et al. | 73/620 |
| 4,074,564 | 2/1978 | Andersen | 73/596 |
| 4,075,883 | 2/1978 | Glover | 73/602 |
| 4,100,916 | 7/1978 | King | 128/660 |
| 4,105,018 | 8/1978 | Greenleaf et al. | 128/660 |
| 4,109,642 | 8/1978 | Reid et al. | 73/622 |
| 4,109,644 | 8/1978 | Kojima | 128/660 |
| 4,120,291 | 10/1978 | Paton et al. | 73/618 |

OTHER PUBLICATIONS

P. D. Coral et al., "A Digital Synthetic Focus Acoustic Imaging System", Acoustical Imaging, 8th Int'l. Conference, Jun. 1978, pp. 1-16.

*Primary Examiner*—Stephen A. Kreitman

[57] ABSTRACT

A ring of transmitter and receiver transducer arrays circumbscribes an object to be scanned. Semicircular wave fronts of ultrasound energy are propagated from different points around the ring of transducers by triggering the transmitter arrays in sequence. The reflected and transmitted ultrasound energy picked up by the receiver arrays is then electronically analyzed and a synthetically focused image corresponding to the scanned object is reconstructed on a display screen. Surprisingly high quality resolution for the reconstructed images is achieved by carefully controlling the type of waveform from which the displayed image is reconstructed. In one embodiment of the invention, the signals received by the receiver arrays are processed by a waveshaping circuit to achieve the desired waveform. In a second embodiment of the invention, the desired waveform is generated by a waveform generator circuit and transmitted by the transmitter arrays. The quality of resolution for the reconstructed image of reflection is further improved by obtaining, through a computer aided ray tracing technique, the connecting rays between each point in the object and each transmitter and receiver array element. Data sampling times for each point in the reconstructed image are then corrected for refraction by computer aided integration of the object's refractive index along each connecting ray. Correction of the sampled data for amplitude attenuation is similarly obtained by computer aided integration of the object's linear attenuation coefficient along the connecting rays.

41 Claims, 22 Drawing Figures

ULTRASOUND IMAGING APPARATUS AND METHOD

BACKGROUND

1. Field of the Invention

The present invention relates to an apparatus and method for ultrasound imaging of biological tissue according to the impulse-echo technique, and more particularly the present invention relates to a novel and unobvious apparatus and method for reconstructing images of reflection in biological tissue or other media using synthetically focused ultrasound energy.

2. The Prior Art

It has long been known that ultrasonic or acoustic waves in the frequency range of 15,000 cycles per second and higher can be propagated through many solids and liquids. Ultrasound waves are usually considered to be those in the frequency range from approximately 50,000 cycles per second to 10,000,000 cycles per second and higher. Ultrasound energy waves may be partially reflected and partially transmitted at any interface between two media of different density. The product of material density and sonic wave velocity is known as the acoustic impedance, and the amount of reflection which occurs at the interface between two media is dependent upon the amount of change in the acoustic impedance between one medium as opposed to the other medium.

These principles have long been used for imaging reflecting bodies within an ultrasound propagation medium. For example, the organs of a human body as well as bones and sinew act as reflecting bodies within the soft tissue of the body. Likewise, any foreign inclusion will act as a reflecting body. Thus, noninvasive internal examination and medical diagnosis of the human body by ultrasound imaging has long been known in the art. For example, piston type transducers have been used for over 30 years to image some parts of the body.

The inherent advantages of noninvasive medical diagnosis by ultrasound imaging are readily apparent. Unlike exploratory surgery or x-rays, ultrasound imaging permits internal examination of an organ without damaging the surrounding tissue and organs of the body and with much less trauma to the patient.

However, despite the many advantages which may be derived from noninvasive examination by ultrasound imaging, in the past ultrasound imaging has been somewhat limited in its application. One of the primary problems encountered in this regard is the difficulty in providing reflection images of high quality resolution. These images may often be blurred or distorted to some degree, making accurate diagnosis difficult, particularly with respect to very small objects in the body.

Thus, recently much attention has been directed to improving the quality of resolution of ultrasound images. For example, linear phased (or so-called "beam steering") transducer arrays have demonstrated improved depth of focus and time resolution. See, for example, Somer, J. C., W. A. Oosterbaan and H. J. Freund: *Ultrasonic Tomographic Imaging of the Brain with an Electronic Sector Scanning System*, Proceedings of the 1973 IEEE Ultrasonic Symposium, Nov. 5–7, 1973; and Thurstone, F. L., and O. T. Van Ramm: *A New Ultrasound Imaging System Employing Two-Dimensional Electronic Beam Steering*, Heart Bulletin, Volume 4, p. 51 (1973). It has also been demonstrated that nonstraight line transducer array configurations may be employed to enhance resolution quality in ultrasound images by increasing the aperture for transmitting and receiving ultrasound energy. See, for example, Maginness, M. G., J. D. Plummer and J. D. Meindl: *A Cardiac Dynamics Visualization System*, Proceedings of the 1973 IEEE Ultrasonic Symposium, Nov. 5–7, 1973; and Green, P. S., L. F. Schaefer, E. D. Jones and J. R. Suarez: *A New High-Performance Ultrasonic Camera System*, Fifth International Symposium on Acoustical Holography Imaging, July 18–20, 1973. These improvements in the resolution quality of ultrasound images increase the ability of a system to detect small, focal lesions such as cancer, abscesses, or infarcts of less than one centimeter in diameter.

However, often more fundamental than the focal lesion itself, regardless of its size, is the state of the tissue surrounding the lesion. The pattern of the adjacent tissue plays a crucial role in the identification of specific diseases by supplying the physician with information concerning the local context of the bodily processes which are resulting in the lesion.

Compared to tumor nodules and the like, the structures of the surrounding normal tissue are relatively delicate. The tissue structure is essentially determined by the dimensions of the fibrous and vascular framework of an organ and is responsive to the pathologic processes.

It would therefore be highly desirable to be able to image such delicate patterns as those associated with, for example, the interstitial spaces of parenchymal organs, or the tertiary branching of major arteries of the heart, brain, kidneys and lungs, or the biliary ducts of the liver and the ductular system of the breast and pancreas. However, ultrasound imaging of these delicate tissues requires a resolution capability not presently possible with commercially known ultrasound scanning systems.

Accordingly, what is needed is an improved ultrasound imaging apparatus and method capable of high quality resolution for images of reflection for highly delicate tissue and the like. Such a device would provide a significant advancement in the state of the art by providing noninvasive diagnostic techniques through ultrasound imaging which could be used for pathogenesis, prevention and early detection of disease rather than being limited to the diagnosis of gross advanced lesions. Such an invention is disclosed and claimed herein.

BRIEF DESCRIPTION AND OBJECTS OF THE INVENTION

The ultrasound imaging apparatus and method of the present invention provides high quality resolution real time images of reflection by synthetically focusing ultrasound energy. Novel structure and method are provided for sending and receiving ultrasound energy waves and for reconstructing the images of reflection from an arbitrary waveform selected to optimize the system's resolution capability. Structure and method are also provided for digitally sampling the ultrasound energy which is received and for thereafter further improving the resolution of the reconstructed image of reflection by computer aided correction for refraction and attenuation of the ultrasound energy. High speed computer aided analysis also provides quantitative determinations for various acoustic parameters associated with the scanned object.

It is therefore a primary object of the present invention to provide improved apparatus and method for ultrasound imaging.

Another primary object of the present invention is to provide an improved ultrasound imaging apparatus and method for reconstructing images of reflection by synthetically focusing ultrasound energy.

Another object of the present invention is to provide an ultrasound imaging apparatus and method for reconstructing an image of reflection from an arbitrary waveform selected so as to maximize the system's resolution capability.

Yet another object of the present invention is to improve the resolution of an image of reflection by correcting the image for distortions arising from attenuation and refraction of the ultrasound energy as it passes through the object being scanned.

Yet another object of the present invention is to provide an ultrasound imaging apparatus for improved transmission and reception of ultrasound energy waves.

Yet another object of the present invention is to provide an ultrasound imaging apparatus and method capable of providing spatial resolutions of approximately one-half wavelength in static media such as body tissues.

These and other objects and features of the present invention will become more fully apparent from the following description and appended claims taken in conjunction with the accompanying drawings.

DETAILED DESCRIPTION OF THE PREFERRED EMBODIMENTS

Reference is now made to the figures wherein like parts are designated with like numerals throughout.

1. GENERAL

Figure 1:
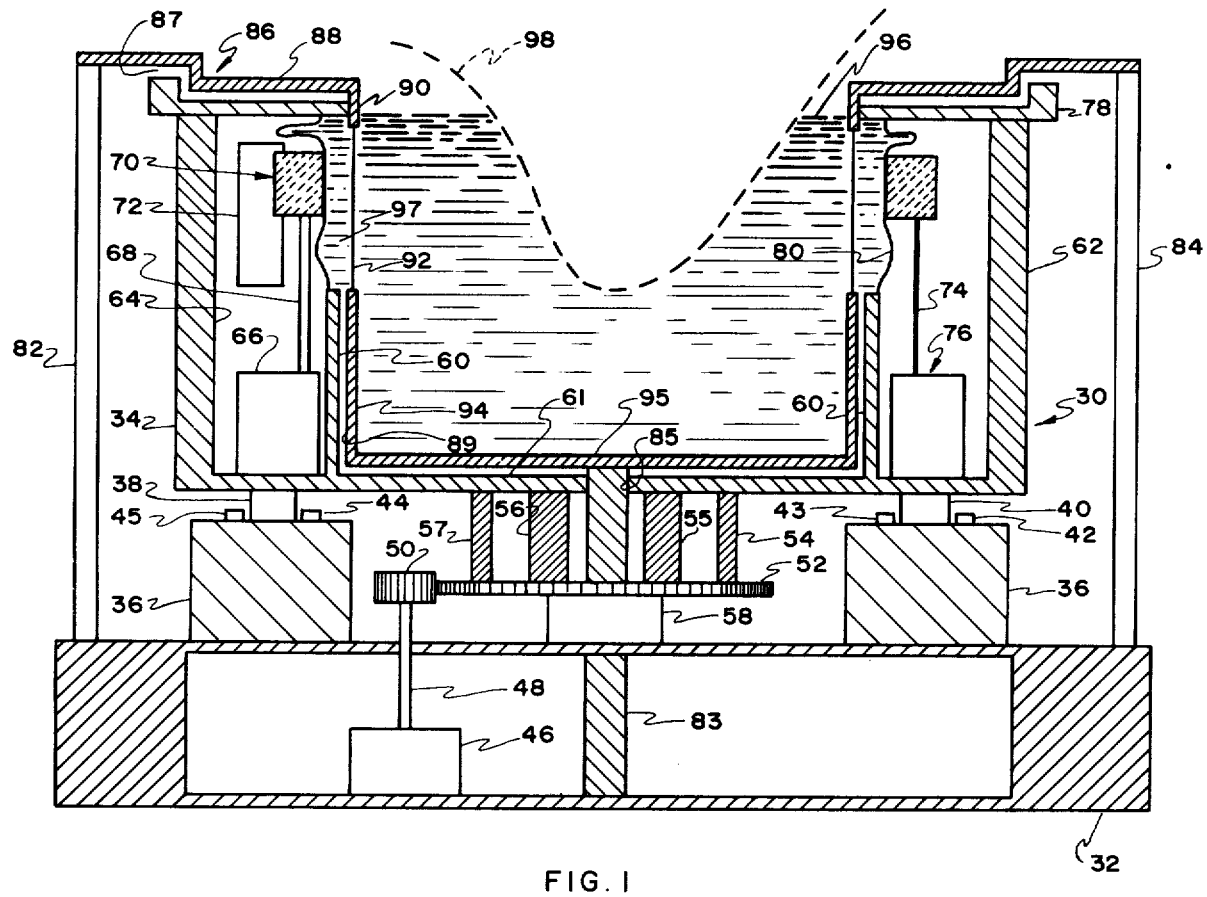
FIG. 1 is a side elevational view shown partially in cross section and schematically illustrates the ultrasound scanning apparatus of the present invention.

Reference is first made to FIG. 1 which generally illustrates the ultrasound scanning apparatus of the present invention. As shown in FIG. 1, the ultrasound scanning apparatus generally designated 30 consists of a fixed base 32 on which is rotatably mounted a movable carriage base 34. A cylindrical pedestal 36 is supported by the fixed base 32. Wheels 38 and 40 are attached to the underside of the movable carriage base 34. Small shoulders 42–45 formed on the upper surface of cylindrical pedestal 36 define a track along which the wheels 38 and 40 are guided.

A stepping motor 46 mounted within the fixed base 32 is joined by a shaft 48 to a small pinion gear 50. Pinion gear 50 engages a large drive gear 52. Pillars 54–57 are rigidly joined at one end to the top of drive gear 52 and at the opposite end to the underside of movable carriage base 34. Bearing block 58 supports drive gear 52 and movable carriage base 34.

Stepping motor 46 may be operated to turn the drive gear 52 which in turn will cause the movable carriage base 34 to rotate on top of the cylindrical pillar 36 within the tracks defined by shoulders 42–45. As hereinafter more fully described, rotation of the movable carriage base 34 may be employed to insure that an object is fully scanned from every possible angle.

With continued reference to FIG. 1, it will be seen that movable carriage base 34 has an inner cylindrical wall 60. The outer wall 62 and inner cylindrical wall 60 of movable carriage base 34 define a generally cylindrical chamber 64. Vertical drive motor 66 is mounted within chamber 64 and is connected by a shaft 68 to a circular ring of transducer arrays generally designated 70. Vertical drive motor 66 permits the circular ring of transducer arrays 70 to be vertically adjusted. Slide bracket 72 is mounted within the chamber 64 and serves to slidably guide the ring of transducer arrays 70 when it is vertically adjusted.

The ring of transducer arrays 70 is electrically connected through line 74 to an electronic circuit generally designated 76 which is also mounted within the cylindrical chamber 64 of the movable carriage base 34. As hereinafter more fully described, the electronic circuit 76 is used to transmit and receive ultrasound signals and to thereafter process the received signals so as to enable reconstruction therefrom of an image of reflection of the object being scanned.

Circular bracket 78 is attached to the top of the outer wall 62 of movable carriage base 34. A flexible, transparent window 80 extends between circular bracket 78 and the inner cylindrical wall 60 so as to enclose the transducer arrays 70, stepping motor 66 and electronic circuitry 76 within the chamber 64. The length of flexible window 80 is greater than the distance between bracket 78 and inner cylindrical wall 60. Window 80 thus serves as a flexible yet watertight seal which permits verticle motion of the transducer arrays 70. Transparent window 80 may be made of any suitable material such as plastic or rubber.

A stationary water tank generally designated 86 is adapted to fit within the movable carriage base 34. Water tank 86 consists of a fixed top plate 88 rigidly attached to vertical support bars 82 and 84. Support bars 82 and 84 are mounted on the fixed base 32. The length of support bars 82 and 84 is chosen such that the fixed top plate 88 of water tank 86 will be slightly suspended above the bracket 78 of movable carriage 34. Thus, a space 87 is provided between bracket 78 and fixed top plate 88. Additionally, space 89 will be provided between side 94 and bottom 95 of water tank 86 and cylindrical wall 60 and bottom 61 of movable carriage 34. A third support bar 83 extends through a central hole (not shown) provided in block 58 and drive gear 52. Support bar 83 also extends through a watertight opening 85 provided in the bottom 61 of movable carriage 34. Support bar 83 thus helps to support water tank 86 in spaced relation from movable carriage 34. Since water tank 86 is suspended in spaced relation from movable carriage base 34, water tank 86 will remain stationary as movable carriage 34 is rotated. As hereinafter more fully described, rotation of the carriage 34 permits the transducer arrays 70 to scan the object 98 from every possible position around the object 98.

Fixed top plate 88 has a short downwardly extending lip 90 which extends over the end of circular bracket 78. A rubber covered window 92 extends between the lip 90 and side 94 of the water tank. Window 92 encloses within space 89, water 97 or some other suitable ultrasound medium so as to acoustically couple the transducer array 70 to the water 96 contained in tank 86. The rubber covered window 92 also permits ultrasound energy signals to be transmitted therethrough by the transducer arrays 70 and insures that the patient will be protected in the event window 92 should be broken.

Those of ordinary skill in the art will readily recognize that the ultrasound scanning apparatus generally described above may be successfully employed to scan various objects or parts of the human anatomy, as for example a patient's breast, as illustrated at 98.

2. THE TRANSDUCER CONFIGURATION

Figure 2:
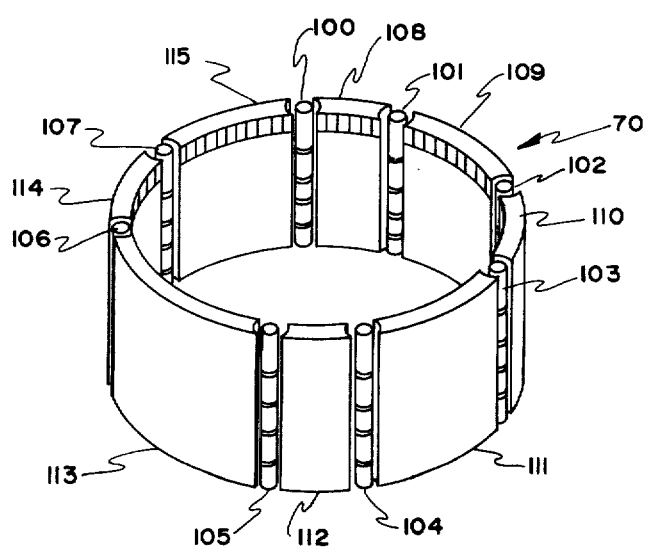
FIG. 2 is a perspective view illustrating one type of configuration which may be used for the transducer arrays employed in the ultrasound scanning apparatus of the present invention.
Figure 3:
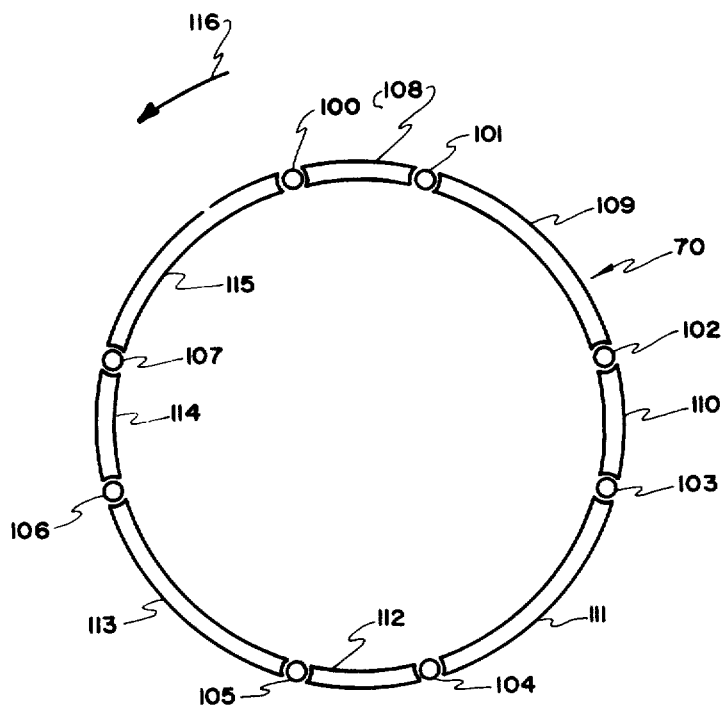
FIG. 3 is a plan view of the transducer arrays shown in FIG. 2.
Figure 4:
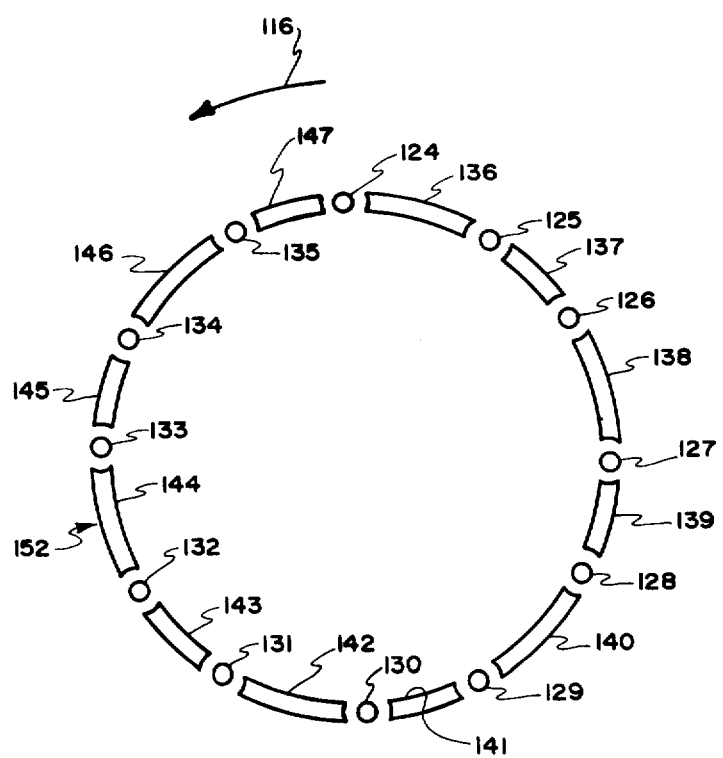
FIG. 4 is a plan view illustrating a second type of configuration for the transducer arrays of the ultrasound scanning apparatus of FIG. 1.

Reference is next made to FIGS. 2-4. FIG. 2 generally illustrates one suitable type of transducer configuration for the transducer arrays of FIG. 1. As shown in FIG. 2, the transducer configuration consists of eight transmitter arrays 100-107 and eight corresponding receiver arrays 108-115. The transmitter arrays 100-107 are thin, cylindrically shaped transducer arrays which provide point-source or line-source segment transmission of ultrasound energy signals. The receiver arrays 108-115 are arcuately shaped arrays which are interposed between each pair of transmitter arrays 100-107. For purposes hereinafter more fully described, every other receiver array (e.g. receiver arrays 108, 110, 112 and 114) has a shortened arcuate length.

Each of the transducer arrays 100-115 may be any of several well-known types of transducers. For example, transducers 100-115 may be piezoelectric type transducers which produce ultrasound energy signals directly from high frequency electrical voltages applied to the transducer. Alternatively, the transducer arrays 100-115 may be magnetostrictive type transducers having a magnetic coil (not shown) which receives the electrical oscillations and converts them into magnetic oscillations which are then applied to the magnetostrictive material to produce the desired ultrasound energy signals.

With continued reference to FIG. 2, it will be seen that the transducer arrays 100-115 are arranged so as to form a ring of arrays which encircles the object to be scanned. Significantly, by encircling the object with the transducer arrays 100-115, the arrays 100-115 may be quickly commutated by either mechanical methods, electronic methods or by both methods combined so as to completely scan the object in a much shorter time period. In the illustrated embodiment, commutation is achieved by both mechanical rotation by stepping motor 46 and by electronic triggering of transmitter arrays 100-107 in sequence, as described more fully below.

Commutation of the transmitter arrays 100-107 permits ultrasound energy to be transmitted from every possible position about the object, thus insuring that the echo data received (i.e. reflected ultrasound energy) is complete. Commutation of the receiver arrays 108-115 insures that all spaces between receiver arrays 108-115 (known as "sound holes") will be covered, thus insuring accurate collection of all ultrasound energy that is transmitted directly through the object being scanned. However, commutation of the receiver arrays 108-115 is not necessary where transmitter arrays 100-107 are also used to receive ultrasound signals. The circular ring configuration of transducer arrays 100-115 permits certain parts of the body to be scanned which would otherwise be inaccessible because of, for example, bones which might otherwise obscure the particular part of the anatomy to be scanned.

The method for commutating the arrays 100-115 is best understood by reference to FIG. 3. First, each of the transmitter arrays 100-107 is sequentially triggered so as to transmit an ultrasound energy signal. Immediately after each transmitter array 100-107 is triggered, arrays 108-115 receive ultrasound energy signals that have been either transmitted through or reflected by the object being scanned. Once this procedure has been followed for each of the transmitter arrays 100-107, the ring of arrays 70 is then mechanically rotated counterclockwise through a small angle, as designated by arrow 116. The mechanical rotation is achieved by the stepping motor 46 (see FIG. 1) which rotates the movable carriage base 34, as described above.

After rotation of the arrays 100–115 to a second position, each of the transmitter arrays 100–107 is again sequentially triggered and data is again collected through receiver arrays 108–115. This procedure is repeated until ultrasound energy has been transmitted at each possible point about the object.

Where the arrays 100–107 are used only for transmitting ultrasound energy, a second series of rotations must then be effected to cover the sound holes between each pair of receiver arrays 108–115. For example, by rotating transmitter array 101 to the position occupied by transmitter array 100, receiver arrays 109, 111, 113 and 115 will, because of their longer arcuate length, cover the spaces previously occupied by transmitter arrays 101, 103, 105 and 107. This procedure is repeated until all sound holes have been covered.

It should be noted that by increasing the number of arrays, electronic commutation may be used to reduce the angle through which the ring of transducer arrays must be rotated to achieve complete collection of both echo and transmission data. For example, as illustrated in FIG. 4, twelve transmitter arrays 124–135 are provided together with twelve receiver arrays 136–147. Again, it will be seen that every other receiver array (e.g. receiver arrays 137, 139, 141, 143, 145 and 147) has a shorter arcuate length. The increased number of transmitter arrays 124–135 together with the varying lengths for the receiver arrays 136–147 permit complete collection of echo and transmission data by rotating the ring of transducer arrays 152 through a much smaller angle than would be required for the ring of arrays 70 shown in FIGS. 2–3.

3. THE ELECTRONIC CIRCUITRY

As indicated previously in connection with FIG. 1, electronic circuitry generally designated 76 is housed within the movable carriage base 34. As hereinafter more fully described, the electronic circuitry 76 generates the ultrasound energy signals that are propagated through the object 98. The circuitry 76 thereafter detects, receives and processes the ultrasound energy signals that are reflected by and transmitted through the object 98 and then communicates the processed signals to a computer which interprets the signals and outputs the result on a visual display screen or other output device.

Of particular importance to the ultrasound scanning apparatus and method of the present invention is the provision of certain circuit components for developing a particular type of waveform for the signals from which the displayed image is reconstructed. Surprisingly high quality resolution for the reconstructed images of reflection is achieved by carefully controlling the type of waveform from which the displayed image is reconstructed, where resolution is defined as the minimal spatial separation between any two points on the reconstructed image of reflection which can be distinguished from one another.

For example, historically it has been found that for an optical instrument of diffraction aperture d and optical wavelength λ, the smallest divergence angle resolvable is approximately 0.61 λ/d, otherwise known as the Rayleigh criterion. In practical terms, the limit defined by the Rayleigh criterion means that two points cannot be closer than one-half of the optical wavelength and still be capable of being resolved. Until the present invention, ultrasound scanning devices have not been capable of resolving two points which have been closer than about 0.6 λ to 1.0 λ.

Significantly, resolving powers corresponding to 250 microns or less at 3 MHz (i.e. one-half wavelength) have been achieved for images of reflection reconstructed with the apparatus and method of the present invention.

Figure 5:
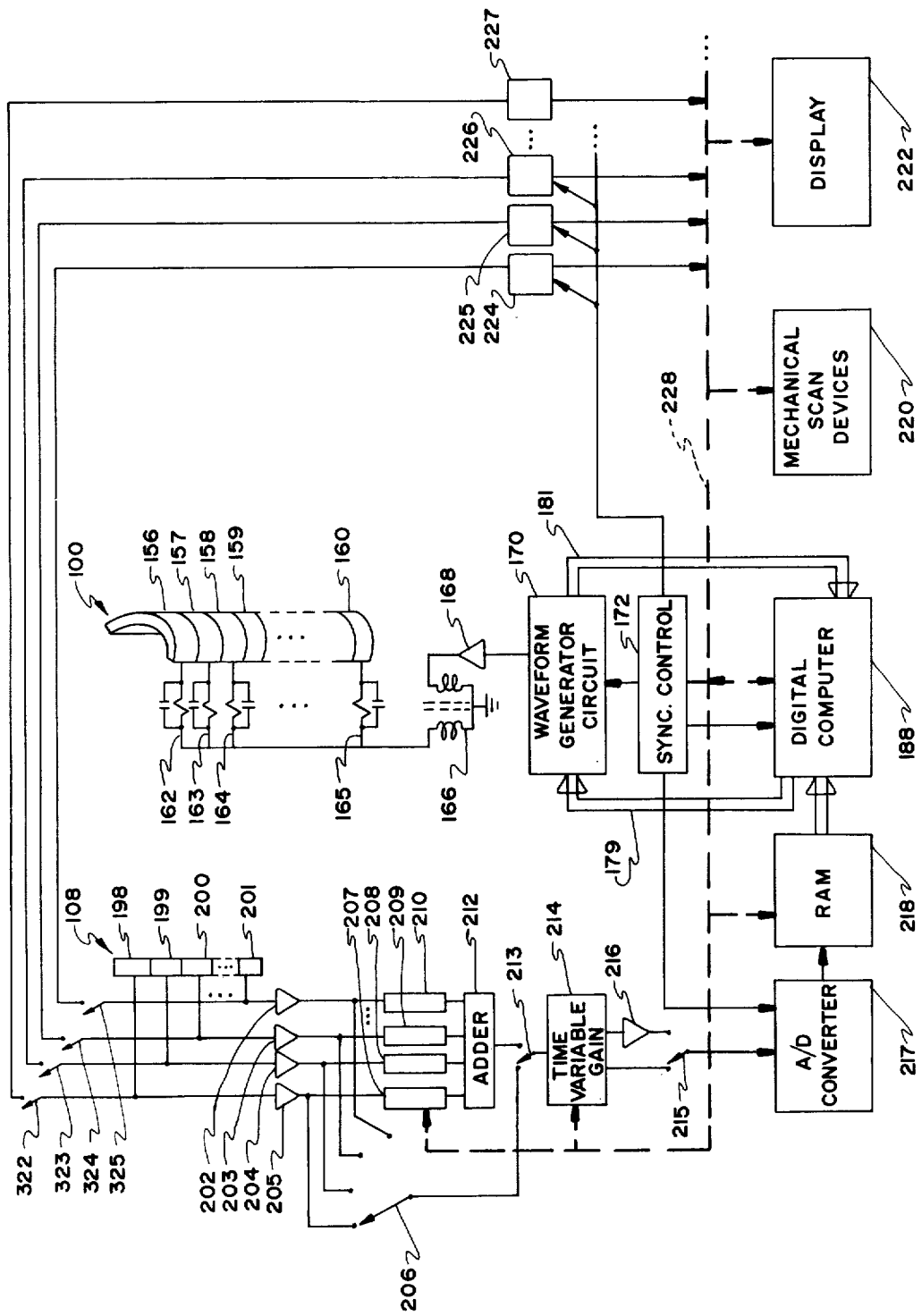
FIG. 5 is a schematic diagram illustrating one embodiment of the electronic circuitry used for transmitting and receiving ultrasound energy signals and for thereafter processing the received signals to permit reconstruction of an image of reflection for an object being scanned.

As shown in FIG. 5, each of the transducer elements 156–160 of transmitter array 100 is electrically connected to a corresponding resistive and capacitive (RC) network 162–165. It should be noted that each of the transmitter arrays 100–107 (see FIG. 2) are similarly connected. However, for ease of illustration only the connection for transmitter array 100 has been shown. The RC networks 162–165 are in turn connected to a transformer 166. Transformer 166 is connected through pulse amplifier 168 to the waveform generator circuit 170.

As hereinafter more fully described, waveform generator circuit 170 periodically generates a series of pulses, each pulse having the shape of a particular waveform selected as described below so as to significantly improve the resolution for the subsequently reconstructed image of reflection. Each of the pulses generated by waveform generator circuit 170 are synchronously clocked by synchronization control circuit 172 to pulse amplifier 168. Each signal pulse is then transmitted through the impedance matching transformer 166 to achieve maximum power transfer for the signals. RC networks 162–165 operate to distribute the power across the transducer array 100 by selectively varying the impedance at each transducer element 156–160. Thus, by increasing the impedance of RC networks 162 and 165 at the distal ends of array 100, the ultrasound signal transmitted by array 100 will have reduced side lobes. It will of course be recognized that RC networks 162–165 could also include inductance to provide improved flexibility in reducing the side lobes.

Figure 6:
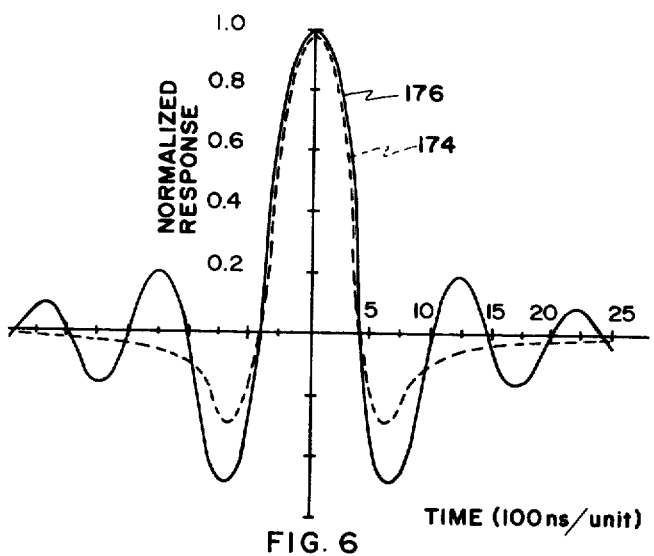
FIG. 6 is a graph illustrating two alternative types of waveforms that may be employed by the ultrasound scanning apparatus of the present invention for purposes of reconstructing an image of reflection.

FIG. 6 illustrates at 174 one suitable type of waveform developed for each signal transmitted by waveform generator circuit 170. Another suitable type of waveform that may be used advantageously in accordance with the apparatus and method of the present invention is shown at 176. Waveforms 174 and 176 are known in convolution reconstruction theory and Fourier transform theory developed in connection with X-ray computed tomographic imaging as the Tanaka-Iinuma kernel and the Ramachandran and Lakshiminaraynan kernel, respectively.

Waveform 174 is defined by the equation $$g(t,\sigma) = \frac{1}{2\pi\sigma^2}\left\{ 1 - \frac{t}{\sigma^2} \int_0^t \exp\left[ -\frac{1}{2\sigma^2}(t^2 - s^2) \right] ds \right\}$$

where $\sigma$ corresponds to the point in time where the magnitude first reaches zero and t represents time. Waveform 176 is defined by the equation $$f(t) = \frac{2 \sin(\pi t/5\beta)}{\pi t/5\beta} - \frac{\sin^2(\pi t/10\beta)}{(\pi t/10\,\beta)^2}$$

where $\beta$ is the point in time where the magnitude first reaches zero and t represents time. For $\sigma = 2.84$ and $\beta=1$, waveforms 174 and 176 produce equal reconstruction resolution.

Figure 7:
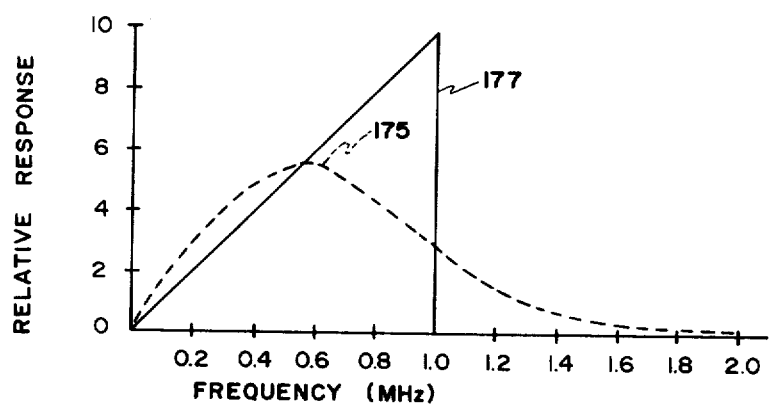
FIG. 7 is a graph illustrating the Fourier transforms for the waveforms of FIG. 6.

As can be seen from the Fourier transforms 175 and 177 (FIG. 7) which correspond to waveforms 174 and 176, the Tanaka Iinuma kernel (waveform 174) requires twice the bandwidth of waveform 176 to achieve the same resolution. However, waveform 174 has a better signal to noise ratio than waveform 176 and is thus better suited for noisy environments. Additionally, waveform 174 is better than waveform 176 for minimizing certain types of other distortions in the reconstructed image, such as concentric ring artifacts.

As more fully described below, ultrasound signals having the shape of waveforms 174 or 176 will, when combined for purposes of reconstructing an image of reflection, produce regions of both constructive and destructive interference which will significantly improve the point response of the combined signals so as to greatly enhance the resolution of the reconstructed image of reflection. Clearly, any type of waveform which is designed to improve the point response of the combined ultrasound signals in this manner could be utilized in accordance with the apparatus and method of the present invention. For example, it is possible to use waveforms that are intermediate between the waveforms 174 and 176.

Figure 8:
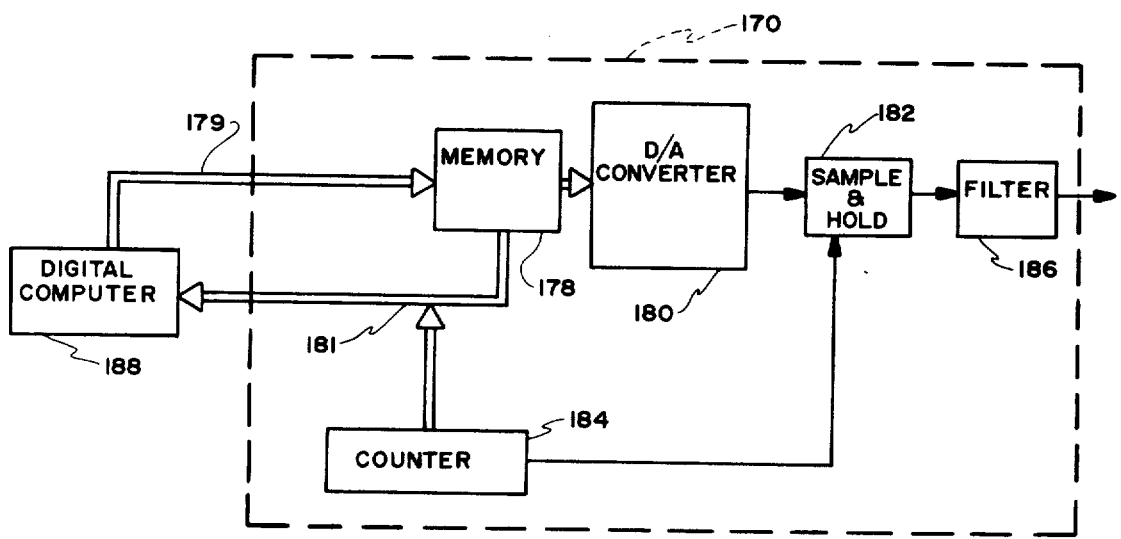
FIG. 8 is a functional block diagram illustrating the components of the waveform generator of the circuit in FIG. 5.

As shown in FIG. 8, waveform generator circuit 170 consists of five functional components. Memory circuit 178 is connected to a digital computer 188 through a read line 179 and through write line 181. Digital computer 188 may be any of several well-known types of commercially available main-frame computers or specially programmed mini-computers.

Figure 9:
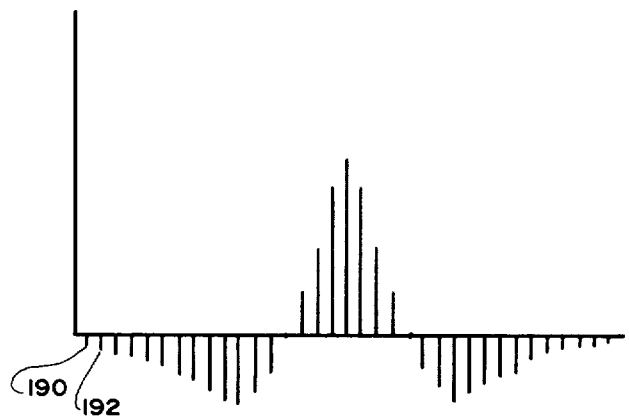
FIGS. 9, 10 and 11 are graphs illustrating the method employed by the waveform generator illustrated in FIG. 8.

Computer 188 determines the numerical value for a series of discrete points on the selected waveform, as for example waveform 174. These numerical values are stored in binary form in memory 178. Each of the discrete values stored in memory 178 is then sent to a digital-to-analog (D/A) converter 180. D/A converter 180 then transforms each of these digital values into a corresponding analog pulse, as illustrated in FIG. 9. These discrete analog pulses are then input to a sample and hold circuit 182. Sample and hold circuits such as that schematically illustrated at 182 are well known in the art and operate so as to hold each analog signal for a predetermined period of time. Counter 184 is used to control the amount of time that each signal is held by sample and hold circuit 182.

Figure 10:
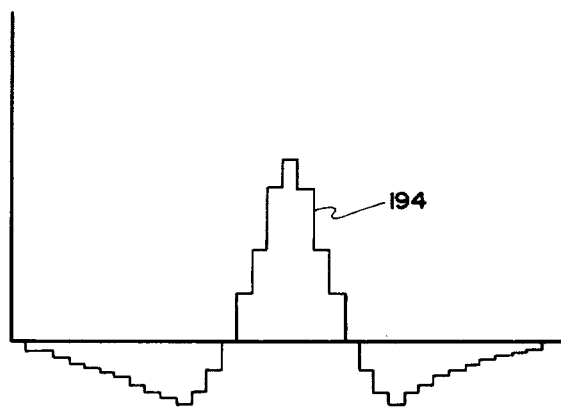
Figure 11:
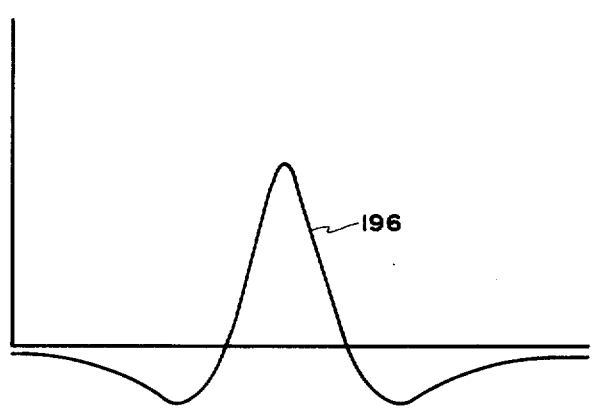

Thus, with each clock pulse from counter 184, the sample and hold circuit 182 retrieves one of the analog signals from D/A converter 180 and then holds the value of that signal for the duration of the clock pulse. For example, as illustrated in FIGS. 9 and 10, on the first clock pulse sample and hold circuit 182 will retrieve the analog pulse 190 and hold it for the duration of the clock pulse. On the next pulse analog signal 192 will be retrieved and held for the duration of the clock pulse and so on. Sample and hold circuit 182 thus outputs a waveform as illustrated at 194 in FIG. 10. Waveform 194 is then input to a low pass filter circuit 186. Low pass filter circuit 186 shapes the waveform 194 so as to output the desired signal pulse 196 illustrated in FIG. 11 which corresponds to the selected type of waveform 174.

Referring again to FIG. 5, it will be seen that each of the transducer elements 198-201 of receiving array 108 are electrically connected to one of the amplifiers 202-205. Again, it should be understood that each of the receiver arrays 108-115 (see FIG. 2) are similarly connected. However, for ease of illustration only the connection for receiver array 108 has been illustrated. Furthermore, it should also be noted that each of the transmitter arrays 100-107 may also be used to receive ultrasound energy signals, and they may also be connected in the same manner as receiver array 108. Additionally, although in the illustrated embodiment the transducer arrays 100-115 have been shown and described in a circular configuration, it will of course be appreciated that the electronic circuitry of FIG. 5 may also be employed with straight line linear transducer array configurations.

Each ultrasound signal received on one of the transducer elements 198-201 of receiver array 108 is detected and amplified by one of the amplifiers 202-205. The received ultrasound signals are then input through delay lines 207-210 to an analog adder circuit 212. Delay lines 207-210 and analog adder 212 vertically focus the received signals and thus may be used to increase the scanning system's speed by somewhat reducing the computational time needed to synthetically focus the received signals. However, the use of delay lines 207-210 and adder 212 decreases the resolution quality somewhat. Thus, delay lines 207-210 and adder 212 may be bypassed by switch 213 when desired. When delay lines 207-210 and adder 212 are bypassed by switch 213, each received signal is transmitted directly through multiplexer 206.

From the adder 212 or multiplexer 206, each received signal is then amplified by a time variable gain circuit 214. Time variable gain circuit 214 compensates for signal attenuation with time and thus keeps each signal within a range that may be accurately detected by the A/D converter 217. The signals are then compressed by a logarithmic amplifier 216 to reduce the storage space required for each signal after it is digitized by A/D converter 217. If desired, logarithmic amplifier 216 may precede the time variable gain circuit 214. Alternatively, amplifier 216 may be bypassed by switch 215.

A/D converter 217 digitizes each received ultrasound signal by converting it to a series of corresponding digital signals which are then stored in the random access memory (RAM) circuit 218. As hereinafter more fully described, digital computer 188 subsequently retrieves and interprets the signals stored in RAM 218 so as to reconstruct therefrom an image of reflection for the scanned object. The reconstructed image is then output on a display device 222 such as the screen of a CRT terminal or other suitable device.

In addition to carefully controlling the type of waveform from which the image of reflection is reconstructed, the ultrasound imaging apparatus of the present invention also improves the resolution quality for the reconstructed image of reflection by correcting the reconstructed image so as to eliminate distortions arising from attenuation and refraction of the transmitted ultrasound signals through the scanned object. As further illustrated in FIG. 5, each of the transducer elements 198-201 of the receiver array 108 is connected through one of the switches 322-325 to a corresponding time of flight detector 224-227. Time of flight detectors 224-227 determine the time it takes for the transmitted ultrasound energy signals to travel through the object being scanned. Alternatively, detectors 224-227 could be used to detect phase and amplitude.

Detectors 224-227 are switched so that only the receiver arrays directly across from the transmitter array being triggered will be used to detect the time of flight, thus eliminating reflected signals. For example, receiver arrays 111–113 are connected to the time of flight detectors when transmitter 100 (see FIG. 2) is triggered.

The synchronization control circuit 172 gates the time of flight data from detectors 224–227 through data bus 228 to the digital computer 188. As hereinafter more fully described, computer 188 uses the echo and time of flight data (or phase and amplitude data) to determine the refractive index and linear attenuation coefficient for the object being scanned. Computer 188 then determines the connecting ray between each point of the object and each of the transducer elements of the arrays. Data sampling times for each point in the reconstructed image are then corrected for refraction by computer aided integration of the object's refractive index along each connecting ray. Correction of the data for amplitude attenuation is similarly obtained by computer aided integration of the object's linear attenuation coefficient along the connecting rays.

Figure 12:
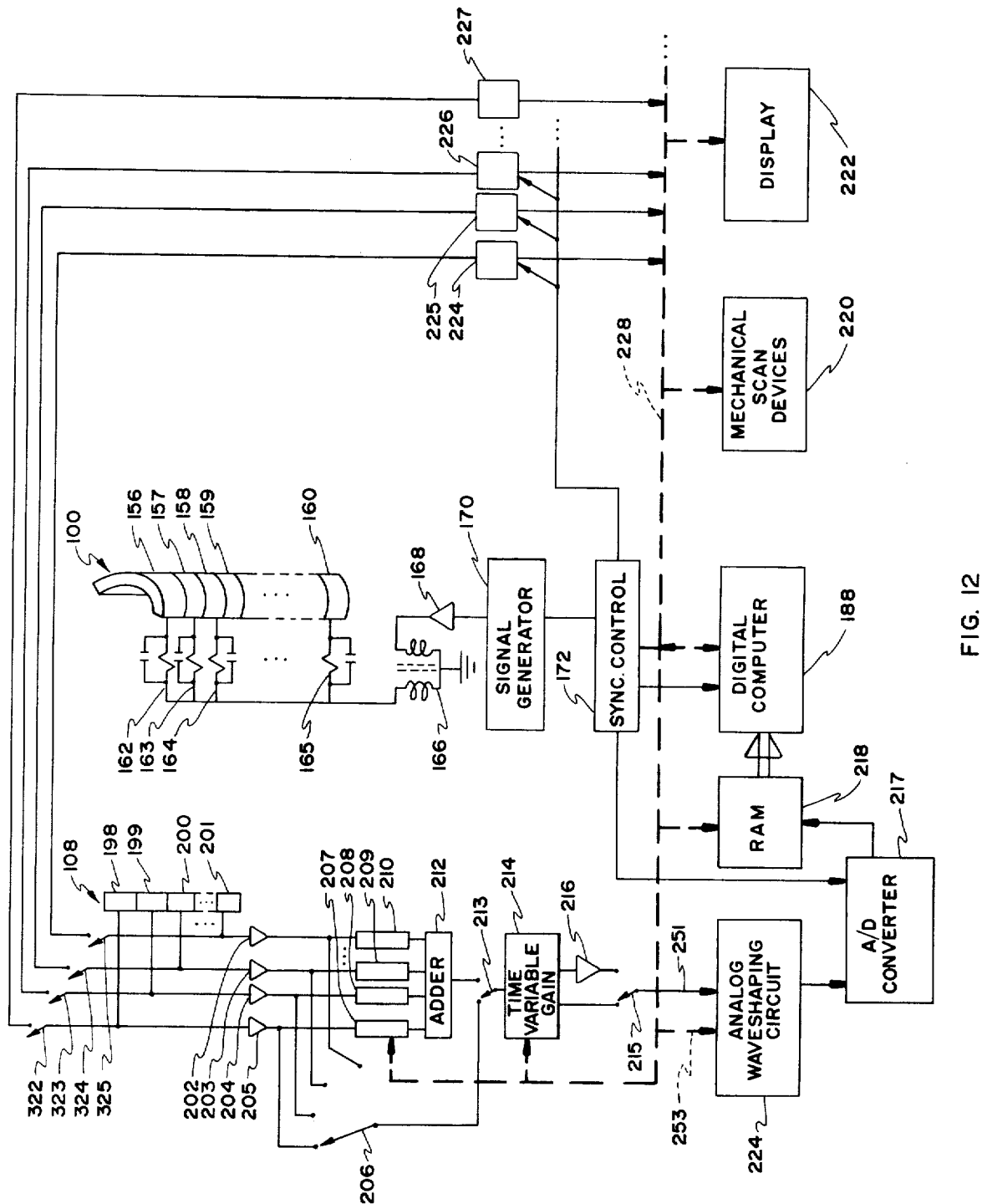
FIG. 12 is a schematic diagram illustrating a second embodiment of the electronic circuitry used for transmitting and receiving ultrasound energy signals and for thereafter processing the received signals to permit reconstruction of an image of reflection of a scanned object.

The electronic circuitry illustrated in FIG. 12 is essentially the same as that described previously in connection with FIG. 5 except for the manner in which the electronic circuitry develops the particular type of optimal waveform, as for example waveform 174, for each of the signals from which the image of reflection is reconstructed. As shown in FIG. 12, rather than developing the waveform 174 during the transmission mode, an analog waveshaping circuit 224 is used to process the ultrasound signals after they have been received so as to develop for each signal the desired waveform 174.

Figure 13:
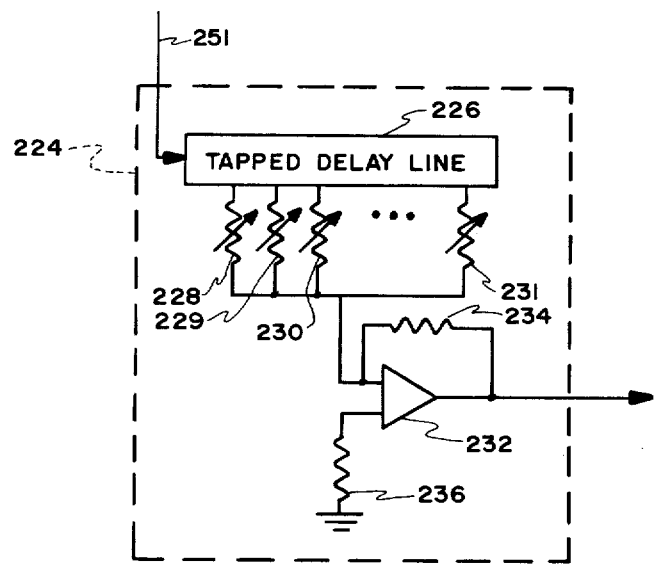
FIG. 13 is a schematic diagram illustrating one type of analog waveshaping circuit which may be employed with the electronic circuitry shown in FIG. 12.

FIG. 13 illustrates one type of circuit that may be used for the analog waveshaping circuit 224. As each ultrasound signal is received by transducer elements 198–201 (see FIG. 12), the signal is transmitted to a tapped delay line 226 (FIG. 13). Each tap of the delay line 226 is selectively weighted by a variable resistor 228–231. The weights for each of the taps of the delay line 226 are selected so that each portion of the signal which is accessed through the various taps of the delay line 226 will be multiplied by a value which corresponds to a discrete value on the waveform 174. Each portion of the signal which is thus multiplied is input through one of the terminals of the integrating amplifier 232. Resistors 234 and 236 are selected so that the appropriate biasing and integrating characteristics are achieved for the output of the amplifier 232. Additionally, it should be noted that although any suitable number of taps may be used for the delay line 226, increasing the number of taps will result in a waveform which more nearly corresponds to the desired waveform 174.

As integrating amplifier 232 sums the signals input from variable resistors 228–231, the desired waveform 174 will be output by amplifier 232. In this manner, each received ultrasound signal is convolved with the waveform 174 so as to develop for each signal a particular waveform having the shape of waveform 174. As described more fully below, when these signals are combined so as to reconstruct an image of reflection, the point response for the combined signals will be significantly improved so as to greatly enhance the quality of resolution of the image. As previously described, each such signal having the form of waveform 174 is then transmitted to the A/D converter 217 and RAM circuit 218.

Figure 14:
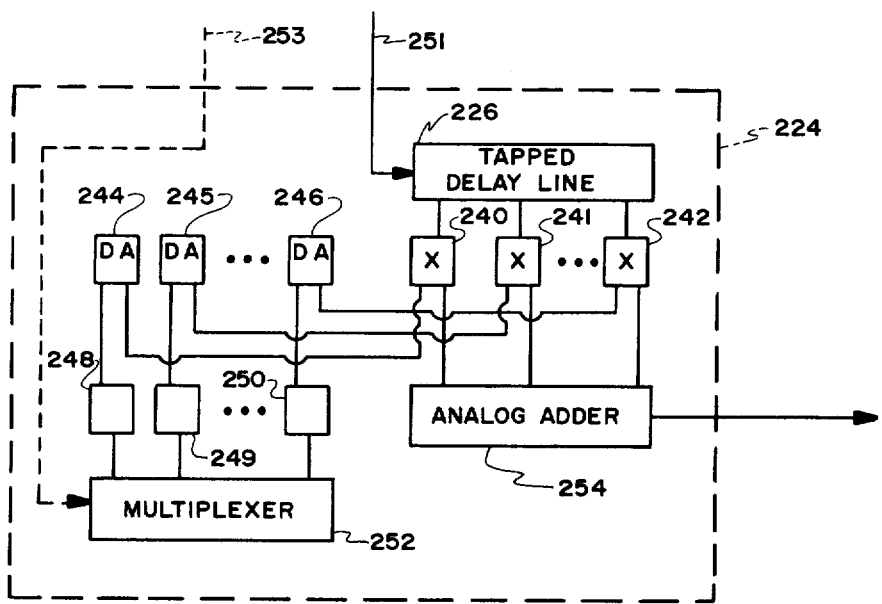
FIG. 14 is a functional block diagram illustrating a second type of analog waveshaping circuit which may be employed with the electronic circuitry of FIG. 12.

FIG. 14 illustrates a second type of circuit which may be used as the analog waveshaping circuit 224. As shown in FIG. 14, each of the taps of the delay line 226 is connected to a multiplier circuit 240–242. The multiplier circuits 240–242 are in turn connected to D/A converter circuits 244–246. The D/A converter circuits 244–246 are each connected to one of the latching circuits 248–250 which in turn are selectively accessed by a multiplexer 252.

Multiplexer 252 is connected through line 253 to the data bus 228. The digital computer 188 is used to calculate the tap weight values by which each portion of the signal received by delay line 226 is to be multiplied. The various tap weights are then transmitted through line 253 to multiplexer 252. Multiplexer 252 in turn selectively accesses the appropriate latching circuit 248–250. The particular tap weight from multiplexer 252 is then converted to an analog signal by one of the D/A circuits 244–246 and input to one of the corresponding multiplier circuits 240–242. In this manner the signal received by delay line 226 is broken down into various portions, each of which is multiplied by a tap weight value which corresponds to a discrete value on the waveforms 174.

As each portion of the signal is gated through the multiplier circuits 240–242 and multiplied, the analog adder circuit 254 sums the variously multiplied portions of the signal so as to develop therefrom the particular type of waveform 174 for each signal from which the image of reflection is to be reconstructed. Each signal which has thus been convolved with waveform 174 is then transmitted to the A/D converter 217 and RAM circuit 218.

Figure 15:
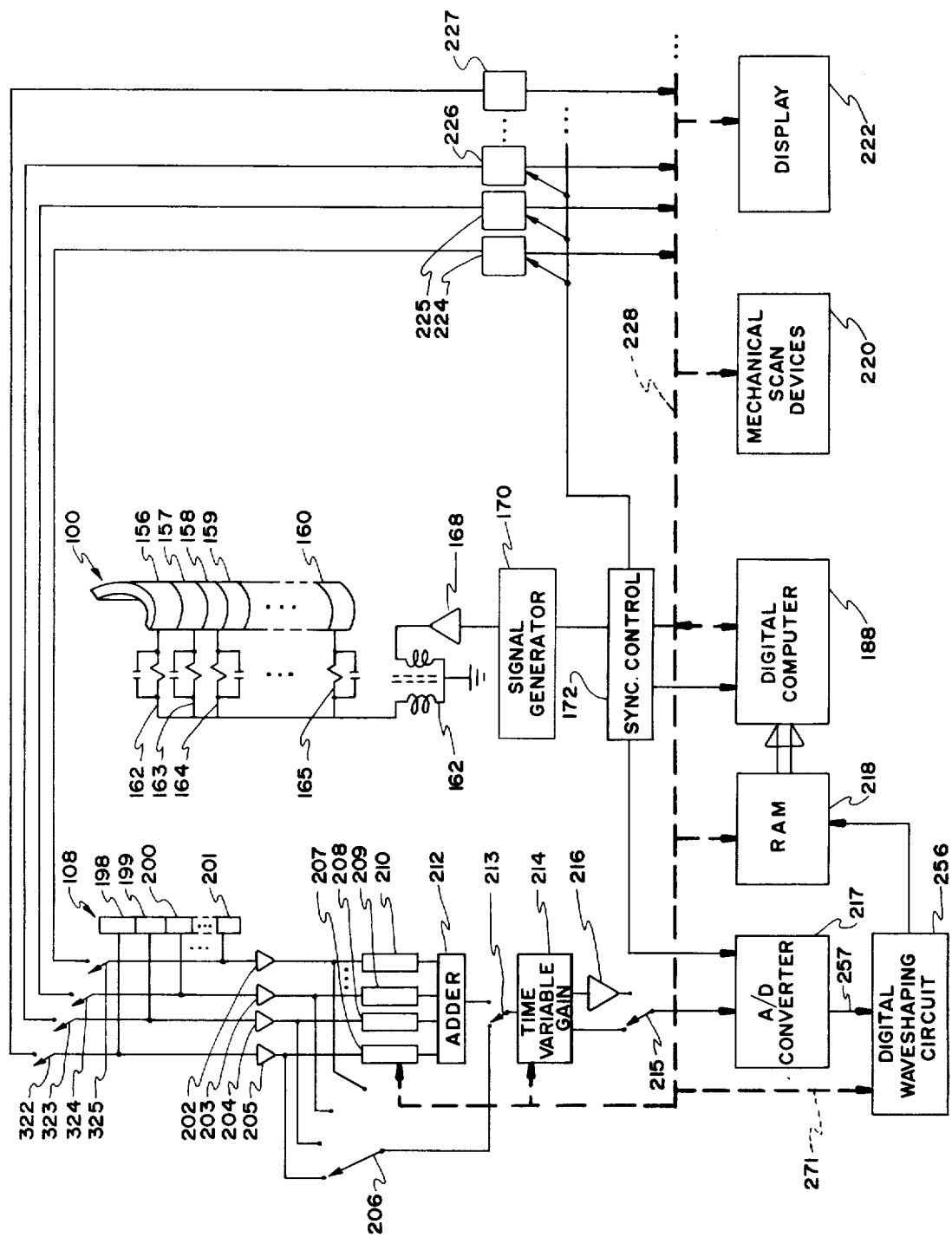
FIG. 15 is a schematic diagram of a third embodiment of the electronic circuitry for transmitting and receiving ultrasound energy signals and for thereafter processing the received signals to enable reconstruction of an image of reflection.

The electronic circuit in FIG. 15 is essentially the same as that described previously in connection with FIG. 12 except that the various ultrasound signals are processed through a digital waveshaping circuit 256 rather than being processed by an analog waveshaping circuit. As illustrated in FIG. 15, the digital waveshaping circuit 256 is connected between the A/D converter 217 and RAM circuit 218.

Figure 16:
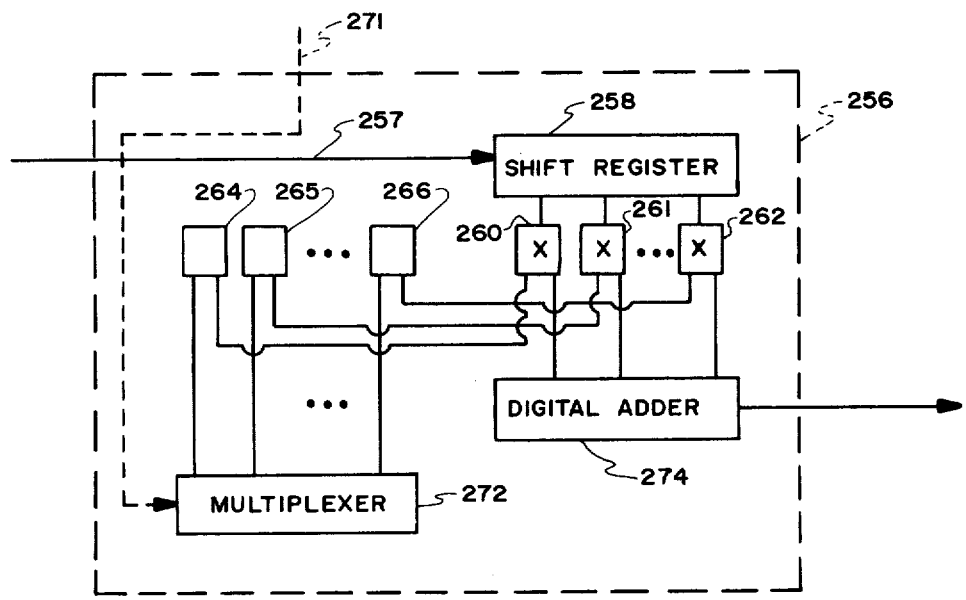
FIG. 16 is a functional block diagram illustrating one type of digital waveshaping circuitry used in conjunction with the circuit of FIG. 15.

FIG. 16 illustrates one type of circuit that may be used for the digital waveshaping circuit 256. As shown in FIG. 16, a series of digital signals corresponding to each received ultrasound signal is transmitted from the A/D converter 217 (see FIG. 15) through line 257 to a shift register 258. Each digital signal is in turn selectively accessed by a multiplier circuit 260–262. Again, any selected number of multiplier circuits 260–262 may be used. Each of the multiplier circuits 260–262 is connected to one of the latching circuits 264–266. Latching circuits 264–266 are in turn accessed through multiplexer 272. Multiplexer 272 receives from the digital computer 188 (see FIG. 15) the various values by which the multiplier circuits 260–262 are to multiply the digital signals stored in shift register 258.

Each value used to multiply the digital signals corresponds to a discrete value on the selected waveform, as for example waveform 174 (FIG. 6). Thus, as each latching circuit 264–266 is accessed by multiplexer 272, one of the digital signals stored in shift register 258 will be gated through the corresponding multiplier circuit 260–262 and input into the digital adder circuit 274. Digital adder circuit 274 then sums the digital signals which have been multiplied so as to develop from this process of convolution a series of digital signals corresponding to the desired waveform 174. The digital signals are then stored in RAM 218.

Figure 17:
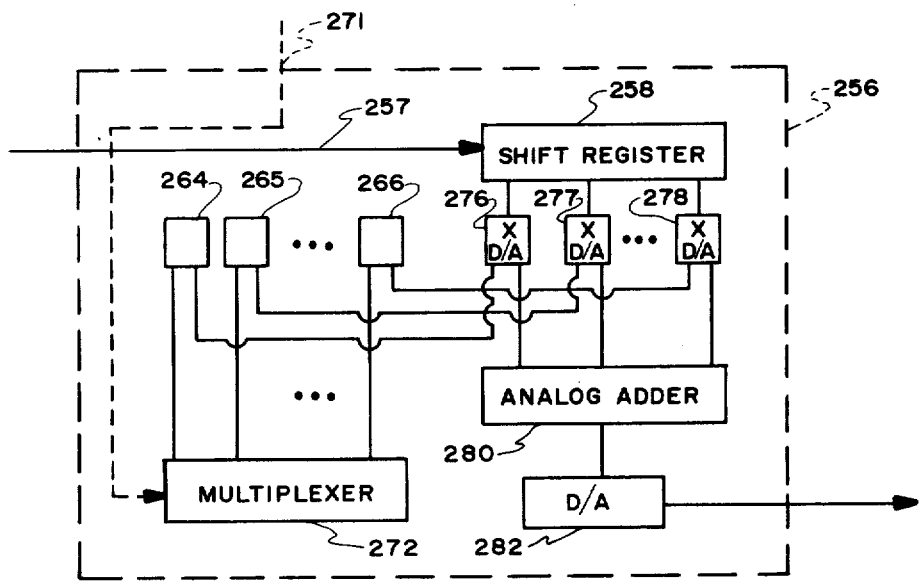
FIG. 17 is a functional block diagram illustrating a second type of digital waveshaping circuit which may be used with the circuitry of FIG. 15.

FIG. 17 illustrates a second circuit which may be used as a digital waveshaping circuit 256. The circuit of FIG. 17 differs from the circuit of FIG. 16 in that the multiplier circuits 276-278 are multiplying digital to analog circuits. Thus, as each digital signal is gated through the multiplying digital to analog circuits 276-278, the signals are multiplied and converted to analog signals. The analog signals are then added by an analog adder 280 so as to develop therefrom the particular type of waveform 174. The desired waveform is then transmitted to digital-to-analog converter 282 which transforms the waveform into a series of corresponding digital signals which are stored in RAM 218.

4. The Method of Image Reconstruction

In order to synthetically focus ultrasound energy so as to reconstruct an image of reflection of an object which has been scanned by the apparatus of the present invention, it is first necessary to develop a complete set of ultrasound signals which have been reflected and transmitted through the object being scanned. As previously described, this is accomplished by encircling the object 98 (see FIG. 1) with a ring of transducer arrays 70 (see also FIGS. 2-4). Each transmitter array 100-107 is sequentially triggered in a first position so as to propagate a series of ultrasound signals through the object 98. After each transmitter array 100-107 is triggered, receiver arrays 108-115 are used to receive the reflected and transmitted ultrasound energy signals. The ring of transducer arrays 70 is then rotated as described previously to a second position and the process is then repeated. The ring of transducer arrays 70 is rotated to as many positions as needed in order to transmit ultrasound signals from each point around the object. A second series of rotations is then effected in order to eliminate the sound holes occurring at the spaces between each pair of receiver arrays 108-115. In other words, data is transmitted and received at each position around the object 98 so as to insure a complete set of both echo and transmission data. As schematically illustrated at 220 in FIGS. 5, 12 and 15, the mechanical positioning devices for the scanner may be controlled by computer 188.

As previously indicated, although the apparatus and method of the present invention could be adapted to work with a linear array configuration, the circular array configuration described above greatly increases the speed and efficiency of the scanning process. Through the utilization of electronic commutation, the ultrasound scanning apparatus of the present invention may be operated at rates of 15 or more scans per second so as to develop real time images of reflection for the object which is being scanned.

For each received signal that is reflected by or transmitted through the object being scanned, a particular type of waveform 174 of 176 (see FIG. 6) is developed. As described above, the desired waveform 174 or 176 may be developed during the transmission mode by the waveform generator circuit 170 (see FIGS. 5 and 8). Alternatively, the ultrasound signals that are received may be subsequently convolved with the waveform 174 or 176 in an analog waveshaping circuit 224 (see FIGS. 12-14) or in a digital waveshaping circuit 256 (see FIGS. 15-17) so as to develop the desired waveform 174 or 176 for each received signal.

The desired waveform 174 or 176 may also be developed through software processing of the received signals after they have been digitized. However, the waveform generator circuit 170 or waveshaping circuits 224 or 256 shown in the illustrated embodiments are preferred over software processing techniques because they are much more rapid.

Once the desired type of waveform 174 or 176 has been developed for each transmitted or received ultrasound signal, each received signal is then converted to a series of corresponding digital signals and stored in the RAM circuit 218 (FIGS. 5, 12 and 15).

The digital signals stored in RAM circuit 218 are subsequently retrieved by the digital computer 188 and combined so as to reconstruct therefrom an image of reflection for the scanned object. The method for combining the stored signals is best understood from FIGS. 18-21.

Figure 18:
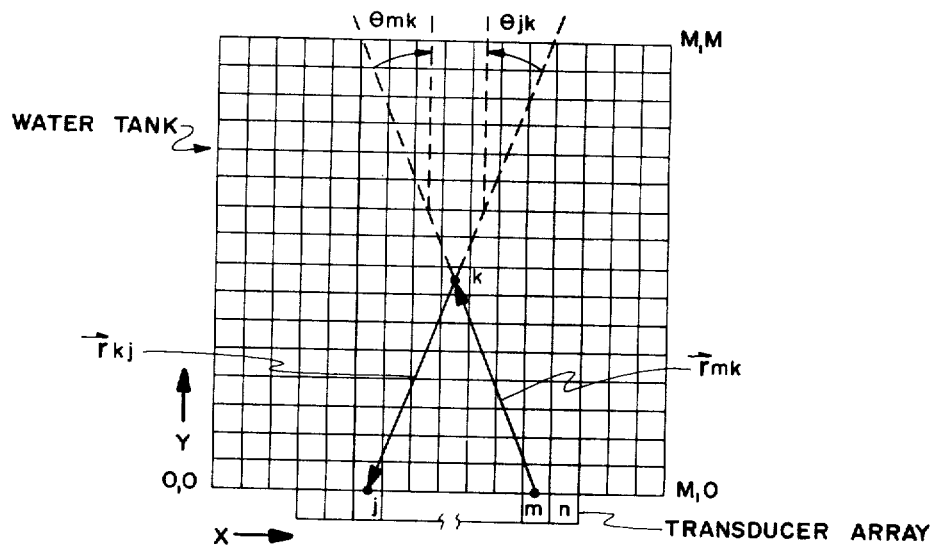
FIG. 18 is a graph from which a mathematical analysis of the apparatus and method of the present invention may be derived.

The mathematics for reconstructing an image of reflection from the received ultrasound signals may be derived by reference to FIG. 18. Let $P_k$ define a measure of the probability for acoustic amplitude scattering or reflection due to the existence of a scattering point "k" within the object being scanned. For the case of a very narrow pulse of ultrasonic energy, $P_k$ is given by the equation $$P_k = \sum_{m=1}^{n} \sum_{j=1}^{n} V(t,j,m) R(j,k) T(k,m) \qquad (1)$$

where $V(t, j, m)$ is the voltage sample at time t from the $j^{th}$ receiver array element when the $m^{th}$ transmitter array element was used as the transmitter. $R(j, k)$ and $T(k, m)$ are factors for correcting amplitude attenuation which occurs between the receiver element j and scattering point k and between transmitter element m and point k, respectively. $R(j, k)$ is found from the equation $$R(j,k) = [\exp(\int_k^j \alpha(s)ds)] [\int_k^j ds]^q \qquad (2)$$

where $\alpha$ is the linear attenuation coefficient measured at the center frequency of the transfer function of the system, exclusive of tissue, along the ray path $\vec{r}_{kj}$ connecting scattering point k and receiver element j, and q is a real number from 0.5 for cylindrical waves to 1.0 for spherical waves. Similarly, $T(k, m)$ is found from the equation $$T(k,m) = [\exp(\int_m^k \alpha(s)ds)] [\int_m^k ds]^q. \qquad (3)$$

The time t in equation (1) is corrected to account for refraction of the ultrasound energy as it passes through the object. The corrected time t is found from the equation $$t = \left[\int_m^k \frac{ds}{u(s)} + \int_k^j \frac{ds}{u(s)}\right] \frac{1}{\Delta t} \qquad (4)$$

where $\Delta t$ is the sampling interval time between successive samples in the digitized signal and $1/u$ is the object's refractive index.

One suitable computer program for determining the linear attenuation coefficient and refractive index from either the detected time of flight data or the detected phase and amplitude data, and for thereafter reconstructing an image of reflection by performing the calculations for equations (1)–(4) is set forth below.

Figure 19:
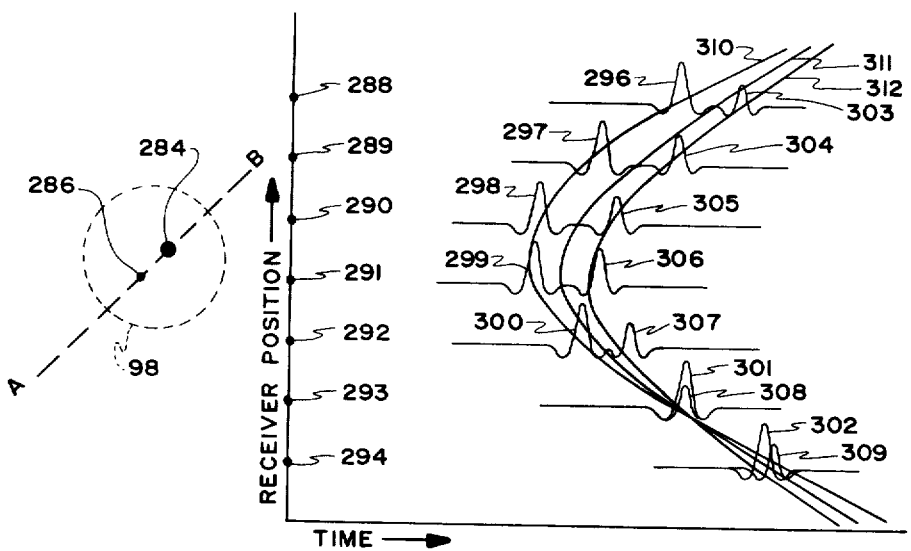
FIGS. 19–20 are graphs illustrating the effect of the waveforms of FIG. 6 on the point response of the signals from which an image of reflection is reconstructed.
Figure 20:
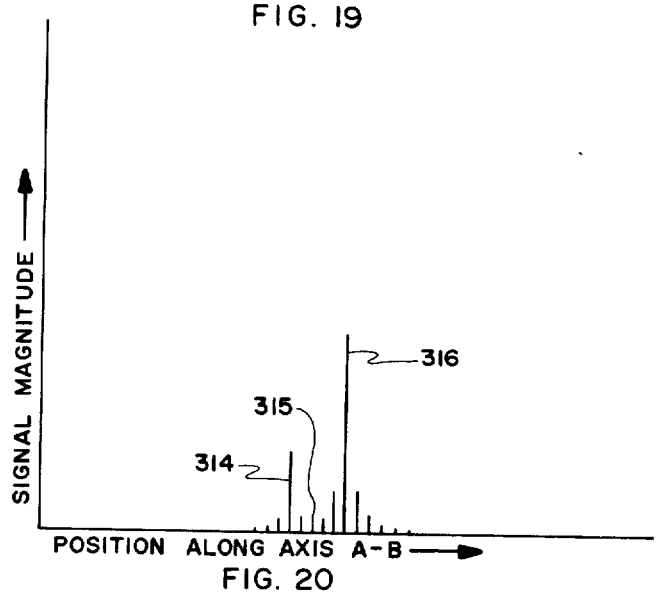
Figure 21:
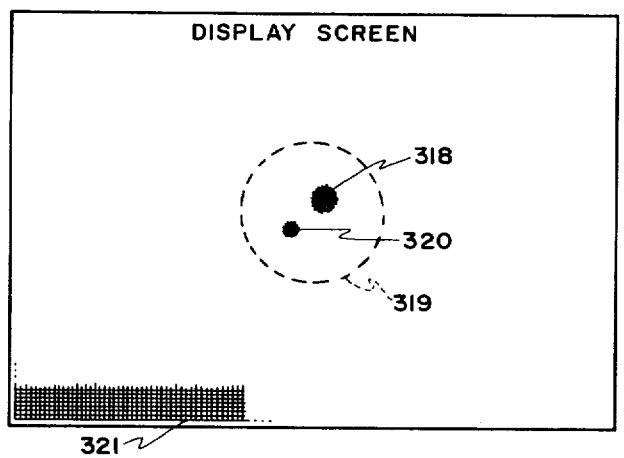
FIG. 21 is a schematic illustration of an image of reflection reconstructed from synthetically focused ultrasound energy in accordance with the apparatus and method of the present invention.

The concept which forms the basis for the abovedescribed mathematics is best understood by reference to FIGS. 19–21. For example, assume the existence of two scattering points 284 and 286 along an imaginary axis A–B within object 98, as illustrated in FIG. 19. Furthermore, assume that each of the points 288–194 represent transducer elements on a receiver array. Each of the transducer elements corresponding to the points 288–294 will detect a reflected ultrasound energy signal from the scattering points 284 and 286. For scattering point 284 a series of signals 296–302 will be detected. For the smaller scattering point 286 a series of smaller signals 303–309 will be detected.

It will be noted from FIG. 19 that the two sets of signals 296–302 and 303–309 corresponding to the scattering points 284 and 286 may be graphically located along a set of curves 310 and 312. The curves 310 and 312 graphically represent the spatial distribution which occurs as a function of time for each set of signals corresponding to a given scattering point in the object.

It can be shown that for a straight line transducer array, curves 310 and 312 will be hyperbollically shaped. For a ring of transducer arrays encircling the object, curves 310 and 312 will have a sinusoidal-like shape. Thus, for each scattering point in the object 98, a set of signals will be received which are spatially distributed along a curve that may be calculated from the physical parameters of the system.

In order to reconstruct an image of reflection from the received signals which have been subsequently processed and stored in RAM circuit 218, the computer 188 performs a line integration along each curve 310 and 312.

As shown in FIG. 21, the display screen is divided into a large number of very small picture elements such as partially illustrated at 321. For each picture element (commonly referred to as a "pixel"), computer 188 assumes the existence of a corresponding scattering point in object 98 and calculates the curve along which the received signals for the assumed scattering point would be distributed. Computer 188 than accesses all address locations in RAM 218 that correspond to the signals distributed along the curve for the assumed scattering point. If a scattering point in fact is found in the object 98 which corresponds to the scattering point assumed at a given pixel on the display screen, a series of values from the waveforms of the set of received signals will be added together by computer 188 when it integrates along the corresponding curve. Otherwise, no waveform values will be added by computer 188 when it integrates along the curve.

For example, if the computer 188 assumes scattering points at the pixels which correspond to scattering points 284 and 286 in the object 98, then values from each waveform corresponding to signals 296–302 and 303–309 will be added together as computer 188 integrates along curves 310 and 312. As shown in FIG. 20, this integration by computer 188 results in a signal value at a position along axis A–B that corresponds in magnitude and location to a particular scattering point. Thus, signal 314 corresponding to scattering point 286 results from the line integration along curve 310 and signal 316 corresponding to scattering point 284 results from the line integration along curve 312. Signals 314 and 316 are subsequently used to excite corresponding pixels on the display screen (see FIG. 21) so as to produce a reconstructed image 319 having scattering points 318 and 320 which correspond in size and spatial distribution to the actual object 98 and scattering points 284 and 286 within object 98.

Figure 22:
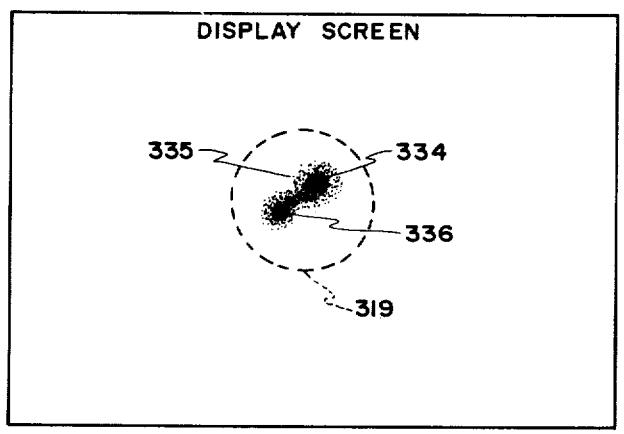
FIG. 22 is a schematic illustration of a blurred image of reflection.

As previously mentioned, one of the primary limitations which has operated to reduce the effectiveness of ultrasound scanning devices is the poor resolution that often results for the reconstructed image of reflection. As shown in FIG. 22, where the point response of the combined ultrasound signals is not well defined, the resulting image of reflection 319 will be badly blurred, as at 335, make resolution of the corresponding points 334 and 336 within the reconstructed image 319 difficult or impossible.

In contrast, it will be noted in FIGS. 20 and 21 that the point response of signals 314 and 316, derived from the line integrations of curves 310 and 312, is significantly enhanced by using a particular type of waveform 174 or 176 (see FIG. 6) for each signal 296–309. Since the waveforms 174 or 176 (see FIG. 6) have a very sharp peak at their center, integration of the curves 310 and 312 produces extreme signal values 314 and 316 at the positions along the axis A–B that correspond to actual scattering points 284 and 286. These extreme values are the result of constructive interference by the sharp center peaks of the waveforms 174 or 176 for the signals 296–302 and 303–309 situated along each curve.

Further, it will be noted that for those positions along axis A–B where no scattering point is found, the signals, as for example signal 315 (see FIG. 20), resulting from the integrations along corresponding curves, as for example curve 311 (see FIG. 19), will be at or near zero. For example, curve 311 (FIG. 19) corresponds to a position along axis A–B situated between scattering points 284 and 286 where no scattering point is found. Because curve 311 is situated so closely to curves 310 and 312, curve 311 will pass through the center peaks of some of the waveforms of the signals situated along curves 310 and 312, as for example the center peak of signal 300. However, curve 311 will also pass through the negative regions of others of the waveforms for the signals, as for example signals 302 and 309. As computer 188 integrates along curve 311, the negative values will tend to offset the positive values, thus keeping the resulting signal 315 (FIG. 20) near or at zero.

Thus, the negative portions of waveforms 174 or 176 will produce regions of destructive interference which will tend to improve the point response of the signals 314 and 316 by keeping signals at or near zero for points in the reconstructed image that do not correspond to scattering points in the object. At the same time, the sharp center peaks of waveforms 174 or 176 will produce regions of constructive interference which will tend to result in extreme signal values for points in the reconstructed image that correspond to scattering points within the object. As previously described, the improved point response for the combined signals results in a surprisingly high resolution image of reflection, as illustrated by points 318 and 320 of the reconstructed image 319 in FIG. 21.

Additionally, resolution of the reconstructed image 319 can be even further improved by readjusting the image to take into account the effect of attenuation and refraction of ultrasound signals passing through the object. Transmission data (i.e. time of flight or phase and amplitude data) and echo data (i.e. reflected ultrasound signals) are first detected by the electronic circuitry and sent to computer 188. Computer 188 then uses this data to determine the refractive index and linear attenuation coefficient for the object being scanned. Once these parameters have been determined, connecting rays between the elements of the receiver arrays and each point in the object are calculated by computer 188. The process is then repeated for the elements of the transmitter arrays.

Once the connecting rays have been obtained, data sampling times for each point in the reconstructed image are corrected for refraction by computer aided integration of the object's refractive index along each connecting ray from transmitter element to scattering point and from scattering point to receiver element. Computer 188 then interpolates to develop a corrected time address map for each point in the reconstructed image for a given transmitter and receiver pair. Similarly, the linear attenuation coefficient is integrated along each connecting ray and then computer 188 interpolates to develop an amplitude correction map for all points in the reconstructed image for a given transmitter and receiver pair. Computer 188 then causes the reconstructed image of reflection to be adjusted according to the time address and amplitude correction maps. The computer 188 then begins again for a new transmitter-receiver pair by recomputing new connecting rays and the time address and amplitude corrections are made a second time. This process may be repeated through a series of iterations until all transmitter-receiver pairs are completed. The result is an image of reflection of surprisingly high resolution quality.

Computer 188 may be programmed in accordance with the foregoing description in any suitable manner that is adapted for the particular type of computer 188 used. However, in order to fully disclose one presently preferred embodiment of the apparatus and method of the present invention, the following program listing is submitted. The listing is in ANSI Fortran, and includes programming for the determination of the refractive index and linear attenuation coefficient, for the reconstruction of an image of reflection, and for the correction of the reconstructed image of reflection to account for attenuation and refraction of the ultrasound energy as it passes through the object being scanned. It should of course be recognized that the invention lies in the apparatus and method defined by the claims, and is not intended to be limited by the representative program listing set forth below.

```
LN 0001        PROGRAM SYNFOCUS
LN 0002    C
LN 0003    C   THIS PROGRAM IS TO PRODUCE ECHO IMAGES WITH CORRECTION FOR
LN 0004    C   REFRACTION AND ATTENUATION.  THIS TECHNIQUE USES DIGITALLY
LN 0005    C   SAMPLED REFLECTION AND TRANSMISSION DATA OBTAINED FROM AN
LN 0006    C   APERTURE WHICH ENCLOSES OR CIRCUMSCRIBES THE SUBJECT OF STUDY.
LN 0007    C
LN 0008    C
LN 0009    C   M. TANAKA, MAYO CLINIC         JANUARY 1978
LN 0010    C   CDC-3500  ANSI FORTRAN
LN 0011    C
LN 0012    C
LN 0013        COMMON /LSD/ IPICT(4096),NUMANG,NUMPROJ,PI,VW,IPIXEL(4096),
LN 0014       $KOUNT(4096)
LN 0015        COMMON /10/ MAPATT(4096),INTEALFA(4096),MRADIUS(4096)
LN 0016        DIMENSION PX(120),PY(120)
LN 0017        DIMENSION ALFA(300)
LN 0018    C
LN 0019    C
LN 0020    C   *****************************************************************
LN 0021    C   NUMANG--- NUMBER OF VIEWS
LN 0022    C   NUMPROJ--- NUMBER OF PROJECTIONS USED FOR RAY TRACING
LN 0023    C   PI=--  PI=4.0*ATAN(1.0)
LN 0024    C   VW=--- SPEED OF SOUND IN WATER
LN 0025    C   IPICT(4096)--- ECHO IMAGE
LN 0026    C   IPIXEL(4096)--- SPEED OF SOUND
LN 0027    C   KOUNT(4096)--- NUMBER OF TIMES RAYS CROSS THE PIXEL
LN 0028    C   MAPATT(4096)--- ATTENUATION MAP
LN 0029    C   INTEALFA(4096)--- INTEGRATION OF ATTENUATION ALONG THE PATH
LN 0030    C   MRADIUS(4096)--- DISTANCE FROM THE SOURCE TO THE PIXEL ALONG THE RAY
LN 0031    C   PX(120)--- ARRAY OF THE X COORDINATE OF THE SOURCE POSITION
LN 0032    C   PY(120)--- ARRAY OF THE Y COORDINATE OF THE SOURCE POSITION
LN 0033    C   ALFA(300)--- THIS ARRAY COMES FROM SUBROUTINE FINDAL
LN 0034    C
LN 0035    C
LN 0036    C   *** DISK INFORMATION
LN 0037    C   USI=16  SPEED OF SOUND FOR EACH PIXEL
LN 0038    C   USI=10 UNPACKED DATA
LN 0039    C   USI=15 IMAGE SYNTHESIZED
LN 0040    C
LN 0041    C   ***
LN 0042    C
LN 0043    C   IMPROTANT--- ARRAYS (IPICT,IPIXEL,KOUNT) ARE BEING USED OTHER
LN 0044    C   THAN DISCRIPTIONS ABOVE.
LN 0045    C
LN 0046    C   *****************************************************************
LN 0047    C
LN 0048    C
LN 0049    C   RELMEM IS A SYSTEM SUBROUTINE TO RELEASE UNUSED MEMORY
LN 0050        CALL RELMEM
LN 0051    C
LN 0052    C
```

```
LN 0053      C      IFLAG=-1 *** CORRECTION WITH ATTENUATION ONLY
LN 0054      C      IFLAG= 0 *** CORRECTION WITH BOTH ATTENUATION AND REFRACTION
LN 0055      C      IFLAG= 1 *** NO CORRECTION
LN 0056      C
LN 0057             IFLAG=-1
LN 0058             IFLAG=0
LN 0059             IFLAG=1
LN 0060      C
LN 0061      C        FOR SIMULATION  DATA WAS CREATED AS FOLLOWS
LN 0062      C        A(REC)=A(INT)*SIGMA*EXP(-2*INT(ALFA*DS) )*R(0)**4/(INT(DS)**4)
LN 0063      C        FOR THE GEOMETRY PROVIDED FOR SIMULATION, WE LET
LN 0064      C        A(REC) FOR THE MINIMUM DISTANCE FROM THE SOURCE TO THE
LN 0065      C        SCATTERING POINT.  SIGMA WAS DERIVED FROM THE SPECIFIC SIMULATION
LN 0066      C
LN 0067             KR=123
LN 0068             SIGMA=36575.95833
LN 0069      C
LN 0070             CALL INIT(N,SORSTOP,STPT,WIDTH,R)
LN 0071             NSO=N*N
LN 0072             IF(IFLAG .NE. 1) GO TO 240
LN 0073             CALL FINDAL(ALFA,NUMPROJ,PI)
LN 0074      C
LN 0075      C
LN 0076      C
LN 0077      C      READ IPIXEL FROM THE OUTPUT TAPE
LN 0078             READ(60,101) IFILE
LN 0079         101 FORMAT(I10)
LN 0080             WRITE(61,102) IFILE
LN 0081         102 FORMAT(1X,*FILE ID OF OUTPUT TAPE WITH 4096 IMAGES IS*,I10)
LN 0082             CALL GETIMAGE(IPIXEL,N,IFILE,VW)
LN 0083      C      IPIXEL IS NOW THE ACOUSTIC SPEED
LN 0084             CALL DISKIO(16,1,1,IPIXEL(1),IPIXEL(4096),ISTAT)
LN 0085             IF(ISTAT .NE. 0) CALL TROUBLE(15,ISTAT)
LN 0086             CALL INTIAL(NSO,IPICT,IPIXEL)
LN 0087             REWIND 2
LN 0088         240 NEW=1
LN 0089             IF(IFLAG .EQ. 0) NEW=0
LN 0090             CALL POSTCUT(NEW)
LN 0091      C
LN 0092      C
LN 0093             READ(60,120) IFILE
LN 0094         120 FORMAT(I10)
LN 0095             WRITE(61,130) IFILE
LN 0096         130 FORMAT(1X,*IFILE NUMBER IS*,I10)
LN 0097      C
LN 0098      C ***  TRANSFER UNPACKED DATA TO DISK OF DSI=10
LN 0099      C
LN 0100             CALL GETECHO(NUMANG,IFILE,IPICT,IPIXEL,NBITS,NSAMP)
LN 0101             MY=NUMANG
LN 0102             NH=N/2
LN 0103             RA=0.96
LN 0104             AINC=PI/30.0
LN 0105             JAINC=1
LN 0106             NFT=NSAMP
LN 0107             XUP=1.2
LN 0108             XLO=-1.2
LN 0109             YUP=1.2
LN 0110             YLO=-1.2
LN 0111      C
LN 0112             SCONST=WIDTH/FLOAT(N)
LN 0113      C
LN 0114             XCEN=(XUP+YLO)/2.0
LN 0115             YCEN=(YUP+YLO)/2.0
LN 0116             MDELAY=1500
LN 0117             MDIGIN=100
LN 0118             NRX=1
LN 0119             NDIF=0
LN 0120             NSKIP=NDIF/JAINC
LN 0121      C
LN 0122             IF(IFLAG .EQ. 1) GO TO 331
LN 0123      C
LN 0124      C      ***************************************************************
LN 0125      C
LN 0126      C        THIS PROGRAM WAS DESIGNED MAINLY FOR SIMULATION.  WE ASSUME THE
LN 0127      C        KNOWLEDGE OF THE IMAGE OF ATTENUATION.  HOWEVER, ATTENUATION
LN 0128      C        IMAGE MAY BE RECONSTRUCTED AND STORE IN MAPATT.  THEN CONTINUE
LN 0129      C        THE PROGRAM.  IN THIS PROGRAM  ALFA=1( FREQUENCY INDEPENDENT
LN 0130      C        ATTENUATION) INSIDE THE OBJECT OF RADIUS RA=0.96 CM AND ALFA=0
LN 0131      C        OTHERWISE.
LN 0132      C
LN 0133      C      ***************************************************************
LN 0134      C
LN 0135             CALL ALFAMAP(N,XCEN,YCEN,SCONST,RA)
LN 0136      C      A(RECEIVER)=SIGMA*A0*EXP(-2*I(ALFA*DS) )*(ROW**4)/(ROWNOT**4)
LN 0137      C      WHERE SIGMA IS  SCATTERING COEFFCICIENT
LN 0138      C      ROW IS  DISTANCE FROM TRANSMITTER TO RECEIVER ALONG THE RAY
```

```
       331 CONTINUE
C ***    ZERO IPICT VALUE
         CALL INTIAL(NSQ,IPICT,KOUNT)
         CALL DISKIO(15,1,1,IPICT(1),IPICT(4096),ISTAT)
         IF(ISTAT .NE. 0) CALL TROUBLE(15,ISTAT)
C
C ***    LIST THE LOCATION OF THE TRANSMITTING POSITION IN TERM OF CARTETION
C            COORDINATES
C
         DO 140 IR=1,NTX,1
         IH=IR
         FIE=FLOAT(IR)
         ANG=(FIE-1.0)*AINC
         CA=COS(ANG)
         SA=SIN(ANG)
         PX(IR)=R*CA
         PY(IR)=R*SA
  140 CONTINUE
C
C ***    HERE DOES THE PIXEL DRIVEN ALGORITM ONE TRANSDUCER AT A TIME
C
         DO 160 IE=1,NTX,1
         IS=IE
         WRITE(61,656) IS
  656 FORMAT(1X,7IS=7,I6)
         TX=PX(IS)
         TY=PY(IS)
C
C
C        FOR THE REAL DATA, THIS SUBROUTINE STRAIGHT NEED TO BE MODIFIED
C        BY USING JEFRAY FOR EXAMPLE, TO COMPUTE INT.(ALFA*DS) FROM
C        THE PIXEL ALONG THE RAY.
C
         IF(IFLAG) 250,260,270
  250 CALL STRAIGHT(TX,TY,RA,R,XCEN,YCEN,SCONST,N)
         GO TO 270
C
C
C        DO RAY TRACING FOR ONE VIEW AT A TIME
  260 CONTINUE
         CALL TIMENIFE(IS,AINC,ALFA,SORSTOC,STOT,WIDTH,TX,TY)
C
C        KOUNT IS NOW THE VOLTAGE SAMPLES
C
  270 CONTINUE
         CALL DISKIO(10,IS,2,KOUNT(1),KOUNT(NPT),ISTAT)
         IF(ISTAT .NE. 0) CALL TROUBLE(10,ISTAT)
         CALL DISKIO(15,1,2,IPICT(1),IPICT(4096),ISTAT)
         IF(ISTAT .NE. 0) CALL TROUBLE(15,ISTAT)
         IF=IF+NSKIP
         IF(IF .GT. NTX) IF=IF-NTX
         RX=PX(IF)
         RY=PY(IF)
C
C
         DO 150 ID=1,NSQ,1
C        FIND THE COORDINATE OF THE CNTER OF ID, TH PIXEL
         INDEX=ID-1
         IY=INDEX/N
         IX=INDEX-N*IY
         EY=FLOAT(IY-NH)
         EX=FLOAT(IX-NH)
         XA=XCEN+EX*SCONST
         YA=YCEN+EY*SCONST
C        HENCE THE CENTER OF THE PIXEL IS
         X=XA+SCONST/2.0
         Y=YA+SCONST/2.0
         ANGL=180000000.0/FLOAT(NDIGIN)
C
C ***    FIND THE DISTANCE FROM TRANSDUCER TO (X,Y) AND (X,Y) TO RECEIVER
         DIS1=SQRT((TX-X)*(TX-X)+(TY-Y)*(TY-Y))
         DIS2=SQRT((RX-X)*(RX-X)+(RY-Y)*(RY-Y))
         DIST=DIS1+DIS2
C
C
C        DEL = DIFFERENCE OF TIME PROPAGATION FROM THE SOURCE TO
C        ID PIXEL.
C
         DEL=FLOAT(IPIXEL(ID))-(DIS1*AMUL)/VW
         DEL=2.0*DEL
         IF(IFLAG .NE. 0) DEL=0.0
         IPIXEL(ID)=IFIX(DEL*100.0)
C
```

```
LN 0223      C       FIND ITS ADDRESS IN DATA SPACE (USE LINEAR INTEPOLATION)
LN 0224              ADDRESS=(LIST*AMUL)/VW+DEL*FLOAT(MDELAY)
LN 0225              IADD=IFIX(ADDRESS)
LN 0226              IF(IADD .LT. 1 .OR. IADD .GT. NPT) IADD=2
LN 0227              IADDP1=IADD+1
LN 0228              FADD=FLOAT(IADD)
LN 0229              FADDP1=FLOAT(IADDP1)
LN 0230              VADD=FLOAT(KOUNT(IADD))
LN 0231              VADDP1=FLOAT(KOUNT(IADDP1))
LN 0232              IF(KOUNT(IADD) .LT. 3000 .OR. KOUNT(IADDP1) .LT. 3000) GO TO 560
LN 0233              WRITE(61,570) IE,KOUNT(IADD),KOUNT(IADDP1)
LN 0234          570 FORMAT(1X,'V IS TOO HIGH',3I10)
LN 0235              STOP
LN 0236          560 CONTINUE
LN 0237              DIF=VADDP1-VADD
LN 0238              VAL=VADD+(ADDRESS-FADD)*DIF
LN 0239      C
LN 0240              IF(IFLAG .EQ. 1) GO TO 332
LN 0241              PIS=FLOAT(MRADIUS(ID))/1000.0
LN 0242              ROW=PIS*PIS
LN 0243              ROWNOT=1.0
LN 0244              EEX=FLOAT(INTEALFA(ID))/1000.0
LN 0245              G=(ROW/ROWNOT)*EXP(EEX)
LN 0246              VAL=(VAL*G*G)/SIGMA
LN 0247      C
LN 0248          332 CONTINUE
LN 0249              IVAL=IFIX(VAL)
LN 0250              IF(IE .EQ. 1 .AND. ID .GT. 4000) WRITE(61,220)IE,ID,IPIXEL(ID),
LN 0251             5 DIST,DEL,VW,IADD,VADD,VADDP1,DIF,VAL,IPICT(ID)
LN 0252          220 FORMAT(1X,3I6,3(F10.4,2X),I10,4(F10.3,2X),I10)
LN 0253              IPICT(ID)=IPICT(ID)+IVAL
LN 0254          150 CONTINUE
LN 0255      C
LN 0256              IF(IE .NE. 5) GO TO 1531
LN 0257              CALL SMOOTH(IPIXEL)
LN 0258              CALL FINDMAX(IPIXEL,MAX,MIN,N)
LN 0259              JA=90
LN 0260              CALL WRITER(IPIXEL,N,JA,IFILE,MAX,MIN)
LN 0261      C
LN 0262              DO 872 JJJ=1,NSQ,1
LN 0263              IPIXEL(JJJ)=INTEALFA(JJJ)
LN 0264          872 CONTINUE
LN 0265              CALL SMOOTH(IPIXEL)
LN 0266              CALL PRINTER(IPIXEL,JA,NSQ)
LN 0267              CALL FINDMAX(IPIXEL,MAX,MIN,N)
LN 0268              JA=95
LN 0269              CALL WRITER(IPIXEL,N,JA,IFILE,MAX,MIN)
LN 0270         1531 CONTINUE
LN 0271      C
LN 0272              CALL DISKIO(15,1,1,IPICT(1),IPICT(4096),ISTAT)
LN 0273              IF(ISTAT .NE. 0) CALL TROUBLE(15,ISTAT)
LN 0274          160 CONTINUE
LN 0275              CALL DISKIO(15,1,2,IPICT(1),IPICT(4096),ISTAT)
LN 0276              IF(ISTAT .NE. 0) CALL TROUBLE(15,ISTAT)
LN 0277              JA=50
LN 0278              JA=51
LN 0279              JA=52
LN 0280              JA=53
LN 0281              CALL FINDMAX(IPICT,MAX,MIN,N)
LN 0282              CALL WRITER(IPICT,N,JA,IFILE,MAX,MIN)
LN 0283              CALL PRINTER(IPICT,JA,NSQ)
LN 0284      C
LN 0285              DO 520 MA=1,NSQ,1
LN 0286              MS=MA
LN 0287              IPICT(MS)=IABS(IPICT(MS))
LN 0288          520 CONTINUE
LN 0289      C
LN 0290              JA=60
LN 0291              JA=61
LN 0292              JA=62
LN 0293              JA=63
LN 0294              CALL FINDMAX(IPICT,MAX,MIN,N)
LN 0295              CALL WRITER(IPICT,N,JA,IFILE,MAX,MIN)
LN 0296              CALL PRINTER(IPICT,JA,NSQ)
LN 0297              END FILE 2
LN 0298              STOP
LN 0299              END
```

USASI FORTRAN DIAGNOSTIC RESULTS FOR SYNFOCUS

NO ERRORS

THE FOLLOWING ARE COMMON BLOCK NAMES OR NAMES NOT ASSIGNED STORAGE

```
LN 0001            SUBROUTINE INIT(N,SORSTOC,STOT,WIDTH,R)
LN 0002     C
LN 0003     C
LN 0004     C      THIS PROGRAM IS TO SET OR DEFINE PARAMETER FOR THIS PROGRAM
LN 0005     C      ***
LN 0006     C      SORSTOC--- SOURCE TO THE CENTER OF ROTATION IN CM
LN 0007     C      STOT--- SOURCE TO TARGET IN CM
LN 0008     C      WIDTH--- SIZE OF THE REGION RECONSTRUCTED IN CM
LN 0009     C      TEM--- TEMPRATURE OF WATER IN TANK IN C
LN 0010     C      VW--- SPEED OF SOUND IN WATER  M/SEC
LN 0011     C      ***
LN 0012     C
LN 0013            COMMON /LSD/ IPICT(4096),NUMANG,NUMPROJ,PI,VW,IPIXEL(4096),
LN 0014           $KOUNT(4096)
LN 0015            COMMON /IO/ MAPATT(4096),INTEALFA(4096),MRADIUS(4096)
LN 0016     C
LN 0017            READ(60,101) N,NUMANG,NUMPROJ
LN 0018        101 FORMAT(3I10)
LN 0019     C      IF IP=1, DATA IS 24 BITS
LN 0020     C      IF IP=2, DATA IS 12 BITS
LN 0021     C      IF IP=3, DATA IS 8 BITS
LN 0022     C
LN 0023            READ(60,102) IP
LN 0024        102 FORMAT(I10)
LN 0025            INCSUB=NUMPROJ/IP+3
LN 0026            PI=3.141592654
LN 0027            SORSTOC=14.0
LN 0028            STOT=25.0
LN 0029            WIDTH=2.4
LN 0030            R=14.0
LN 0031            TEM=23.5
LN 0032            T=TEM*TEM
LN 0033            VW=1402.385+5.03522*TEM-0.0583*T+0.0003453*T*TEM
LN 0034            VW=1500.0
LN 0035            WRITE(61,200) N,NUMANG,NUMPROJ,IP,SORSTOC,STOT,WIDTH,R,TEM,VW
LN 0036        200 FORMAT(///,5X,#N, NUMANG, NUMPROJ, IP, SORSTOC, STOT, WIDTH,      R
LN 0037           $, TEM,   VW#,//,I6,I6,I9,I6,F9.2,F7.2,F8.2,F5.1,F7.2,F8.2,///)
LN 0038            RETURN
LN 0039            END
```

JSASI FORTRAN DIAGNOSTIC RESULTS FOR INIT

NO ERRORS

THE FOLLOWING ARE COMMON BLOCK NAMES OR NAMES NOT ASSIGNED STORAGE

LSD

```
LN 0001            SUBROUTINE FINDAL(ALFA,NUMPROJ,PI)
LN 0002            INTEGER PROJ
LN 0003            DIMENSION ALFA(1)
LN 0004            SANG=PI/12.0
LN 0005     C      TO FIND ALFA WHICH IS THE ANGLE BETWEEN THE RAY AND CENTRAL RAY
LN 0006            FNPRO=FLOAT(NUMPROJ)
LN 0007            DO 100 PROJ=1,NUMPROJ,1
LN 0008            IPRO=PROJ
LN 0009            FPROJ=FLOAT(IPRO)
LN 0010            ALFA(IPRO)=SANG/2.0-(FPROJ-1.0)*SANG/(FNPRO-1.0)
LN 0011        100 CONTINUE
LN 0012            RETURN
LN 0013            END
```

JSASI FORTRAN DIAGNOSTIC RESULTS FOR FINDAL

NO ERRORS

```
LN 0001            SUBROUTINE POSIOUT(NEW)
LN 0002     C
LN 0003     C      M. TANAKA, MAYO CLINIC          JANUARY 1978
LN 0004     C
LN 0005            DIMENSION IHEAD(10)
LN 0006            LU=2
LN 0007     C
LN 0008     C      IF NEW=1, NEW TAPE
LN 0009     C      IF NEW=0, OLD TAPE
LN 0010     C
LN 0011            IF(NEW - 1) 210,200,210
LN 0012        200 ENDFILE LU
```

```
LN 0013              RETURN
LN 0014          210 CONTINUE
LN 0015              CALL SKIPEOF(LU)
LN 0016     C
LN 0017     C        THE OUTPUT TAPE NOT NEW, SO FIND 2 EOF
LN 0018           32 CONTINUE
LN 0019              BUFFER IN(LU,1) (IHEAD,IHEAD(10))
LN 0020           69 ISTAT=IFUNIT(LU)+2
LN 0021              GO TO(50,52,110,499,499,499,69,499),ISTAT
LN 0022           52 CONTINUE
LN 0023     C
LN 0024              CALL SKIPEOF(LU)
LN 0025              GO TO 32
LN 0026          110 CONTINUE
LN 0027              BACK SPACE LU
LN 0028     C
LN 0029              RETURN
LN 0030           50 CONTINUE
LN 0031              WRITE(61,60)
LN 0032           60 FORMAT( 12H  CANT WRITE)
LN 0033              STOP
LN 0034          499 WRITE(61,498)
LN 0035          498 FORMAT(1X,*UNRECOVERABLE ERROR*)
LN 0036              STOP
LN 0037              END

USASI FORTRAN DIAGNOSTIC RESULTS FOR POSIOUT

NO ERRORS

LN 0001              SUBROUTINE GETIMAGE(IPIXEL,N,IFILE,VW)
LN 0002     C
LN 0003     C        M. TANAKA, MAYO CLINIC       JANUARY 1978
LN 0004     C        ***
LN 0005     C        THIS PROGRAM IS TO GET THE *IMAGE* OF REFRACTIVE INDEX FROM
LN 0006     C        THE MAGNETIC TAPE OF DSI=2
LN 0007     C        NOTE-- VALUES OF ARRAYS ARE RELATIVELY SCALED.  THAT IS, EACH
LN 0008     C        PIXEL HAS AN EXPRESSION OF 1-VW/V(J)  WHERE V(J) IS THE SPEED
LN 0009     C        OF SOUND FOR J TH PIXEL
LN 0010     C        DMAX=1-1/1.1  CORRESPONDS TO 4096
LN 0011     C        DMIN=1-1/0.95  CORRESPONDS TO 0
LN 0012     C        YOU MAY AS WELL KEEP THE SPEED OF SOUND MAP IN THE TAPE, INSTEAD
LN 0013     C        AND IGNORE CALL VELOMAP
LN 0014     C
LN 0015     C        ***
LN 0016     C
LN 0017              DIMENSION IPIXEL(1)
LN 0018     C
LN 0019     C
LN 0020              NSQ=N*N
LN 0021              MT=2
LN 0022              CALL SKIPEOF(MT)
LN 0023           32 CONTINUE
LN 0024              BUFFER IN(MT,1) (IPIXEL(1),IPIXEL(10))
LN 0025           10 ISTAT=IFUNIT(MT)+2
LN 0026              GO TO(499,15,50,499,499,499,10,499),ISTAT
LN 0027           15 CONTINUE
LN 0028     C        TEST TO SEE IF IT IS A CORRECT FILE
LN 0029              IHV=IPIXEL(1)
LN 0030              IF(IHV - IFILE)205,305,205
LN 0031          205 CONTINUE
LN 0032              CALL SKIPEOF(MT)
LN 0033              GO TO 32
LN 0034          305 BUFFER IN(MT,1) (IPIXEL,IPIXEL(NSQ))
LN 0035           30 ISTAT=IFUNIT(MT)+2
LN 0036              GO TO(499,40,50,499,499,499,30,499),ISTAT
LN 0037           40 CONTINUE
LN 0038     C
LN 0039              CALL VELOMAP(NSQ,IPIXEL,VW)
LN 0040              RETURN
LN 0041           50 WRITE(61,109)
LN 0042          109 FORMAT(1X,*FILE MARK DETECTED*)
LN 0043              STOP
LN 0044          499 WRITE(61,498)
LN 0045          498 FORMAT(1X,*UNRECOVERABLE ERROR OCCURED*)
LN 0046              STOP
LN 0047              END
LN 0001              SUBROUTINE VELOMAP(NSQ,IP,VW)
LN 0002     C
LN 0003     C        M. TANAKA, MAYO CLINIC       JANUARY 1978
LN 0004     C
LN 0005              DIMENSION IP(1)
```

```
LN 0006     C
LN 0007     C       THIS SUBROUTINE IS TO CHAGNE IP(I) TO ACOUSTIC VELOCITY IN ITH PIXEL
LN 0008     C       DMAX AND MDIN SHOULD BE THE SAME AS THEM IN ART
LN 0009             DMAX=1.0-1.0/1.10
LN 0010             DMIN=1.0-1.0/0.95
LN 0011             CON=4096.0/(DMAX-DMIN)
LN 0012     C
LN 0013             DO 100 I=1,NSQ,1
LN 0014             A=FLOAT(IP(I))/CON
LN 0015             AC=(A+DMIN)*(-1.0)+1.0
LN 0016             IP(I)=IFIX(VW/AC)
LN 0017       100 CONTINUE
LN 0018             RETURN
LN 0019             END
```

USASI FORTRAN DIAGNOSTIC RESULTS FOR VELOMAP

NO ERRORS

```
LN 0001             SUBROUTINE INTIAL(NSQ,IPICT,KOUNT)
LN 0002             DIMENSION IPICT(1),KOUNT(1)
LN 0003             DO 100 I=1,NSQ,1
LN 0004             IPICT(I)=0
LN 0005             KOUNT(I)=0
LN 0006       100 CONTINUE
LN 0007             RETURN
LN 0008             END
```

USASI FORTRAN DIAGNOSTIC RESULTS FOR INTIAL

NO ERRORS

```
LN 0001             SUBROUTINE DISKIO(IUNIT,IBLK,KODIO,ISTART,ISTOP,ISTAT)
LN 0002     C       TO INPUT OR OUTPUT DISC RECORDS
LN 0003     C       IUNIT=DISC UNIT NUMBER
LN 0004     C       IBLK = DISC BLOCK NUMBER
LN 0005     C       KODIO= 1 FOR WRITE
LN 0006     C       KODIO= 2 FOR READ
LN 0007     C       ISTART= 1ST ADDRESS
LN 0008     C       ISTOP= LAST ADDRESS
LN 0009             IB=0
LN 0010       1     IERR=0
LN 0011             CALL LOCATE(IUNIT,IBLK,IERR,0)
LN 0012             IF(IERR.EQ.2) GO TO 9
LN 0013       30  IF(KODIO-1)4,3,4
LN 0014       4    BUFFER IN(IUNIT,1)(ISTART,ISTOP)
LN 0015             ISTAT=IFUNIT(IUNIT)+2
LN 0016             GO TO 61
LN 0017       3    BUFFER OUT(IUNIT,1) (ISTART,ISTOP)
LN 0018       60  ISTAT=IFUNIT(IUNIT)+2
LN 0019       61  GO TO(90,70,60,499,499,499,60,499),ISTAT
LN 0020     C       NORMAL COMPLETION
LN 0021       70  ISTAT=0
LN 0022             RETURN
LN 0023     C       FILE MARK DETECTED
LN 0024       80  ISTAT=1
LN 0025             WRITE(61,230) IUNIT,IBLK,KODIO
LN 0026       230 FORMAT(1X,*C*,3I10)
LN 0027             RETURN
LN 0028     C       PARITY ERROR OCCURED9 TRY AGAIN
LN 0029       90  IB=IB+1
LN 0030             WRITE(61,240) IUNIT,IBLK,KODIO
LN 0031       240 FORMAT(1X,*D*,3I10)
LN 0032             BACK SPACE IUNIT
LN 0033             IF(IB-3) 30,30,499
LN 0034     C       PARITY ERROR OR UNRECOVERABLE ERROR MESSAGE
LN 0035       499 CONTINUE
LN 0036             WRITE(61,250) IUNIT,IBLK,KODIO
LN 0037       250 FORMAT(1X,*E*,3I10)
LN 0038             ISTAT=-1
LN 0039             WRITE(61,498) IUNIT
LN 0040       498 FORMAT(1X,*ERROR  DSI IS*,I5)
LN 0041             STOP
LN 0042       9    WRITE(61,545)
LN 0043       545 FORMAT(1X,*ERROR HAPPENED*)
LN 0044             STOP
LN 0045             END
```

USASI FORTRAN DIAGNOSTIC RESULTS FOR DISKIO

NO ERRORS

```
LN 0001          SUBROUTINE SKIPEOF(J)
LN 0002     C
LN 0003     C      M. TANAKA, MAYO CLINIC      JANUARY 1978
LN 0004     C      THIS SUBROUTINE IS TO SKIP ONE E.O.F.
LN 0005     C
LN 0006          DIMENSION I(10)
LN 0007          IBEG=1
LN 0008          IEND=10
LN 0009          IC=0
LN 0010       20 CONTINUE
LN 0011       40 BUFFER IN(J,1) (I(IBEG),I(IEND))
LN 0012       60 ISTAT=IFUNIT(J)+2
LN 0013          GO TO(90,20,80,499,499,499,60,499),ISTAT
LN 0014       90 IC=IC+1
LN 0015          BACK SPACE J
LN 0016          IF(IC-3) 40,40,130
LN 0017       80 RETURN
LN 0018      130 WRITE(61,140)
LN 0019      140 FORMAT(1X,*PARITY ERROR DETECTED IN SKIPEOF SUBROUTINE*)
LN 0020          STOP
LN 0021      499 WRITE(61,498)
LN 0022      498 FORMAT(1X,*UNRECOVERABLE ERROR*)
LN 0023          STOP
LN 0024          END

USASI FORTRAN DIAGNOSTIC RESULTS FOR SKIPEOF

NO ERRORS

LN 0001          SUBROUTINE DETECHO(NTX,IFILE,IP,V,NBITS,NSAMP)
LN 0002     C
LN 0003     C      M. TANAKA, MAYO CLINIC      JANUARY 1978
LN 0004     C
LN 0005     C      SEARCHES TAPE OF LSI=4 FOR NTX FILES.  EACH FILE CONTAINS 1 SEGMENTS
LN 0006     C      AT THE END OF EACH FILE, THE TAPE CONTAINS E/F,  2 EOF SHOULD
LN 0007     C        BE DETECTED AT THE END OF EACH SCAN
LN 0008          DIMENSION IP(1),V(1)
LN 0009          INTEGER PLY
LN 0010          INTEGER V
LN 0011          IDSI=4
LN 0012          IC=0
LN 0013          PLY=0
LN 0014          GO TO 31
LN 0015     C    SEARCH 2 EOF
LN 0016       32 CONTINUE
LN 0017          CALL SKIPEOF(IDSI)
LN 0018      212 BUFFER IN(4,1) (IP(1),IP(64))
LN 0019       53 ISTAT=IFUNIT(IDSI)+2
LN 0020          GO TO(90,32,31,499,499,499,53,499),ISTAT
LN 0021       90 IC=IC+1
LN 0022          BACK SPACE IDSI
LN 0023          IF(IC-3) 212,212,130
LN 0024     C
LN 0025       31 CONTINUE
LN 0026     C
LN 0027          IC=0
LN 0028      215 BUFFER IN(4,1) (IP(1),IP(64))
LN 0029       54 ISTAT=IFUNIT(IDSI)+2
LN 0030          GO TO(100,50,110,499,499,499,54,499),ISTAT
LN 0031      100 IC=IC+1
LN 0032          BACK SPACE IDSI
LN 0033          IF(IC-3) 215,215,130
LN 0034       50 CONTINUE
LN 0035     C    TEST TO SEE IF IS A CORRECT FILE
LN 0036          IF(IFILE .NE. IP(1)) GO TO 32
LN 0037          NSAMP=IP(6)
LN 0038          NPT=NSAMP
LN 0039          NBITS=24/IP(7)
LN 0040          LAST=NSAMP/IP(7)+3
LN 0041     C
LN 0042          WRITE(61,334) IP(1),NTX,NSAMP,NBITS
LN 0043      334 FORMAT(5X,*INPUT ID IS*,I10,/,5X,*NUMBER OF TRANSMITTER AND RECEIV
LN 0044         $ER PAIRS IS*,I10,/,5X,*NUMBER OF SAMPLES IS*,I10,/,5X,*DATA IS*,I5
LN 0045         $,2X,*BITS*,///)
LN 0046     C
LN 0047          DO 10 I=1,NTX,1
LN 0048          I4=I
LN 0049          CALL SKIPEOF(IDSI)
LN 0050          IC=0
LN 0051       41 BUFFER IN(4,1) (IP(1),IP(LAST))
LN 0052       45 ISTAT=IFUNIT(IDSI)+2
```

```
LN 0053          GC TC(60,6,110,499,499,499,450,499),ISTAT
LN 0054    C
LN 0055       60 IC=IC+1
LN 0056          IF(IC .GT. 3) GO TO 130
LN 0057          BACK SPACE 4
LN 0058          GO TO 41
LN 0059        6 BLK=BLK+1
LN 0060    C
LN 0061          DO 560 MM=4,LAST,1
LN 0062          MM3=MM-3
LN 0063          V(MM3)=IP(MM)
LN 0064      560 CONTINUE
LN 0065          CALL SKEPTGN(V,NSAMP)
LN 0066          IF(I .EQ. 1) CALL PRINTER(V,I4,NSAMP)
LN 0067          NDSI=10
LN 0068          CALL DISKIO(10,BLK,1,V(1),V(NPT ),ISTAT)
LN 0069          IF(ISTAT .NE. 0) CALL TROUBLE(NDSI,ISTAT)
LN 0070       10 CONTINUE
LN 0071    C
LN 0072          RETURN
LN 0073      110 WRITE(61,260)
LN 0074      260 FORMAT(1X,#EOF DETECTED FOR INPUT TAPE#)
LN 0075          STOP
LN 0076      130 WRITE(61,270) BLK
LN 0077      270 FORMAT(1X,#PARITY ERROR OCCURED IN INPUT TAPE, BLK IS#,I5)
LN 0078          STOP
LN 0079      499 WRITE(61,498) ISTAT
LN 0080      498 FORMAT(1X,#UNRECOVERABLE ERROR, ISTAT IS#,I5)
LN 0081          STOP
LN 0082          END

USASI FORTRAN DIAGNOSTIC RESULTS FOR CETECHO

NO ERRORS

LN 0001          SUBROUTINE ALFAMAP(N,XCEN,YCEN,SCONST,R)
LN 0002    C
LN 0003    C       M. TANAKA, MAYO CLINIC       JANUARY 1978
LN 0004    C
LN 0005          COMMON /LSD/ IPICT(4096),NUMANG,NUMPROJ,PI,VW,IPIXEL(4096),
LN 0006         $KOUNT(4096)
LN 0007          COMMON /JO/ MAPATT(4096),INTEALFA(4096),MRADIUS(4096)
LN 0008    C
LN 0009    C    USED FOR SIMULATION PURPOSE
LN 0010    C    THE EQUATION OF SPHERE IS X*X + Y*Y = (0.96) ** 2
LN 0011    C
LN 0012    C    FOR THIS SIMULATION ALFA=1 INSIDE THE SPHERE
LN 0013    C         ALFA=0 OUTSIDE
LN 0014    C    VALUE OF MAPATT(I)=1000*MAPATT(I) FOR ALL I
LN 0015
LN 0016    C
LN 0017          RSQ=R*R
LN 0018          NSQ=N*N
LN 0019          NH=N/2
LN 0020    C
LN 0021          DO 150 ID=1,NSQ,1
LN 0022          MAPATT(ID)=0
LN 0023    C     FIND THE COORDINATE OF THE CENTER OF ID
LN 0024          INDEX=ID-1
LN 0025          IY=INDEX/N
LN 0026          IX=INDEX-N*IY
LN 0027          EY=FLOAT(IY-NH)
LN 0028          EX=FLOAT(IX-NH)
LN 0029          XA=XCEN+EX*SCONST
LN 0030          YA=YCEN+EY*SCONST
LN 0031          VAL=XA*XA+YA*YA
LN 0032          IF(VAL .GT. RSQ) GO TO 150
LN 0033          MAPATT(ID)=1000
LN 0034      150 CONTINUE
LN 0035          RETURN
LN 0036          END

USASI FORTRAN DIAGNOSTIC RESULTS FOR ALFAMAP

NO ERRORS

THE FOLLOWING ARE COMMON BLOCK NAMES OR NAMES NOT ASSIGNED STORAGE
     LSD
```

```
LN 0001         SUBROUTINE TROUBLE(LU,ISTAT)
LN 0002         WRITE(61,420) LU,ISTAT
LN 0003     420 FORMAT(1X,*TROUBLE IN DISKIO DSI AND ISTAT=*,2I5)
LN 0004         IF(ISTAT .EQ. 0) RETURN
LN 0005         STOP
LN 0006         END
```

USASI FORTRAN DIAGNOSTIC RESULTS FOR TROUBLE

NO ERRORS

```
LN 0001         SUBROUTINE SWEPTGN(V,NSAMP)
LN 0002         DIMENSION V(1)
LN 0003         INTEGER V
LN 0004         MBIAS=1000
LN 0005         DO 100 I=1,NSAMP,1
LN 0006         V(I)=V(I)-MBIAS
LN 0007     100 CONTINUE
LN 0008         RETURN
LN 0009         END
```

USASI FORTRAN DIAGNOSTIC RESULTS FOR SWEPTGN

NO ERRORS

```
LN 0001         SUBROUTINE PRINTER(V,ID,NUM)
LN 0002         INTEGER V(1)
LN 0003         WRITE(61,100) ID
LN 0004     100 FORMAT(///,5X,*ID=*,I5)
LN 0005         DO 333 MA=1,NUM,10
LN 0006         KK=MA+9
LN 0007         WRITE(61,444) MA,(V(KB),KB=MA,KK,1)
LN 0008     444 FORMAT(1X,I4,2X,10(I9,3X))
LN 0009     333 CONTINUE
LN 0010         RETURN
LN 0011         END
```

USASI FORTRAN DIAGNOSTIC RESULTS FOR PRINTER

NO ERRORS

```
LN 0001         SUBROUTINE TIMEMAP(ANG,AINC,ALFA,SORSTOC,STOT,WIDTH,TX,TY)
LN 0002   C
LN 0003   C       M. TANAKA, MAYO CLINIC      JANUARY 1978
LN 0004   C
LN 0005   C       THIS PROGRAM IS BY RAY-TRACING ALGORITHM TO COMPUTE
LN 0006   C       1. INTEGRATION OF ATTENUATION
LN 0007   C       2. TIME PROPAGATION
LN 0008   C       3. DISTANCE
LN 0009   C       FROM THE SOURCE TO EACH PIXEL
LN 0010   C
LN 0011         COMMON /LSD/ IPICT(4096),NUMANG,NUMPROJ,PI,VW,IPIXEL(4096),
LN 0012        $KOUNT(4096)
LN 0013         COMMON /IO/ MAPATT(4096),INTEALFA(4096),MRADIUS(4096)
LN 0014         DIMENSION LIST(150),WEIGHT(150)
LN 0015         DIMENSION ALFA(1)
LN 0016         INTEGER ANG,PROJ
LN 0017         ISS=ANG
LN 0018         KKKK=0
LN 0019         NUMH=NUMPROJ/2
LN 0020         N=64
LN 0021         NSQ=N*N
LN 0022         NSQH=NSQ/2
LN 0023         NS=N+N
LN 0024         PIW=PI*2.0
LN 0025         THETA=FLOAT(ISS-1)*AINC
LN 0026         IF(THETA .GT. PIW) THETA=THETA-PIW
LN 0027         DO 301 IJ=1,NSQ,1
LN 0028         KOUNT(IJ)=0
LN 0029         IPICT(IJ)=0
LN 0030         INTEALFA(IJ)=0
LN 0031         MRADIUS(IJ)=0
LN 0032     301 CONTINUE
LN 0033   C
LN 0034         CALL DISKIO(16,1,2,IPIXEL(1),IPIXEL(4096),ISTAT)
LN 0035         SCONST=WIDTH/FLOAT(N)
```

```
LN 0036          STOC=SORSTOC/SCONST
LN 0037          ST=STOT/SCONST
LN 0038          DO 300 PROJ=1,NUMPROJ,1
LN 0039          IPRO=PROJ
LN 0040          PHI=THETA-ALFA(IPRO)
LN 0041          LJ=0
LN 0042          CALL PTHFNDR(THETA,PHI,LIST,WEIGHT,NUMB,STOC,N,ST,LJ,ANG,IPRO,
LN 0043         $ XIN,YIN)
LN 0044          IF(LJ .EQ. 1) GO TO 300
LN 0045          IF(NUMB .LT. 0) GO TO 20
LN 0046          IF(NUMB .LE. 0) GO TO 300
LN 0047          IF(NUMB .GE. 150) GO TO 20
LN 0048   C
LN 0049          CALL TABLE(LIST,WEIGHT,NUMB,XIN,YIN,N,SORSTOC,SCONST,THETA,
LN 0050         $ISS,IPRO,NUMH,TX,TY)
LN 0051   C
LN 0052   C     MAKE SURE KOUNT(I) NOT 0 FOR ANY I.  CHANGE GEOMETRY IF NECESSARY
LN 0053    300 CONTINUE
LN 0054   C
LN 0055          DO 510 MA=1,NSQ,1
LN 0056          MA1=MA-1
LN 0057   C
LN 0058   C        IT IS POSSIBLE THAT SOME PIXELS MAY BE MISSED BY THE RAYS,
LN 0059   C        IT HAPPENS FREQUENTLY WHEN NUMPROJ IS SMALL.  IN THAT CASE,
LN 0060   C        FIND THE PIXEL AROUND ITS NHOOD.  HERE IPICT IS USED FOR THE
LN 0061   C        TIME PROPAGATION.
LN 0062   C
LN 0063          IF(IPICT(MA) - 800) 510,500,500
LN 0064    510 CONTINUE
LN 0065          LA=MOD(MA1,N)
LN 0066    570 CONTINUE
LN 0067          INDEX=MA1
LN 0068          IF(LA .EQ. 0) INDEX=MA1+2
LN 0069          IF(IPICT(INDEX) .GT. 800) GO TO 560
LN 0070          IF(MA - NSQH)720,720,710
LN 0071    710 MA1=MA1-N
LN 0072          GO TO 570
LN 0073    720 MA1=MA1+N
LN 0074          GO TO 570
LN 0075    560 IPICT(MA)=IPICT(INDEX)
LN 0076          INTEALFA(MA)=INTEALFA(INDEX)
LN 0077          MRADIUS(MA)=MRADIUS(INDEX)
LN 0078          KOUNT(MA)=KOUNT(INDEX)
LN 0079    500 CONTINUE
LN 0080   C
LN 0081          DO 305 MB=1,NS,1
LN 0082          MC=MB
LN 0083          A=FLOAT(IPICT(MC))
LN 0084          B=FLOAT(KOUNT(MC))
LN 0085          IPICT(MB)=IFIX(A/B+0.5)
LN 0086          C=FLOAT(INTEALFA(MC))
LN 0087          INTEALFA(MB)=IFIX(C/B+0.5)
LN 0088          D=FLOAT(MRADIUS(MC))
LN 0089          MRADIUS(MB)=IFIX(D/B+0.5)
LN 0090    305 CONTINUE
LN 0091          DO 620 LT=1,NSQ,1
LN 0092          IPIXEL(LT)=IPICT(LT)
LN 0093    620 CONTINUE
LN 0094          RETURN
LN 0095   C
LN 0096     20 WRITE(61,400) NUMB,ANG,PROJ
LN 0097    400 FORMAT(1X,/PROBLEM,NUMANG,PROJ/,3I10)
LN 0098          STOP
LN 0099          END
LN 0001          SUBROUTINE SMOOTH(PICT)
LN 0002          DIMENSION PICT(1)
LN 0003          DIMENSION WORK(128)
LN 0004          INTEGER PICT
LN 0005   C
LN 0006   C        LINEAR SMOOTHING BY 9 ELEMENTS.
LN 0007   C        M. TANAKA, MAYO CLINIC     JANUARY 1978
LN 0008   C
LN 0009          M=64
LN 0010          N=64
LN 0011          W1=4.0
LN 0012          W2=2.0
LN 0013          W3=1.0
LN 0014          MM2=M-2
LN 0015          MM1=M-1
LN 0016          NM2=N-2
LN 0017          M2=M*2
LN 0018   C
LN 0019          DO 110 K=1,M2,1
LN 0020          WORK(K)=FLOAT(PICT(K))
LN 0021    110 CONTINUE
```

```
LN 0022      C
LN 0023            DO 120 IY=1,MM2,1
LN 0024            IFST=IY*M+2
LN 0025            ILST=(IY+1)*M-1
LN 0026      C
LN 0027            DO 220 J=1,MM2,1
LN 0028            ICEN=IFST+(J-1)
LN 0029            I1=J
LN 0030            I2=J+1
LN 0031            I3=J+2
LN 0032            I4=J+M
LN 0033            I5=J+M+1
LN 0034            I6=J+M+2
LN 0035            I7=ICEN+M-1
LN 0036            I8=ICEN+M
LN 0037            I9=ICEN+M+1
LN 0038      C
LN 0039            SUMW=W1+4.0*W2+4.0*W3
LN 0040            TOTAL=W1*WORK(I5)+W3*(WORK(I1)+WORK(I3))
LN 0041           *      +W2*(WORK(I2)+WORK(I4)+WORK(I6))
LN 0042           *      +W3*(FLOAT(PICT(I7)+PICT(I9)))+W2*(FLOAT(PICT(I8)))
LN 0043            PICT(ICEN)=IFIX(TOTAL/SUMW)
LN 0044        220 CONTINUE
LN 0045      C
LN 0046            DO 230 L=1,M,1
LN 0047            K1=M+L
LN 0048            KSUB=(IY+1)*M+L
LN 0049            WORK(L)=WORK(K1)
LN 0050            WORK(K1)=FLOAT(PICT(KSUB))
LN 0051        230 CONTINUE
LN 0052        120 CONTINUE
LN 0053            RETURN
LN 0054            END

USASI FORTRAN DIAGNOSTIC RESULTS FOR SMOOTH

NO ERRORS

LN 0001            SUBROUTINE TABLE(LIST,WEIGHT,NUMB,XIN,YIN,N,R,SCONST,THETA,
LN 0002           $ IANG,IPROJ,NUMH,XT,YT)
LN 0003      C
LN 0004      C     ***
LN 0005      C     M. TANAKA, MAYO CLINIC     JANUARY 1978
LN 0006      C     THIS SUBROUTINE IS TO COMPUTE MRADIUS,INTEALFA FROM A SOURCE
LN 0007      C     POSITION TO PIXELS GIVEN BY A RAY.
LN 0008      C
LN 0009      C
LN 0010      C     IPIXEL(J)-- SPEED OF SOUND IN J TH PIXEL
LN 0011      C     IPICT(J)-- TIME PROPAGATION FROM THE SOURCE TO J TH PIXEL
LN 0012      C     KOUNT(J)--- NUMBER OF TIMES THE RAY CROSSES THE J TH PIXEL
LN 0013      C     MRADIUS(J)-- DISTANCE FROM THE SOURCE TO J TH PIXEL.
LN 0014      C     INTEALFA(J)--- INTEGRATION OF ATTENUATION ALONG THE RAY
LN 0015      C
LN 0016      C     ***
LN 0017      C
LN 0018      C     NOTE--- FROM ONE SOURCE POSITION, NUMPROJ PROJECTIONS ARE USED.
LN 0019      C     TO FIND THE AVERAGE, JUST DIVIDE BY KOUNT FOR EACH PIXEL.
LN 0020      C
LN 0021            COMMON /LSD/ IPICT(4096),NUMANG,NUMPROJ,PI,VW,IPIXEL(4096),
LN 0022           $KOUNT(4096)
LN 0023            COMMON /ID/ MAPATT(4096),INTEALFA(4096),MRADIUS(4096)
LN 0024            DIMENSION LIST(1),WEIGHT(1)
LN 0025            HALFN=FLOAT(N)/2.0
LN 0026            XIN=(XIN-HALFN)*SCONST
LN 0027            YIN=(YIN-HALFN)*SCONST
LN 0028            DIST=(XT-XIN)*(XT-XIN)+(YT-YIN)*(YT-YIN)
LN 0029            DIST=SQRT(DIST)
LN 0030            DELT=DIST/VW*100000.0
LN 0031            IF(IANG .LT. 10 .AND. IPROJ .EQ. NUMH) WRITE(61,400) IANG,IPROJ,
LN 0032           $XT,YT,XIN,YIN,DELT
LN 0033        400 FORMAT(10X,/CHECK1/,2I10,5F13.4)
LN 0034      C
LN 0035      C     UNIT OF DELT IS 100 NS
LN 0036      C
LN 0037      C
LN 0038            EX=0.0
LN 0039            DO 200 K=1,NUMB,1
LN 0040            MA=LIST(K)+1
LN 0041            H=(WEIGHT(K)*SCONST)/2.0
LN 0042            W=(H/FLOAT(IPIXEL(MA)))*100000.0
LN 0043            A=DELT+W
LN 0044            B=A+0.5
```

```
LN 0045            IPICT(MA)=IPICT(MA)+IFIX(B)
LN 0046            KOUNT(MA)=KOUNT(MA)+1
LN 0047            DELT=A+W
LN 0048      C
LN 0049            E=DIST+H
LN 0050            MRADIUS(MA)=MRADIUS(MA)+IFIX(E*1000.0)
LN 0051            DIST=E+H
LN 0052            EZ=FLOAT(MAPATT(MA))*H
LN 0053            EX=EX+EZ
LN 0054            INTEALFA(MA)=IFIX(EX)+INTEALFA(MA)
LN 0055            EX=EX+EZ
LN 0056       200 CONTINUE
LN 0057            RETURN
LN 0058            END

USASI FORTRAN DIAGNOSTIC RESULTS FOR TABLE

NO ERRORS

THE FOLLOWING ARE COMMON BLOCK NAMES OR NAMES NOT ASSIGNED STORAGE

LSD

LN 0001            SUBROUTINE PTHFNDR(THETA,PHI,LIST,WEIGHT,NUMB,SORSTOC,N,STOT,
LN 0002           & LJ,ANG,PROJ,XIN,YIN)
LN 0003      C
LN 0004      C       M. TANAKA, MAYO CLINIC         JANUARY 1978 MODIFIED
LN 0005      C
LN 0006            COMMON /LSD/ IPICT(4096),NUMANG,NUMPROJ,PI,VW,IPIXEL(4096),
LN 0007           &KOUNT(4096)
LN 0008            COMMON /IO/ MAPATT(4096),INTEALFA(4096),MRADIUS(4096)
LN 0009      C
LN 0010      C
LN 0011            DIMENSION LIST(1), WEIGHT(1)
LN 0012            DIMENSION F5(7)
LN 0013            INTEGER ANG,PROJ
LN 0014      C
LN 0015      C
LN 0016            PIO2=PI/2.0
LN 0017            PI32=PI*1.5
LN 0018            TWOPI=2.0*PI
LN 0019            STC=SORSTOC
LN 0020            STEPSZ=0.15
LN 0021            FLTN=FLOAT(N)
LN 0022            HALFN=FLTN/2.
LN 0023            STH=SIN(THETA)
LN 0024            CTH=COS(THETA)
LN 0025      C
LN 0026      C
LN 0027            YO=STH*STC+HALFN
LN 0028            XO=CTH*STC+HALFN
LN 0029      C
LN 0030            X3=XO-CTH*STOT
LN 0031            Y3=YO-STH*STOT
LN 0032      C
LN 0033      C
LN 0034      C
LN 0035            DXIN=COS(PHI)
LN 0036            DYIN=SIN(PHI)
LN 0037            IF(DXIN .EQ. 0.0) SLOPE=10000.0
LN 0038            SLOPE=DYIN/DXIN
LN 0039      C
LN 0040      C
LN 0041            IF(XO .GE. 0.0  .AND.  YO .GE. 0.0) GO TO 310
LN 0042            IF(XO .LE. 0.0  .AND.  YO .GE. 0.0) GO TO 330
LN 0043            IF(XO .LE. 0.0  .AND.  YO .LE. 0.0) GO TO 350
LN 0044            GO TO 370
LN 0045       310 CONTINUE
LN 0046      C     INTERSECT X=N OR Y=N
LN 0047            IF(XO .GE. FLTN  .AND.  YO .GE. FLTN) GO TO 311
LN 0048            GO TO 312
LN 0049       311 CONTINUE
LN 0050            XIN=FLTN
LN 0051            YIN=SLOPE*(XIN-XO)+YO
LN 0052            IF(YIN .GE. 0.0  .AND.  YIN .LE. FLTN) GO TO 210
LN 0053      C
LN 0054      C     TRY Y=N
LN 0055       313 CONTINUE
LN 0056            YIN=FLTN
LN 0057            XIN=XO+(YIN-YO)/SLOPE
LN 0058            IF(XIN .GE. 0.0  .AND.  XIN .LE. FLTN) GO TO 210
LN 0059            GO TO 500
```

```
LN 0060        312 CONTINUE
LN 0061            IF(Y0 - FLTN) 314,313,313
LN 0062        314 CONTINUE
LN 0063            XIN=FLTN
LN 0064            YIN=SLOPE*(XIN-X0)+Y0
LN 0065            IF(YIN .GE. 0.0 .AND. YIN .LE. FLTN) GO TO 210
LN 0066            GO TO 500
LN 0067        370 CONTINUE
LN 0068      C
LN 0069      C    INTERSECT Y=0 OR X=N
LN 0070            IF(X0 - FLTN) 372,371,371
LN 0071        371 CONTINUE
LN 0072            XIN=FLTN
LN 0073            YIN=Y0+SLOPE*(XIN-X0)
LN 0074            IF(YIN .GE. 0.0 .AND. YIN .LE. FLTN) GO TO 210
LN 0075      C    TRY Y=0
LN 0076        372 CONTINUE
LN 0077            YIN=0.0
LN 0078            XIN=X0+(YIN-Y0)/SLOPE
LN 0079            IF(XIN .GE. 0.0 .AND. XIN .LE. FLTN) GO TO 210
LN 0080            GO TO 500
LN 0081      C
LN 0082        330 CONTINUE
LN 0083      C    INTERSECT EITHER X=0 OR Y=N
LN 0084            XIN=0.
LN 0085            YIN=Y0-SLOPE*X0
LN 0086            IF(YIN .GE. 0.0 .AND. YIN .LE. FLTN) GO TO 210
LN 0087      C    TRY Y=N
LN 0088            YIN=FLTN
LN 0089            XIN=X0+(YIN-Y0)/SLOPE
LN 0090            IF(XIN .GE. 0.0 .AND. XIN .LE. FLTN) GO TO 210
LN 0091            GO TO 500
LN 0092        350 CONTINUE
LN 0093      C    INTERSECT EITHER X=0 OR Y=0
LN 0094            XIN=0.
LN 0095            YIN=Y0-X0*SLOPE
LN 0096      C    INTERSECT X=0
LN 0097            IF(YIN .GE. 0.0 .AND. YIN .LE. FLTN) GO TO 210
LN 0098      C    INTERSECT Y=0
LN 0099            YIN=0.
LN 0100            XIN=X0-Y0/SLOPE
LN 0101            IF(XIN .GE. 0.0 .AND. XIN .LE. FLTN) GO TO 210
LN 0102            GO TO 500
LN 0103        210 CONTINUE
LN 0104            XP=XIN+STEPSZ*DXIN
LN 0105            YP=YIN+STEPSZ*DYIN
LN 0106            GO TO 80
LN 0107      C
LN 0108      C
LN 0109      C    READY TO TRACE
LN 0110      C
LN 0111         80 CONTINUE
LN 0112            F5(1)=XIN
LN 0113            F5(2)=YIN
LN 0114            F5(3)=-DXIN
LN 0115            F5(4)=-DYIN
LN 0116            F5(5)=STEPSZ
LN 0117            F5(6)=XP
LN 0118            F5(7)=YP
LN 0119            FDX=F5(3)
LN 0120            FDY=F5(4)
LN 0121            CALL RTRACE(F5,IDUMMY,NUMB,XOUT,YOUT,LIST,WEIGHT,DXOUT,DYOUT,N)
LN 0122            LJ=0
LN 0123            RETURN
LN 0124      C
LN 0125      C
LN 0126      C    MISSED REGION500
LN 0127        500 CONTINUE
LN 0128            NUMB=0
LN 0129            LJ=1
LN 0130            RETURN
LN 0131            END
```

USASI FORTRAN DIAGNOSTIC RESULTS FOR PTHFNDR

NO ERRORS

THE FOLLOWING ARE COMMON BLOCK NAMES OR NAMES NOT ASSIGNED STORAGE

LSD

```
LN 0001         SUBROUTINE GETIP(LIST,PIXEL,NUMB)
LN 0002   C
LN 0003   C        M. TANAKA, MAYO CLINIC       JANUARY 1978
LN 0004   C        THIS IS TO EXPRESS IN TERM OF REFRACTIVE INDEX
LN 0005   C
LN 0006         COMMON /LSD/ IPICT(4096),NUMANG,NUMPROJ,PI,VW,IPIXEL(4096),
LN 0007        $KOUNT(4096)
LN 0008         COMMON /10/ MAPATT(4096),INTEALFA(4096),MRADIUS(4096)
LN 0009         DIMENSION LIST(1)
LN 0010         DIMENSION PIXEL(1)
LN 0011         DO 100 I=1,NUMB,1
LN 0012         J=LIST(I)+1
LN 0013         PIXEL(I)=VW/FLOAT(IPIXEL(J))
LN 0014     100 CONTINUE
LN 0015         RETURN
LN 0016         END
```

USASI FORTRAN DIAGNOSTIC RESULTS FOR GETIP

NO ERRORS

THE FOLLOWING ARE COMMON BLOCK NAMES OR NAMES NOT ASSIGNED STORAGE

LSD

```
LN 0001         SUBROUTINE DEFLIST(ISUB,N,LIST)
LN 0002   C     * * * * * * * * * ** * * * * * * * * * * * * * * * * * *
LN 0003   C                                                              *
LN 0004   C     PURPOSE-- TO DEFINE THE SUBSCRIPT OF CERTAIN PIXELS USED FOR  *
LN 0005   C               SPECIFIC SUBPROGRAM.                           *
LN 0006   C     AUTHOR-- MITSUO TANAKA, MAYO CLINIC                      *
LN 0007   C     DATE WRITTEN-- SEPTEMBER 16, 1975                        *
LN 0008   C                                                              *
LN 0009   C     * * * * * * * * * * * * * * * * * * * * * * * * * * * * *
LN 0010   C
LN 0011   C
LN 0012   C
LN 0013         DIMENSION LIST(16)
LN 0014   C
LN 0015         LIST(1)=ISUB-N-1
LN 0016         LIST(2)=ISUB-N
LN 0017         LIST(3)=ISUB-N+1
LN 0018         LIST(4)=ISUB-N+2
LN 0019         LIST(5)=ISUB-1
LN 0020         LIST(6)=ISUB
LN 0021         LIST(7)=ISUB+1
LN 0022         LIST(8)=ISUB+2
LN 0023         LIST(9)=ISUB+N-1
LN 0024         LIST(10)=ISUB+N
LN 0025         LIST(11)=ISUB+N+1
LN 0026         LIST(12)=ISUB+N+2
LN 0027         LIST(13)=ISUB+2*N-1
LN 0028         LIST(14)=ISUB+2*N
LN 0029         LIST(15)=ISUB+2*N+1
LN 0030         LIST(16)=ISUB+2*N+2
LN 0031   C
LN 0032         RETURN
LN 0033         END
```

USASI FORTRAN DIAGNOSTIC RESULTS FOR DEFLIST

NO ERRORS

```
LN 0001         SUBROUTINE FINDMAX(IPICT,JMAX,JMIN,N)
LN 0002   C
LN 0003   C        M. TANAKA, MAYO CLINIC       JANUARY 1978
LN 0004   C
LN 0005         DIMENSION IPICT(1)
LN 0006         NSQ=N*N
LN 0007   C
LN 0008   C     FIND ITS MAXIMUM AND MINIMUM
LN 0009         JMAX=IPICT(1)
LN 0010         JMIN=IPICT(1)
LN 0011         DO 105 K=2,NSQ,1
LN 0012         IF(IPICT(K) .GE. JMAX) JMAX=IPICT(K)
LN 0013         IF(IPICT(K) .LT. JMIN) JMIN=IPICT(K)
LN 0014     105 CONTINUE
LN 0015         WRITE(61,131) JMAX,JMIN
```

```
LN 0016        131 FORMAT(1X,*JMAX, AND JMIN ARE*,2I15)
LN 0017            RETURN
LN 0018            END
```

USASI FORTRAN DIAGNOSTIC RESULTS FOR FINDMAX

NO ERRORS

```
LN 0001            SUBROUTINE WRITER(V,N,JA,IFILE,MAX,MIN)
LN 0002        C
LN 0003        C      M. TANAKA, MAYO CLINIC       JANUARY 1978
LN 0004        C
LN 0005            INTEGER V(1)
LN 0006            DIMENSION IHEAD(10)
LN 0007            NSQ=N*N
LN 0008        C   LU=2 IS THE OUTPUT DSI
LN 0009            LU=2
LN 0010            IHEAD(1)=IFILE+JA
LN 0011            IHEAD(2)=N
LN 0012            IHEAD(3)=MAX
LN 0013            IHEAD(4)=MIN
LN 0014            IHEAD(5)=0
LN 0015            IHEAD(6)=0
LN 0016            IHEAD(7)=0
LN 0017            IHEAD(8)=0
LN 0018            IHEAD(9)=0
LN 0019            IHEAD(10)=0
LN 0020        C
LN 0021            BUFFER OUT(LU,1) (IHEAD(1),IHEAD(10))
LN 0022         69 ISTAT=IFUNIT(LU)+2
LN 0023            GO TO(50,20,50,499,499,499,69,499),ISTAT
LN 0024         20 CONTINUE
LN 0025            BUFFER OUT(LU,1) (V(1),V(NSQ))
LN 0026        119 ISTAT=IFUNIT(LU)+2
LN 0027            GO TO(50,40,50,499,499,499,119,499),ISTAT
LN 0028         40 CONTINUE
LN 0029            ENDFILE LU
LN 0030            ENDFILE LU
LN 0031            BACKSPACE LU
LN 0032            RETURN
LN 0033        C
LN 0034         50 CONTINUE
LN 0035            WRITE(61,60)
LN 0036         60 FORMAT(1X,*CAN NOT WRITE*)
LN 0037            STOP
LN 0038        499 WRITE(61,498)
LN 0039        498 FORMAT(1X,*UNRECOVERABLE ERROR*)
LN 0040            STOP
LN 0041            END
```

USASI FORTRAN DIAGNOSTIC RESULTS FOR WRITER

NO ERRORS

```
LN 0001            SUBROUTINE RTRACE(F5,IXY,IPT,X,Y,IP,PV,DXLAST,DYLAST,N)
LN 0002        C                                                          *
LN 0003        C   PURPOSE-- TO TRACE RAYS AND TO FIND THE WEIGHT OF RAY IN EACH *
LN 0004        C       PIXEL.                                             *
LN 0005        C   AUTHOR-- MITSUO TANAKA                                 *
LN 0006        C   DATE WRITTEN-- DECEMBER, 1975                          *
LN 0007        C                                                          *
LN 0008        C   * * * * * * * * * * * * * * * * * * * * * * * * * * * *
LN 0009            COMMON /LSD/ IPICT(4096),NUMANG,NUMPROJ,PI,VW,IPIXEL(4096),
LN 0010           $KOUNT(4096)
LN 0011            COMMON /10/ MAPATT(4096),INTEALFA(4096),MRADIUS(4096)
LN 0012        C
LN 0013            DIMENSION F5(1),IP(1),PV(1)
LN 0014        C
LN 0015        C   ****************************************************************
LN 0016        C                                                          *
LN 0017        C                                                          *
LN 0018        C    INPUT ARRAY F5                                        *
LN 0019        C   F5(1)--RX= X COORDINATE OF THE STARTING POINT.         *
LN 0020        C   F5(2)-- RY-- Y COORDINATE OF THE STARTING POINT.       *
LN 0021        C   F5(3)-- DX-- X COMPONENT OF THE UNIT TANGENT AT (X0,Y0)
LN 0022        C   F5(4)-- DY-- Y COMPONENT OF THE UNIT TANGENT AT THE POINT (X0,Y0)
LN 0023        C   F5(5)-- DS-- STEP SIZE ALONG THE ARC.
LN 0024        C
LN 0025        C
```

```
LN 0026   C      OUTPUT PARAMETERS
LN 0027   C      IXY-- NUMBER OF ENTRIES IN ARRAYS X OR Y
LN 0028   C      IPT-- NUMBER OF PIXEL A RAY GOES THROUGH
LN 0029   C      IP-- A FUNCTION TO DEFINE THE INDEX
LN 0030   C      PV-- A FUNCTION TO DEFINE THE WEIGHT FOR EACH PIXEL      P
LN 0031   C      TOTALWT-- SUM OF PV(IPT) FOR IPT=1,NUMB
LN 0032   C
LN 0033   C
LN 0034   C      THIS SUBROUTINE NEEDS A SUBROUTINE EVAL(RX,RY,GNX,GNY,VN)
LN 0035   C      TO BE SUPPLIED BY THE USER WHERE
LN 0036   C      RX-- AN INPUT PARAMETERS X COORDINATE OF THE POINT
LN 0037   C      RY-- AN INPUT PARAMETERS Y COORDINATE OF THE POINT
LN 0038   C      GNX-- AN OUTPUT PARAMETER, THE PARTIAL DERIVATIVE OF N(X,Y)
LN 0039   C      WITH RESPECT TO X EVALUATED AT (RX,RY)
LN 0040   C      GNY-- DEFINED IN THE SAME WAY
LN 0041   C
LN 0042   C      VN-- VALUE OF THE FUNCTION N(X,Y) AT (RX,RY)
LN 0043   C
LN 0044   C
LN 0045   C      THE AREA OF INTEREST IS BOUNDED BY THE FOLLOWING EQUATIONS
LN 0046   C      X=64, X=0, Y=64, Y=0
LN 0047   C
LN 0048   C
LN 0049   C      RTRACE TRACES THE PATH OF A RAY UNTIL THE RAY CROSSES THE
LN 0050   C      BOUNDARY
LN 0051   C
LN 0052   C      WHEN THE RAY CROSSES THE BOUNDARY THE CONTROL IS RETURNED TO THE
LN 0053   C      CALLER
LN 0054   C
LN 0055   C
LN 0056   C  * * * * * * * * * * * * * * * * * * * * * * * * * * * * * * * * *
LN 0057   C
LN 0058   C
LN 0059   C      XUP=64 $ YUP=64 $ XLO=0 $ YLO=0
LN 0060   C
LN 0061          DATA MAXPT/150/
LN 0062   C
LN 0063          XUP=FLOAT(N)
LN 0064          YUP=FLOAT(N)
LN 0065          XLO=0.0
LN 0066          YLO=0.0
LN 0067   C
LN 0068   C      LET RXP1 BE X-COMPONENT OF THE PREVIOUS POINT
LN 0069   C      LET RXP2 BE THE X-COMPONENT OF THE PREVIOUS POINT OF RXP1
LN 0070   C      RYP1 AND RYP2 ARE DEFINED LIKEWISE.
LN 0071   C
LN 0072   C
LN 0073          RXP1=F5(1)
LN 0074          RYP1=F5(2)
LN 0075          DX=F5(3)
LN 0076          DY=F5(4)
LN 0077          DS=F5(5)
LN 0078          RXP2=F5(6)
LN 0079          RYP2=F5(7)
LN 0080          IPT=0
LN 0081   C
LN 0082   C
LN 0083          SL=0.
LN 0084          TOTALWT=0.0
LN 0085   C
LN 0086          IF(RYP1 .EQ. YUP) RYP1=RYP1-0.001
LN 0087          IF(RXP1 .EQ. XUP) RXP1=RXP1-0.001
LN 0088   C
LN 0089   C
LN 0090        5 IPT=IPT+1
LN 0091          IX=IFIX(RXP1)
LN 0092          IY=IFIX(RYP1)
LN 0093          IP(IPT)=IY*N+IX
LN 0094   C
LN 0095   C
LN 0096       10 CALL EVAL(RXP1,RYP1,GNX,GNY,VN,N)
LN 0097          DDXDS=1.0/(2.0*VN)*(GNX-(GNX*DX+GNY*DY)*DX)*DS
LN 0098          DDYDS=1.0/(2.0*VN)*(GNY-(GNX*DX+GNY*DY)*DY)*DS
LN 0099          TX=DDXDS+DX
LN 0100          TY=DDYDS+DY
LN 0101          TT=SQRT(TX*TX+TY*TY)
LN 0102          RX=RXP1+(TX/TT)*DS
LN 0103          RY=RYP1+(TY/TT)*DS
LN 0104   C
LN 0105   C
LN 0106          IF(IPT .EQ. MAXPT) GO TO 500
LN 0107          IF(RX .GT. XUP) GO TO 500
LN 0108          IF(RX .LT. XLO) GO TO 500
LN 0109          IF(RY .GT. YUP) GO TO 500
LN 0110          IF(RY .LT. YLO) GO TO 500
```

```
LN 0111            GO TO 85
LN 0112      C
LN 0113      C     TO CHECK IF THE NEW POINT IS STILL IN THE SAME PIXEL OR NOT.
LN 0114      C     WE ALSO NEED TO FIND THE WEIGHT(LENTH OF PATH OF RAY IN EACH PIXEL)
LN 0115      C
LN 0116         85 IF(RY.LT.FLOAT(IY  )) GO TO 20
LN 0117            IF(RY.GT.FLOAT(IY+1)) GO TO 20
LN 0118            IF(RX.GT.FLOAT(IX+1)) GO TO 20
LN 0119            IF(RX.LT.FLOAT(IX  )) GO TO 20
LN 0120            Z=DS
LN 0121            NCHECK=2
LN 0122            GO TO 777
LN 0123      C
LN 0124      C
LN 0125         20 Z=DS
LN 0126            SL=SL+Z
LN 0127      C
LN 0128            PV(IPT)=SL
LN 0129      C
LN 0130      C
LN 0131            SL=0.0
LN 0132            NCHECK=1
LN 0133            GO TO 183
LN 0134      C
LN 0135      C
LN 0136      C
LN 0137        777 SL=SL+Z
LN 0138      C
LN 0139      C     HERE, THE TANGENT VECTOR AT THE POINT (RX,RY) IS APPROXIMATED AS FOLLOWS.
LN 0140      C
LN 0141        183 ANORM1=SQRT((RX-RXP2)*(RX-RXP2)+(RY-RYP2)*(RY-RYP2))
LN 0142            AINPRO1=2.0*((RXP1-RXP2)*(RX-RXP2)+(RYP1-RYP2)*(RY-RYP2))
LN 0143            DX=(1.0/DS)*(3.0*RX-2.0*RXP1-RXP2)-3.0*(RX-RXP2)*ANORM1/AINPRO1
LN 0144            DY=(1.0/DS)*(3.0*RY-2.0*RYP1-RYP2)-3.0*(RY-RYP2)*ANORM1/AINPRO1
LN 0145      C
LN 0146      C     DONT NEED ARRAY OF X, Y COORDS
LN 0147      C
LN 0148            X=RX
LN 0149            Y=RY
LN 0150      C
LN 0151      C     NOW, LET
LN 0152            RXP2=RXP1
LN 0153            RYP2=RYP1
LN 0154            RXP1=RX
LN 0155            RYP1=RY
LN 0156            GO TO (5,10), NCHECK
LN 0157      C
LN 0158      C
LN 0159      C
LN 0160        500 IF(IPT - MAXPT) 610,600,600
LN 0161        600 WRITE(61,620) IPT,X,Y
LN 0162        620 FORMAT(//,10X,*SOMETHING IS WRONG WITH THIS RAY. IPT=*,I4,5X,*XOUT
LN 0163           $=*,F10.3,*YOUT=*,F10.3)
LN 0164            STOP
LN 0165        610 PV(IPT)=SL
LN 0166      C
LN 0167            X=RX
LN 0168            Y=RY
LN 0169      C
LN 0170      C
LN 0171      C
LN 0172            DXLAST=DX
LN 0173            DYLAST=DY
LN 0174            RETURN
LN 0175            END
```

USASI FORTRAN DIAGNOSTIC RESULTS FOR RTRACE

NO ERRORS

THE FOLLOWING ARE COMMON BLOCK NAMES OR NAMES NOT ASSIGNED STORAGE

LSD

```
LN 0001            SUBROUTINE EVAL(X,Y,DFDX,DFDY,FOFXY,N)
LN 0002      C     * * * * * * * * * * * * * * * * * * * * * * * * * * * * * *
LN 0003      C
LN 0004      C     PURPOSE-- TO INTERPOLATE THE GRADIENT WITH RESPECT TO X AND Y
LN 0005      C     AUTHOR-- MITSUO TANAKA, MAYO CLINIC
LN 0006      C     DATE WRITTEN-- SEPTEMBER 16, 1975
LN 0007      C
LN 0008      C     * * * * * * * * * * * * * * * * * * * * * * * * * * * * * *
```

```
LN 0009    C
LN 0010    C
LN 0011    C
LN 0012    C   THIS ROUTINE EVALUATES THE FUNCTION (PICT) AT X,Y.  IT RETURNS
LN 0013    C   F(X,Y), DF/DX (PARTIAL DERIVATIVE), AND DF/DY (PARTIAL).
LN 0014    C
LN 0015    C   F(X,Y) IS THE VALUE OF PICT IN PIXEL DENOTED BY X,Y.
LN 0016    C
LN 0017    C
LN 0018    C
LN 0019            COMMON /LSD/ IPICT(4096),NUMANG,NUMPROJ,PI,VW,IPIXEL(4096),
LN 0020          SKOUNT(4096)
LN 0021            COMMON /10/ MAPATT(4096),INTEALFA(4096),MRADIUS(4096)
LN 0022    C
LN 0023            DIMENSION PIXEL(16),LIST(16)
LN 0024    C
LN 0025    C
LN 0026            IX=IFIX(X)
LN 0027            IY=IFIX(Y)
LN 0028    C
LN 0029    C   CHECK FOR OUT OF BOUND
LN 0030            IF(IY .LT. 0 .OR. IY .GT. N) GO TO 60
LN 0031            IF(IX .LT. 0 .OR. IX .GT. N) GO TO 60
LN 0032            IF(IX .EQ. N) IX=N-1
LN 0033            IF(IY .EQ. N) IY=N-1
LN 0034    C   SUBSCRIPT FOR THE PIXEL
LN 0035            ISUB=IY*N+IX
LN 0036    C
LN 0037            CALL DEFLIST(ISUB,N,LIST)
LN 0038    C
LN 0039    C   SPECIAL CASES
LN 0040            IF(IX .EQ. 0) GO TO 111
LN 0041            IF(IY .EQ. 0) GO TO 222
LN 0042            IF(IX .EQ. N-1) GO TO 333
LN 0043            IF(IX .EQ. N-2) GO TO 444
LN 0044            IF(IY .EQ. N-1) GO TO 555
LN 0045            IF(IY .EQ. N-2) GO TO 666
LN 0046    C
LN 0047    C
LN 0048    C   CASE--IX=0
LN 0049        111 CONTINUE
LN 0050            IF(IY .GE. 1 .AND. IY .LT. N-2) GO TO 112
LN 0051            GO TO 113
LN 0052        112 DO 118 LI=1,13,4
LN 0053            LIST(LI)=LIST(LI+1)
LN 0054        118 CONTINUE
LN 0055            GO TO 999
LN 0056    C
LN 0057        113 IF(IY) 115,114,115
LN 0058        114 LIST(1)=LIST(6)
LN 0059            LIST(2)=LIST(6)
LN 0060            LIST(3)=LIST(7)
LN 0061            LIST(4)=LIST(8)
LN 0062            LIST(5)=LIST(6)
LN 0063            LIST(9)=LIST(10)
LN 0064            LIST(13)=LIST(14)
LN 0065            GO TO 999
LN 0066    C
LN 0067        115 IF(IY - (N-2)) 117,116,117
LN 0068        116 LIST(1)=LIST(2)
LN 0069            LIST(5)=LIST(6)
LN 0070            LIST(9)=LIST(10)
LN 0071            LIST(13)=LIST(10)
LN 0072            LIST(14)=LIST(10)
LN 0073            LIST(15)=LIST(11)
LN 0074            LIST(16)=LIST(12)
LN 0075            GO TO 999
LN 0076    C
LN 0077        117 LIST(1)=LIST(2)
LN 0078            LIST(5)=LIST(2)
LN 0079            LIST(6)=LIST(2)
LN 0080            LIST(7)=LIST(3)
LN 0081            LIST(8)=LIST(4)
LN 0082            LIST(9)=LIST(6)
LN 0083            LIST(10)=LIST(6)
LN 0084            LIST(11)=LIST(7)
LN 0085            LIST(12)=LIST(8)
LN 0086            LIST(13)=LIST(6)
LN 0087            LIST(14)=LIST(6)
LN 0088            LIST(15)=LIST(7)
LN 0089            LIST(16)=LIST(8)
LN 0090            GO TO 999
LN 0091    C
LN 0092    C
LN 0093    C   CASE--IY=0
```

```
LN 0094      222 CONTINUE
LN 0095          IF(IX .GE. 1 .AND. IX .LT. N-2) GO TO 211
LN 0096          GO TO 212
LN 0097      211 DO 213 I=1,4,1
LN 0098          LIST(I)=LIST(I+4)
LN 0099      213 CONTINUE
LN 0100          GO TO 999
LN 0101    C
LN 0102      212 IF(IX) 214,114,214
LN 0103      214 IF(IX - (N-2)) 216,215,216
LN 0104      215 LIST(1)=LIST(5)
LN 0105          LIST(2)=LIST(6)
LN 0106          LIST(3)=LIST(7)
LN 0107          LIST(4)=LIST(7)
LN 0108          LIST(8)=LIST(7)
LN 0109          LIST(12)=LIST(11)
LN 0110          LIST(16)=LIST(15)
LN 0111          GO TO 999
LN 0112    C
LN 0113      216 LIST(1)=LIST(5)
LN 0114          LIST(2)=LIST(5)
LN 0115          LIST(3)=LIST(5)
LN 0116          LIST(4)=LIST(5)
LN 0117          LIST(6)=LIST(5)
LN 0118          LIST(7)=LIST(6)
LN 0119          LIST(8)=LIST(6)
LN 0120          LIST(13)=LIST(9)
LN 0121          LIST(11)=LIST(10)
LN 0122          LIST(12)=LIST(10)
LN 0123          LIST(14)=LIST(13)
LN 0124          LIST(15)=LIST(14)
LN 0125          LIST(16)=LIST(14)
LN 0126          GO TO 999
LN 0127    C
LN 0128    C
LN 0129    C    CASE-- IX=N-1
LN 0130      333 CONTINUE
LN 0131          IF(IY .GE. 1 .AND. IY .LT. N-2) GO TO 311
LN 0132          GO TO 312
LN 0133      311 LIST(3)=LIST(2)
LN 0134          LIST(4)=LIST(2)
LN 0135          LIST(7)=LIST(6)
LN 0136          LIST(8)=LIST(6)
LN 0137          LIST(11)=LIST(10)
LN 0138          LIST(12)=LIST(10)
LN 0139          LIST(15)=LIST(14)
LN 0140          LIST(16)=LIST(14)
LN 0141          GO TO 999
LN 0142    C
LN 0143      312 IF(IY) 313,216,313
LN 0144      313 IF(IY - (N-2)) 315,314,315
LN 0145      314 LIST(3)=LIST(2)
LN 0146          LIST(4)=LIST(2)
LN 0147          LIST(7)=LIST(6)
LN 0148          LIST(8)=LIST(6)
LN 0149          LIST(11)=LIST(10)
LN 0150          LIST(12)=LIST(10)
LN 0151          LIST(13)=LIST(9)
LN 0152          LIST(14)=LIST(10)
LN 0153          LIST(15)=LIST(10)
LN 0154          LIST(16)=LIST(10)
LN 0155          GO TO 999
LN 0156    C
LN 0157      315 LIST(3)=LIST(2)
LN 0158          LIST(4)=LIST(2)
LN 0159          DO 316 IJ=5,16,1
LN 0160          LIST(IJ)=LIST(1)
LN 0161      316 CONTINUE
LN 0162          LIST(9)=LIST(5)
LN 0163          LIST(13)=LIST(5)
LN 0164          GO TO 999
LN 0165    C
LN 0166    C
LN 0167    C    CASE-- IX=N-2
LN 0168      444 CONTINUE
LN 0169          IF(IY .GE. 1 .AND. IY .LT. N-2) GO TO 411
LN 0170          GO TO 412
LN 0171      411 DO 413 K=4,16,4
LN 0172          LIST(K)=LIST(K-1)
LN 0173      413 CONTINUE
LN 0174          GO TO 999
LN 0175    C
LN 0176      412 IF(IY) 419,215,419
LN 0177      419 IF(IY - (N-2)) 415,414,415
LN 0178      414 LIST(4)=LIST(3)
```

```
LN 0179            LIST(8)=LIST(7)
LN 0180            LIST(12)=LIST(11)
LN 0181            DO 416 L=13,16,1
LN 0182            LIST(L)=LIST(L-4)
LN 0183        416 CONTINUE
LN 0184            GO TO 999
LN 0185    C
LN 0186        415 LIST(4)=LIST(3)
LN 0187            LIST(5)=LIST(4)
LN 0188            LIST(6)=LIST(2)
LN 0189            LIST(7)=LIST(3)
LN 0190            LIST(8)=LIST(7)
LN 0191            LIST(9)=LIST(5)
LN 0192            LIST(13)=LIST(5)
LN 0193            LIST(10)=LIST(6)
LN 0194            LIST(14)=LIST(6)
LN 0195            LIST(11)=LIST(7)
LN 0196            LIST(15)=LIST(7)
LN 0197            LIST(12)=LIST(7)
LN 0198            LIST(16)=LIST(7)
LN 0199            GO TO 999
LN 0200    C
LN 0201    C
LN 0202    C      CASE-- IY=N-1
LN 0203        555 CONTINUE
LN 0204            IF(IX .GE. 1 .AND. IX .LT.N-2) GO TO 511
LN 0205            GO TO 512
LN 0206        511 LIST(9)=LIST(5)
LN 0207            LIST(13)=LIST(5)
LN 0208            LIST(10)=LIST(6)
LN 0209            LIST(14)=LIST(6)
LN 0210            LIST(11)=LIST(7)
LN 0211            LIST(15)=LIST(7)
LN 0212            LIST(12)=LIST(8)
LN 0213            LIST(16)=LIST(9)
LN 0214            GO TO 999
LN 0215    C
LN 0216        512 IF(IX) 513,117,513
LN 0217        513 IF(IX - (N-2)) 315,415,315
LN 0218    C
LN 0219    C
LN 0220    C      CASE-- IY=N-2
LN 0221        666 CONTINUE
LN 0222            IF(IX .GE. 1 .AND. IX .LT.N-2) GO TO 611
LN 0223            GO TO 612
LN 0224        611 DO 613 IK=13,16,1
LN 0225            LIST(IK)=LIST(IK-4)
LN 0226        613 CONTINUE
LN 0227            GO TO 999
LN 0228    C
LN 0229        612 IF(IX) 619,116,619
LN 0230        619 IF(IX - (N-2)) 314,414,314
LN 0231    C
LN 0232    C
LN 0233        999 CALL GETIP(LIST,PIXEL,16)
LN 0234    C
LN 0235            P=X-FLOAT(IX)
LN 0236            Q=Y-FLOAT(IY)
LN 0237    C
LN 0238    C
LN 0239            DFDX=(1.0-P)*(1.0-Q)/8.0*(2.0*(PIXEL(7)-PIXEL(5))
LN 0240           $+(PIXEL(11)-PIXEL(9))+(PIXEL(3)-PIXEL(1)))
LN 0241           $+P*(1.0-Q)/8.0*(2.0*(PIXEL(8)-PIXEL(6))+(PIXEL(12)-PIXEL(10))
LN 0242           $+(PIXEL(4)-PIXEL(2)))
LN 0243           $+Q*(1.0-P)/8.0*(2.0*(PIXEL(11)-PIXEL(9))+(PIXEL(15)-PIXEL(13))
LN 0244           $+(PIXEL(7)-PIXEL(5)))
LN 0245           $+P*Q/8.0*(2.0*(PIXEL(12)-PIXEL(10))+(PIXEL(16)-PIXEL(14))
LN 0246           $+(PIXEL(8)-PIXEL(6)))
LN 0247    C
LN 0248            DFDY=(1.0-P)*(1.0-Q)/8.0*(2.0*(PIXEL(10)-PIXEL(2))
LN 0249           $+(PIXEL(11)-PIXEL(3))+(PIXEL(9)-PIXEL(1)))
LN 0250           $+P*(1.0-Q)/8.0*(2.0*(PIXEL(11)-PIXEL(3))+(PIXEL(10)-PIXEL(2))
LN 0251           $+(PIXEL(12)-PIXEL(4)))
LN 0252           $+Q*(1.0-P)/8.0*(2.0*(PIXEL(14)-PIXEL(6))+(PIXEL(13)-PIXEL(5))
LN 0253           $+(PIXEL(15)-PIXEL(7)))
LN 0254           $+P*Q/8.0*(2.0*(PIXEL(15)-PIXEL(7))+(PIXEL(14)-PIXEL(6))
LN 0255           $+(PIXEL(16)-PIXEL(8)))
LN 0256    C
LN 0257            FOFXY=PIXEL(6)
LN 0258            GO TO 100
LN 0259    C
LN 0260    C
LN 0261    C      GOT A PROBLEM
LN 0262         60 CONTINUE
LN 0263            PRINT 70,X,IX,Y,IY
LN 0264         70 FORMAT(* X OR Y OUT OF RANGE, X, IX, Y, IY*,2(F7.2,I8))
```

```
LN 0265           STOP
LN 0266    C
LN 0267    C
LN 0268       100 CONTINUE
LN 0269           RETURN
LN 0270           END
```

USASI FORTRAN DIAGNOSTIC RESULTS FOR EVAL

NO ERRORS

THE FOLLOWING ARE COMMON BLOCK NAMES OR NAMES NOT ASSIGNED STORAGE

LSD

```
LN 0001           SUBROUTINE STRAIGHT(TX,TY,RA,R,XCEN,YCEN,SCONST,N)
LN 0002    C
LN 0003    C     M. TANAKA, MAYO CLINIC        JANUARY 1978
LN 0004    C
LN 0005           COMMON /LSD/ IPICT(4096),NUMANG,NUMPROJ,PI,VW,IPIXEL(4096),
LN 0006          *KOUNT(4096)
LN 0007           COMMON /ID/ MAPATT(4096),INTEALFA(4096),MRADIUS(4096)
LN 0008           NH=N/2
LN 0009           NSQ=N*N
LN 0010    C
LN 0011           DO 150 ID=1,NSQ,1
LN 0012    C      FIND THE COORDINATE OF THE CNTER OF ID, THE PIXEL
LN 0013           INDEX=ID-1
LN 0014           IY=INDEX/N
LN 0015           IX=INDEX-N*IY
LN 0016           EY=FLOAT(IY-NH)
LN 0017           EX=FLOAT(IX-NH)
LN 0018           XA=XCEN+EX*SCONST
LN 0019           YA=YCEN+EY*SCONST
LN 0020           IF(TX .EQ. XA) XA=XA+0.0001
LN 0021           AM1=(TY-YA)/(TX-XA)
LN 0022           B1=YA-AM1*XA
LN 0023           CALL DECIDE(XA,YA,AM1,B1,RA,X1,Y1,X2,Y2,ICHECK)
LN 0024           DIST=SQRT((TX-XA)*(TX-XA)+(TY-YA)*(TY-YA))
LN 0025           IF(ICHECK)110,110,120
LN 0026       110 MRADIUS(ID)=IFIX(1000.0*DIST)
LN 0027           INTEALFA(ID)=0
LN 0028           GO TO 150
LN 0029       120 MRADIUS(ID)=IFIX(1000.0*DIST)
LN 0030           DIS=SQRT((TX-X2)*(TX-X2)+(TY-Y2)*(TY-Y2))
LN 0031           IF(DIST .GT. DIS) GO TO 170
LN 0032           DA1=SQRT((X1-XA)*(X1-XA)+(Y1-YA)*(Y1-YA))
LN 0033           INTEALFA(ID)=IFIX(DA1*1000.0)
LN 0034           GO TO 150
LN 0035       170 DA2=SQRT((X1-X2)*(X1-X2)+(Y1-Y2)*(Y1-Y2))
LN 0036           INTEALFA(ID)=IFIX(DA2*1000.0)
LN 0037       150 CONTINUE
LN 0038           RETURN
LN 0039           END
```

USASI FORTRAN DIAGNOSTIC RESULTS FOR STRAIGHT

NO ERRORS

THE FOLLOWING ARE COMMON BLOCK NAMES OR NAMES NOT ASSIGNED STORAGE

LSD

```
LN 0001           SUBROUTINE DECIDE(X0,Y0,AM1,B1,R,X1,Y1,X2,Y2,ICHECK)
LN 0002           P1=AM1*AM1*B1*B1-(1.0+AM1*AM1)*(B1*B1-R*R)
LN 0003           IF(P1) 110,110,120
LN 0004       110 ICHECK=-1
LN 0005           RETURN
LN 0006       120 ICHECK=1
LN 0007           SQDET=SQRT(P1)
LN 0008           X1Z=(-AM1*B1+SQDET)/(1.0+AM1*AM1)
LN 0009           X2Z=(-AM1*B1-SQDET)/(1.0+AM1*AM1)
LN 0010           Y1Z=AM1*X1Z+B1
LN 0011           Y2Z=AM1*X2Z+B1
LN 0012           IF(X1Z .NE. X2Z) GO TO 200
LN 0013           YD1Z=ABS(Y0-Y1Z)
LN 0014           YD2Z=ABS(Y0-Y2Z)
LN 0015           IF(YD2Z-YD1Z) 210,220,220
LN 0016       220 Y1=Y1Z
```

```
LN 0017            Y2=Y2Z
LN 0018            GO TO 230
LN 0019      210   Y1=Y2Z
LN 0020            Y2=Y1Z
LN 0021      230   CONTINUE
LN 0022            X1=X1Z
LN 0023            X2=X1
LN 0024            RETURN
LN 0025      200   CONTINUE
LN 0026            XD1Z=(X0-X1Z)*(X0-X1Z)+(Y0-Y1Z)*(Y0-Y1Z)
LN 0027            XD2Z=(X0-X2Z)*(X0-X2Z)+(Y0-Y2Z)*(Y0-Y2Z)
LN 0028            IF(XD2Z-XD1Z)310,320,320
LN 0029      320   X1=X1Z
LN 0030            Y1=Y1Z
LN 0031            X2=X2Z
LN 0032            Y2=Y2Z
LN 0033            RETURN
LN 0034      310   X1=X2Z
LN 0035            Y1=Y2Z
LN 0036            X2=X1Z
LN 0037            Y2=Y1Z
LN 0038            RETURN
LN 0039            END

USASI FORTRAN DIAGNOSTIC RESULTS FOR DECIDE

NO ERRORS

ASCII LISTING PRODUCED BY LISTA      02/02/0  00 00 00
    1  C       CONVOLUTION-TYPE METHOD FOR DIVERGENT DATA
    2  C
    3  C       BASED ON
    4  C           CONVOLUTION RECONSTRUCTION TECHNIQUES FOR DIVERGENT BEAMS
    5  C             G  T  HERMAN, A  V  LAKSHMINARAYAN AND A  NAPARSTEK
    6  C           COMPUTERS IN BIOLOGY AND MEDICINE
    7  C           TO APPEAR
    8  C
    9  C       WRITTEN BY G. T. HERMAN, MARCH 1975
   10  C       REVISED FOR THE CDC3500, MARCH 1976
   11  C       REVISED FOR THE INTERDATA 7/32, JAN  77, P  J  THOMAS
   12  C
   13  C       IFLAG - TRUE IF LINEAR INTERPOLATION IS USED,
   14  C                    ELSE USE NEAREST NEIGHBOR
   15  C       MISSP - EVERY MISSP TH PROJECTION IS USED
   16  C       NCONP - NUMBER OF RAYS ON ONE SIDE USED IN CONVOLVING
   17  C                    INCLUDING THOSE WHICH ARE WEIGHTED ZERO
   18  C                    IN THE CONVOLUTION
   19  C       WCONV - WEIGHT ASSIGNED TO MIDDLE RAY IF DATA IS TO BE SMOOTHED
   20  C                    OVER THREE NEIGHBORING RAYS
   21  C       IF WCONV .LT. 0 PROJECTIONS WILL BE FILTERED BY REPLACING EACH
   22  C       POINT BY THE MEDIAN OF ITSELF AND ITS TWO NEAREST NEIGHBORS.  THIS
   23  C       TENDS TO CANCEL OUT SINGLE POINT GLITCHES
   24  C           METHOD - IF 0, ACCURATE BACKPROJECTION IS USED
   25  C                    IF 1, WEIGHT IN BACKPROJECTION IS APPROXIMATED
   26  C                    IF -1, BOTH WEIGHT AND RAY NUMBER ARE APPROXIMATED
   27  C                    (THE LESS ACCURATE METHODS ARE FASTER)
   28  C
   29  C       TAPE FORMAT NCI
   30  C.......
   31  C       DIMENSIONS OF RECONSTRUCTION IMAGE ARE IN (PROFILE DIMENSION OVER
   32  C           RADIUS DIMENSIONS) TIMES CON (USUALLY 1000.)
   33  C.........NEW = 1 FOR NEW TAPE
   34  C             = 0 FOR TAPE WITH OTHER PICTURES
   35  C.......
   36          DIMENSION ID(10), IH(64), IPROJ(512), IRECN(4096), IMFILE(4)
   37          DIMENSION G(512), FJ(512), GM(512), FMOD(512)
   38          INTEGER*4 PRJNUM, AREA, ONE80, ONE81, STATUS
   39          INTEGER*2 PBLK(10), ISTAT, MIDP(512), MIDPM1(512), MIDPP1(512)
   40          EQUIVALENCE (ISTAT,PBLK(2))
   41          EQUIVALENCE(MIDP(1),G(1))
   42          EQUIVALENCE(MIDPM1(1),FJ(1))
   43          EQUIVALENCE(MIDPP1(1),GM(1))
   44          DATA ID/10*0/
   45          DO 46 I=1,64
   46   46     IH(I)=0
   47          IREP=3
   48          MISSP=1
   49          NCI=1
   50  C       LU MAGTAPE IN = 1
   51  C       LU DISC (SINOGRAM) = 4
   52  C       LU DISC OUTPUT (IMAGE) = 2
   53   54     CONTINUE
   54          REWIND
```

```
 55          CALL CLOSE (2,STATUS)
 56          WRITE (5,57)
 57    57    FORMAT (' OUTPUT FILENAME FOR IMAGE?')
 58          READ (5,59) IMFILE
 59    59    FORMAT (A4)
 60          CALL OPENR (IMFILE,2,COM,1,1,STATUS)
 61          IF (STATUS .EQ. 0 .OR. STATUS .EQ. 4) GOTO 76
 62          IF (STATUS .EQ. 2) WRITE (5,71)
 63          IF (STATUS .EQ. 5) WRITE (5,71)
 64          IF (STATUS .EQ. 8) WRITE (5,73)
 65          IF (STATUS .EQ. 10) WRITE (5,74)
 66          IF (STATUS .EQ. 11) WRITE (5,75)
 67          PAUSE
 68          GOTO 54
 69    70    FORMAT (' ILLEGAL FUNCTION ')
 70    71    FORMAT (' VOLUME ERROR ')
 71    73    FORMAT (' SIZE ERROR - NOT ENOUGH SPACE')
 72    74    FORMAT (' TYPE ERROR')
 73    75    FORMAT (' SYNTAX ERROR')
 74    76    CALL OPENW (2,IMFILE,7,0,0,STATUS)
 75          IF (STATUS .NE. 0) WRITE (5,78) STATUS
 76    78    FORMAT (' STATUS= 'I6)
 77          CALL INPUT(' PRJNUM?',8,PRJNUM,REAL)
 78          CALL INPUT(' MISSP?',8,MISSP,REAL)
 79          CALL INPUT(' RCONSZ',10,INT4,RCONSZ)
 80          NELEM=64
 81          CALL INPUT(' FILE?',8,IFILE,REAL)
 82          CALL INPUT(' LINE?',6,LINE,REAL)
 83          CON=1000
 84          CALL INPUT(' MAP? (1=YES, 0=NO)',20,MAP,REAL)
 85  C       CON=NORMALIZATION NUMBER
 86          WRITE (3,89) IFILE,LINE
 87    89    FORMAT(1H1,/' ****RECON FOR FILE'I6' LINE'I6' ****')
 88          CALL INPUT(' IS FILE ON DISK? (NO=0,YES=1)',30,INDISK,REAL)
 89          INDISK=INDISK+1
 90          GOTO(93,118),INDISK
 91    93    CONTINUE
 92    94       CALL SYSIO(PBLK,Y'84',1,IH(1),1,IRAND)
 93             READ(1,END=97)IRECN
 94             GOTO 94
 95    97       READ (1,END=102)IH
 96             WRITE(5,99) IH(1)
 97    99       FORMAT (X16)
 98             IF (IFILE .EQ. IH(1)) GOTO 105
 99             GOTO 94
100   102       WRITE(5,103)
101   103       FORMAT(' END OF TAPE')
102             PAUSE
103   105       CONTINUE
104  C       WRITE HEADER ON DISC
105          WRITE(4)IH
106  C       PUT SINOGRAM ON DISC
107          NSP3=IH(6)+3
108  $TRCE
109          IEND=IH(4)*IH(5)
110  $NTRE
111          DO 117 I=1,IEND
112  C          SKIP PAST EOF AND READ LINE PROFILE FROM TAPE
113   113       READ(1,END=113)IRECN
114             DO 115 K=1,512
115   115       IF (IRECN(K) .LT. 0) IRECN(K)=IAND(IRECN(K),Y'7FFF')
116  C          WRITE LINE PROFILE ON DISK
117   117       WRITE(4)IRECN
118   118 CONTINUE
119  C       READ HEADER FROM DISC
120          REWIND 4
121          READ(4)IH
122          WRITE(3,123) IH
123   123   FORMAT (1X,10I12)
124          IFILE=IH(1)
125          NRAYS=IH(6)
126          STOD=IH(2)/10.0
127  C       RADIUS=IH(3)/10.0
128          RADIUS=IH(3)
129          PI=4.*ATAN(1.)
130          NRAYM1=NRAYS-1
131          FAN=NRAYM1*PI/2400
132  C       RCONSZ=SIN(FAN)*RADIUS*2
133          PINC=0.0
134          PIXSIZ=RCONSZ/NELEM
135          AREA=NELEM*NELEM
136          NCONR=NRAYS
137          WRITE(3,138)
138   138   FORMAT(' PRJNUM    NRAYS    STOD    RADIUS    NCONR
139         1    PIXSIZE    RCONSZ    NELEM    FILE '//)
```

```
140         WRITE(3,142)PRJNUM,NRAYS,STOD,RADIUS,NCONR,PIXSIZ,
141        1 RCONSZ,NELEM,IFILE
142     142 FORMAT(1X,I5,I10,2F10.2,I10,2F10.2,2I10)
143         GO TO 144
144     144 CONTINUE
145         TWOPI=2.*PI
146         DELTA=TWOPI/PRJNUM
147         IFLAG=1
148         MIDRAY=(NRAYS+1)/2
149         MIDQ=MIDRAY
150         LIMUP=NRAYS
151         WCONW=(1.0-WCONV)/2.0
152         JLO=1
153         JHI=NRAYS
154         MDRYM1=MIDRAY-1
155         MQLO=1
156         MQHI=MDRYM1
157         ALFA=(IH(60)/100.)*(PI/180.)
158         ALFASQ=ALFA*ALFA
159         A=ALFA*RADIUS
160         MIDJ=MIDRAY
161         FJ(MIDJ)=A
162 C
163 C       FILTER TO REMOVE ISOLATED BAD POINTS
164 C       1. LOOK FOR RAPID CHANGE IN LINE PROFILE (>10-7 SEC)
165 C       2. IF RAPID CHANGE, LOOK FOR REVERSAL ON NEXT POINT
166 C       3. IF 1 AND 2 ARE TRUE, REPLACE POINT WITH MEAN OF NEIGHBORS
167 C
168         IBADPT=0
169         DO 187 I=1,PRJNUM
170     168     READ(4) IPROJ
171             IF (IPROJ(2).NE.LINE) GOTO 168
172             P1=IPROJ(3)
173             P2=IPROJ(4)
174             P3=IPROJ(5)
175             DO 184 J=5,NRAYM1
176                 P1=P2
177                 P2=P3
178                 P3=IPROJ(J+1)
179                 DIF1=(P2-P1)*(P2-P1)
180                 IF (DIF1.LT.100) GOTO 184
181                 DIF2=(P3-P1)*(P3-P1)
182                 IF (DIF1.LT.DIF2) GOTO 184
183                 IPROJ(J)=(P1+P3)/2.
184                 IBADPT=IBADPT+1
185     184     CONTINUE
186             CALL BACKSP(4,ISTAT)
187             WRITE(4) IPROJ
188     187 CONTINUE
189         REWIND 4
190         WRITE(3,190) IBADPT
191     190 FORMAT(' ',I5,' BAD POINTS')
192 C
193 C       TEST FOR SMOOTHNESS OF PROJECTION, SWEEP OF ROTATION
194 C       BY COMPARING OPPOSING VIEWS. A ROUGH MEASURE OF SMOOTHNESS IS THE
195 C       ROOT MEAN SQUARE DIFFERENCE, AMPLITUDE OF DIFFERENCES
196 C
197 C       READ HEADER
198         READ(4) IH
199         ONE80=PRJNUM/2
200         DO 204 I=1,ONE80
201     198     READ(4) IPROJ
202             IF (IPROJ(2).NE.LINE) GOTO 198
203             MIDPM1(I)=IPROJ(MIDRAY-1)
204             MIDP(I)=IPROJ(MIDRAY)
205             MIDPP1(I)=IPROJ(MIDRAY+1)
206     204 CONTINUE
207         ONE81=ONE80+1
208         RMS=0
209         DO 214 I=ONE81,PRJNUM
210             J=I-ONE80
211     207     READ(4) IPROJ
212             IF (IPROJ(2).NE.LINE) GOTO 207
213             IDIF1=IPROJ(MIDRAY-1)-MIDPP1(J)
214             IDIF2=IPROJ(MIDRAY)-MIDP(J)
215             IDIF3=IPROJ(MIDRAY+1)-MIDPM1(J)
216             RMS=RMS+IDIF1*IDIF1+IDIF2*IDIF2+IDIF3*IDIF3
217     214 CONTINUE
218         RMS=SQRT(RMS/(ONE80*3.))
219         WRITE(3,217) RMS
220     217 FORMAT(' ROOT MEAN SQUARE DIFFERENCE OF OPPOSING VIEWS=',F6.1)
221         REWIND 4
222 C       READ HEADER
223         READ(4) IH
224 C
225 C       CONVOLUTING FUNCTION G(M)
```

```
226 C
227 C         WEIGHT ARRAY J(I)
228           DO 230 I=1,MDRYM1
229                 IR=MIDJ + I
230                 IL=MIDJ - I
231                 FJ(IR)=A*COS(FLOAT(I)*ALFA)
232                 FJ(IL)=FJ(IR)
233   230   CONTINUE
234           DO 234 M=1, MDRYM1
235                 N=2*M-1
236                 QM(M)=-1./(2.*(PI*SIN(N*ALFA))**2)
237   234   CONTINUE
238 C
239 C         CONSTANTS NEEDED FOR CONVOLUTION AND BACKPROJECTION
240 C
241           CONCEN=1./(8.*ALFA**2)
242           LIMMID = MIN0(NCONR,MDRYM1)
243           MIDMOD=MIDRAY
244           NMID=(NELEM + 1)/2
245           HALFL = FLOAT(NMID)*PIXSIZ
246           TWODR = 2./RADIUS
247           RSQ=RADIUS*RADIUS
248           WRSQ=DELTA*MISSP
249           W=WRSQ/RSQ
250           WTWODR=W*TWODR
251           FMIDRY = FLOAT(MIDRAY)
252           SWATER=0
253 C
254 C         INITIALIZE BETAS TO BE USED IN CALCULATING WEIGHTS FOR
255 C                     BETA INTERPOLATION
256 C
257 C
258 C         CYCLE                              ONE PROJECTION AT A TIME
259 C
260           
261           DO 259
262   259   IRECL=
263           DO      NP=1,PROJCM,MISSP
264                 THETA=DELTA*(NP-1)
265                 IF (MISSP .LT. 2) GOTO 266
266                 MISSP1=MISSP-1
267                 DO 265 I=1,MISSP1
268   264         READ(4) IPROJ
269                 IF (LINE .NE. IPROJ(2)) GOTO 264
270   265         CONTINUE
271   266         READ(4) IPROJ
272                 IF (LINE .NE. IPROJ(2)) GOTO 266
273                 WATER=(IPROJ(4)+IPROJ(5)+IPROJ(6)+IPROJ(7))/4.
274                 WRITE(5,270)IPROJ(1),IPROJ(2),IPROJ(3),WATER
275   270         FORMAT(' ANGLE'I5' LINE'I3' RANGE'I6' WATER'F8.1)
276                 SWATER=SWATER+WATER
277                 DO 274 I=1,NRAYS
278                     G(I)=10.**(IPROJ(I+3)-WATER)*FJ(I)
279   274         CONTINUE
280 C
281 C         COMPUTE CONVOLVED PROJECTION DATA
282 C
283           P=CONCEN*G(MIDRAY)
284           MQM=0
285           DO 285 NM=1,LIMMID,2
286                 MQM=MQM+1
287                 INP=MIDG+NM
288                 INM=MIDG-NM
289                 P=P+(G(INP)+G(INM))*QM(MQM)
290   285       CONTINUE
291           FMOD(MIDMOD)=P
292 C
293 C         WE HAVE NOW TAKEN CARE OF CENTER RAY
294 C
295           DO 322 M=1,MDRYM1
296                 INR=MIDG+M
297                 PR=CONCEN*G(INR)
298                 INL=MIDG-M
299                 PL=CONCEN*G(INL)
300                 IF (NCONR .EQ. 0) GOTO 317
301                 MQM=0
302                 DO 306 NM=1,NCONR,2
303                     INP=INR+NM
304                     IF (INP .GT. LIMUP) GOTO 308
305                     INM=INR-NM
306                     MQM=MQM+1
307                     PR=PR+(G(INP)+G(INM))*QM(MQM)
308                     INP=INL+NM
309                     INM=INL-NM
310                     PL=PL+(G(INP)+G(INM))*QM(MQM)
```

```
311    306           CONTINUE
312                  GOTO 317
313    308           CONTINUE
314                  DO 316 MM=NM,NCONR,2
315                     MQM=MQM+1
316                     INM=INR-MM
317                     IF (INM LE 0) GOTO 317
318                     PR=PR+G(INM)*QM(MQM)
319                     INP=INL+MM
320                     PL=PL+G(INP)*QM(MQM)
321    316           CONTINUE
322    317           CONTINUE
323                  IN=MIDMOD+M
324                  FMOD(IN)=PR
325                  IN=MIDMOD-M
326                  FMOD(IN)=PL
327    312        CONTINUE
328  C
329  C           CALCULATE PROJECTION INFORMATION
330  C
331              CBETA=SIN(THETA)
332              SBETA=-COS(THETA)
333  C
334  C           CALCULATE BACK-PROJECTION INFORMATION
335  C
336              RCOSI=HALFL*(SBETA-CBETA)
337              RCOSY=PIXSIZ*SBETA
338              RCOSX=PIXSIZ*CBETA
339              RSINI=-HALFL*(SBETA+CBETA)
340              RSINY=RCOSX
341              RSINX=-RCOSY
342              WJRFI=-WTWODR*RSINI
343              WJRFX=-WTWODR*RSINX
344              WJRFY=-WTWODR*RSINY
345              FKJRFI=RCOSI/A
346              FKJRFX=RCOSX/A
347              FKJRFY=RCOSY/A
348              PRINI=RADIUS+RSINI
349  C
350  C           BACK-PROJECTION
351  C
352              K=0
353              DO 372 I=1,NELEM
354                 RCOSI=RCOSI+RCOSY
355                 RCOS=RCOSI
356                 PRINI=PRINI+RSINY
357                 RSIN=PRINI
358                 DO 371 J=1,NELEM
359                    K=K+1
360                    RCOS=RCOS+RCOSX
361                    RSIN=RSIN+RSINX
362                    USQ=RSIN*RSIN+RCOS*RCOS
363                    WJRF=WRSQ/USQ
364                    FRACT = RCOS/RSIN
365                    FRACT=ATAN(FRACT)
366                    FKJRF = FRACT/ALFA
367                    FRYNUM=FKJRF+FMIDRY
368                    MODIT=FRYNUM
369                    MODN=MODIT+1
370                    IF(MODIT.LT.1.OR.MODN.GT.NRAYS)GOTO 371
371                    FRAC=FRYNUM-IFIX(FRYNUM)
372                    VALUE=FMOD(MODIT)
373                    POLATE=VALUE+FRAC*(FMOD(MODN)-VALUE)
374                    IRE=IFIX(WJRF*POLATE*CON)
375                    IRECN(K)=IRECN(K)+IRE
376    371          CONTINUE
377    372       CONTINUE
378    373 CONTINUE
379        AMAX=0
380        AMIN=1E7
381        DO 387 K=1,AREA
382  C
383  C     UNITS NOW ARE CON*NANOSECONDS/CM   ADD TIME FOR WATER
384  C     THEN TAKE RECIPROCAL AND MULTIPLY BY CON*10^7 TO GET M/SEC
385  C
386              AWATER=10.*SWATER*MISSP/PRJNUM
387              TIME=IRECN(K)+AWATER/SPED*CON
388              IRECN(K)=1E7*CON/TIME
389              A=IRECN(K)
390              IF (A GT AMAX) AMAX=A
391              IF (A LT AMIN) AMIN=A
392    387 CONTINUE
393        WRITE(3,389)AMAX,AMIN
394    389 FORMAT(' AMAX',F15.6,'   AMIN',F15.6//)
395        IF (MOP EQ 1) GOTO 395
```

```
396         KK1=KK1+E   (NELEM/2)+1
397         KK2=KK1+NELEM-1
398         WRITE(3,394)(IRECN(KK),KK=KK1,KK2)
399    394  FORMAT(5X,10I10)
400    395  ID(1)=
401         ID(2)=4096
402         ID(3)=
403         ID(4)=
404         WRITE (2) ID
405         DO 403 K=1,NELEM
406         IBEG=
407         IEND=          EM -1
408    403  WRITE (2) (IRECN(I),I=IBEG,IEND)
409         IF (MAX      STOP
410         DO 406
411    406  IRECN(I)=IRECN(I)-1500
412         DO 414
413         IBEG=64
414         IEND=IB
415         IBEG1=IBEG+1
416         IEND1=IEND+1
417         WRITE(3,415)(IRECN(K),K=IBEG,IEND,2)
418         WRITE(3,416)(IRECN(K),K=IBEG1,IEND1,2)
419    414  CONTINUE
420    415  FORMAT(3X,2I4)
421    416  FORMAT(3X,2I4)
422         GOTO 54
423         END
```

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An ultrasound imaging apparatus for reconstructing images of reflection from synthetically focused ultrasound energy, said apparatus comprising:
   means for transmitting ultrasound energy signals;
   means for receiving ultrasound energy signals that have been either reflected by or transmitted through an object being scanned by said apparatus;
   means, electronically connected to said receiving means, for electronically storing said received ultrasound signals;
   means for developing a particular type of waveform for each said stored signal such that when said stored signals are combined so as to reconstruct therefrom an image of reflection, regions of both constructive and destructive interference will occur, said regions improving the point response of said combined signals so as to enhance the resolution of said reconstructed image of reflection;
   means, electronically connected to said storage means, for combining said stored signals so as to reconstruct therefrom said image of reflection corresponding to said scanned object; and
   means for displaying said reconstructed image of reflection.

2. The apparatus of claim 1 wherein said means for developing said particular type of waveform comprises means, electronically connected to said transmitting means, for periodically generating said waveform and thereafter communicating said periodically generated waveforms to said transmitting means so that each ultrasound signal transmitted has the shape of said waveform.

3. The apparatus of claim 2 wherein said waveform generating means comprise:
   means for electronically storing a plurality of digital signals, each said digital signal corresponding to a discrete value on said particular waveform;
   means, electronically connected to said digital storage means, for retrieving and converting each said digital signal into a corresponding analog signal; and
   means for shaping said analog signals so as to develop therefrom said particular waveform.

4. An apparatus for ultrasound imaging as defined in claim 3 further comprising means, electronically connected between said receiving means and said means for combining said received signals, for converting each said received signal to a series of corresponding digital signals.

5. The apparatus of claim 1 wherein said means for developing said particular type of waveform comprises means, electronically connected between said receiving means and said combining means, for transforming each said received ultrasound signal into one or more signals corresponding to said waveform.

6. The apparatus of claim 5 wherein said transforming means comprise:
   means, electronically connected to said receiving means, for converting each said received signal into a series of digital signals;
   means, electronically connected to said converting means, for storing said digital signals;
   means, electronically connected to said digital storage means, for retrieving and multiplying each said digital signal by a predetermined value corresponding to a discrete value on said waveform; and
   means for electronically summing each said retrieved and multiplied digital signal so as to develop therefrom a series of digital signals corresponding to said particular waveform.

7. The apparatus of claim 5 wherein said transforming means comprise:
   means, electronically connected to said receiving means, for converting each said received signal into a series of digital signals;
   means, electronically connected to said converting means, for storing said digital signals;
   means, electronically connected to said converting means, for simultaneously (1) retrieving each said digital signal, (2) multiplying said retrieved digital signal by a predetermined value corresponding to a discrete value on said waveform and (3) converting said multiplied signals back to analog signals;

means for electronically summing each said analog signal so as to develop therefrom said particular waveform;

means, electronically connected to said summing means, for converting each said particular waveform to a series of corresponding digital signals.

8. The apparatus of claim 5 wherein said transforming means comprise:

means, electronically connected to said receiving means, for developing a series of time delays for each said received signal;

means, electronically connected to said delay means, for accessing portions of the received signal during each said time delay;

means, electronically connected to said accessing means, for multiplying each accessed portion of the received signal by a predetermined value corresponding to a discrete value on said particular waveform;

means for summing said multiplied portions of the received signal so as to develop therefrom said particular waveform; and means, electronically connected to said summing means, for converting said waveform to a series of corresponding digital signals.

9. An ultrasound imaging apparatus as defined in claim 1 wherein said transmitting and receiving means comprise:

a ring of transducer arrays adapted to circumscribe the object being scanned, said ring of transducer arrays comprising a plurality of transmitter arrays and receiver arrays, said transmitter arrays being located at different points around said ring of arrays;

means, electronically connected to said transducer arrays, for sequentially triggering said transmitter arrays, thereby propagating semicircular wave fronts of ultrasound energy through said object at said different points around said ring of transducer arrays; and means, connected to said ring of transducer arrays, for commutating said transmitter arrays so as to transmit ultrasound energy from each possible position around said object.

10. An ultrasound imaging apparatus as defined in claim 9 wherein said receiver arrays comprise one or more arrays having a first arcuate length and one or more arrays having a second arcuate length different from said first length so as to enable all sound holes between said receiver arrays to be covered by rotating said ring of arrays to at least a second position, said ultrasound imaging apparatus further comprising means for rotating said ring of arrays to at least a second position.

11. An ultrasound imaging apparatus as defined in claim 1 further comprising:

means, electronically connected to said detecting means, for determining the refractive index for said object and the attenuation coefficient for said object; and means for correcting said reconstructed image of reflection so as to eliminate distortions arising from refraction and attenuation of ultrasound energy through said object, thereby enhancing the resolution for said reconstructed image.

12. An ultrasound imaging apparatus for reconstructing images of reflection from synthetically focused ultrasound energy, said apparatus comprising:

a plurality of transducer arrays for transmitting and receiving ultrasound energy signals;

means, electronically connected to said transducer arrays, for triggering a plurality of said arrays, thereby propagating a series of wave fronts of ultrasound energy through an object being scanned;

an electronic memory circuit for storing said received ultrasound signals;

means for electronically combining said stored signals so as to reconstruct therefrom an image of reflection corresponding to said scanned object;

means for developing a particular type of waveform for each said stored signal such that when said stored signals are combined so as to reconstruct therefrom an image of reflection, all signals corresponding to a given scattering point within said object will (1) constructively interfere within a first region to produce an extreme value for a point in said image of reflection corresponding to said scattering point, and (2) destructively interfere within a second region to produce a value near or at zero for closely situated adjacent points in said image of reflection that do not correspond to said scattering point, thereby enhancing the resolution of said reconstructed image of reflection; and a display screen electronically connected to said combining means for displaying said reconstructed image of reflection.

13. The ultrasound imaging apparatus of claim 12 wherein said transducer arrays comprise:

a plurality of transmitter and receiver arrays configurated as a ring which circumscribes said object, said transmitter arrays being spaced around said ring at a plurality of locations;

means for sequentially triggering said transmitter arrays; and means, connected to said ring of transducer arrays, for commutating said transmitter arrays so as to transmit said ultrasound signals from each possible position around said object.

14. The apparatus of claim 13 wherein said receiver arrays comprise one or more arrays having a first length and one or more arrays having a second length different from said first length so as to enable all sound holes between said receiver arrays to be covered by rotating said ring of arrays to at least a second position, said ultrasound imaging apparatus further comprising means for rotating said ring of arrays to at least a second position.

15. The apparatus of claim 14 further comprising means for vertically displacing said ring of transducer arrays.

16. An ultrasound imaging apparatus as defined in claim 12 further comprising:

means for detecting data from which the refractive index and attenuation coefficient of said object may be determined;

a computer connected to said data detection means, said computer being programmed to (1) determine the refractive index and attenuation coefficient for said object from said data, and (2) correct said reconstructed image of reflection in accordance with the determined refractice index and attenuation coefficient so as to eliminate distortions arising from refraction and attenuation of said transmitted ultrasound signals through said object.

17. The ultrasound imaging apparatus of claim 12 wherein said means for developing said particular type of waveform comprises a waveform generator circuit connected to said transducer arrays for transmitting said ultrasound signals.

18. An ultrasound imaging apparatus as defined in claim 17 wherein said waveform generator circuit comprises:
- a memory circuit for storing a plurality of digital signals, each said digital signal corresponding to a discrete value on said waveform;
- a digital-to-analog (D/A) converter circuit connected to said memory circuit, said D/A converter circuit transforming said digital signals into analog pulses;
- a sample and hold circuit connected to said D/A circuit, said sample and hold circuit holding each analog signal for a selected increment of time;
- a low pass filter circuit connected to said sample and hold circuit for filtering out distortions in said waveform; and
- a counter circuit for generating pulses, said counter circuit being connected to said memory and said sample and hold circuits so as to synchronize said circuits.

19. The apparatus of claim 18 further comprising an analog to digital converter circuit interposed between said transducers for receiving ultrasound signals and said memory circuit for storing said received ultrasound signals.

20. The apparatus of claim 12 wherein said means for developing said particular type of waveform comprises a waveshaping circuit interposed between said transducers for receiving ultrasound signals and said combining means.

21. An ultrasound imaging apparatus as defined in claim 20 wherein said waveshaping circuit comprises:
- an analog-to-digital (A/D) converter circuit for transforming each received ultrasound signal to a plurality of digital signals;
- a digital shift register connected to said A/D converter circuit for storing said digital signals;
- a plurality of multiplier circuits connected to said register;
- a plurality of latching circuits for gating said digital signals through said multiplier circuits, each latching circuit being connected to one of said multiplier circuits;
- a multiplexer circuit connected to said latching circuits, said multiplexer selectively accessing each said latching circuit so as to gate said digital signals through said multiplier circuits; and
- a digital adder circuit connected to said multiplier circuits for summing said digital signals after they have been multiplied, thereby developing a series of digital signals for said received ultrasound signal corresponding to said particular waveform.

22. An ultrasound imaging apparatus as defined in claim 20 wherein said waveshaping circuit comprises:
- an analog-to-digital (A/D) converter circuit for transforming each received ultrasound signal to a plurality of digital signals;
- a digital shift register connected to said A/D converter circuit for storing said digital signals;
- a plurality of multiplying digital-to-analog (D/A) converting circuits connected to said register;
- a plurality of latching circuits for gating said digital signals through said multiplying D/A circuits, each latching circuit being connected to one of said multiplying D/A circuits;
- a multiplexer circuit connected to said latching circuits, said multiplexer selectively accessing each said latching circuit so as to gate said digital signals through said multiplying D/A circuits;
- an analog adder circuit connected to said multiplying A/D circuits for summing said signals gated through said multiplying D/A circuits; and
- an analog-to-digital converter circuit connected to said analog adder circuit for transforming the summation of signals by said analog adder circuit into a series of digital signals corresponding to said particular waveform.

23. An ultrasound imaging apparatus as defined in claim 20 wherein said waveshaping circuit comprises:
- a tapped delay line for receiving said ultrasound signals from said receiver transducers;
- a plurality of variable resistors connected to said tapped delay line;
- an analog adder circuit connected to said resistors for summing each signal received by each resistor from said tapped delay line, thereby developing said particular waveform; and
- an analog-to-digital converter connected to said analog adder for transforming said particular waveform into a series of digital signals.

24. An ultrasound imaging apparatus as defined in claim 20 wherein said waveshaping circuit comprises:
- a tapped delay line for receiving said ultrasound signals from said receiver transducers;
- a plurality of multiplying circuits connected to said tapped delay line;
- a plurality of digital-to-analog (D/A) converter circuits, each D/A circuit being connected to one of said multiplying circuits;
- a plurality of latching circuits, each latching circuit being connected to one of said D/A circuits;
- a multiplexer circuit connected to said latching circuits, said multiplexer selectively accessing each said latching circuit so as to gate a portion of said received ultrasound signal through said multiplying circuit;
- an analog adder circuit connected to said multiplying circuits for summing the signals gated through said multiplying circuits, thereby developing said particular waveform; and
- an analog-to-digital converter connected to said analog adder for transforming said particular waveform into a series of digital signals.

25. A method of reconstructing images of reflection from synthetically focused ultrasound energy comprising the steps of:
- transmitting ultrasound energy signals;
- receiving ultrasound energy signals that have been either reflected by or transmitted through an object being scanned;
- electronically storing said received ultrasound signals;
- developing a particular type of waveform for each said stored signal such that when said stored signals are combined so as to reconstruct therefrom an image of reflection of said object, regions of both constructive and destructive interference will occur, said regions improving the point response of said combined signals so as to enhance the resolution of said reconstructed image of reflection;

electronically combining said stored signals so as to reconstruct therefrom said image of reflection corresponding to said scanned object; and visually displaying said reconstructed image of reflection.

26. The method of claim 25 wherein said step of developing said particular type of waveform comprises the steps of:

periodically generating signals having the shape of said waveform; and transmitting said periodically generated waveforms so that each transmitted ultrasound signal has the shape of said waveform.

27. A method as defined in claim 26 wherein said step of periodically generating said waveform comprises the steps of:

electronically storing a plurality of digital signals, each said digital signal corresponding to a discrete value on said particular waveform;

retrieving from storage each said digital signal;

converting each said retrieved digital signal into a corresponding analog signal; and shaping said analog signals so as to develop therefrom said particular waveform.

28. A method as defined in claim 27 further comprising the step of converting each said received ultrasound signal to a series of corresponding digital signals.

29. A method as defined in claim 25 wherein said step of developing said particular type of waveform comprises the step of transforming each said received ultrasound signal into one or more signals corresponding to said particular type of waveform.

30. The method of claim 29 wherein said transforming step comprises the steps of:

converting each said received ultrasound signal into a series of digital signals;

storing said digital signals;

retrieving each said stored digital signal;

multiplying each said digital signal by a predetermined value corresponding to a discrete value on said waveform; and electronically summing each said retrieved and multiplied digital signal so as to develop therefrom a series of digital signals corresponding to said particular waveform.

31. The method of claim 29 wherein said transforming step comprises the steps of:

converting each said received signal into a series of digital signals;

storing said digital signals;

retrieving each said stored digital signal;

multiplying said retrieved digital signals by a predetermined value corresponding to a discrete value on said waveform;

converting said multiplied digital signals back to analog signals;

electronically summing said analog signals so as to develop therefrom said particular waveform; and converting said particular waveform to a series of corresponding digital signals.

32. The method of claim 29 wherein said transforming step comprises the steps of:

imposing a series of time delays on each said received ultrasound signal;

selectively accessing portions of the received ultrasound signal during each said time delay;

multiplying each accessed portion of the received ultrasound signal by a predetermined value corresponding to a discrete value on said particular waveform;

electronically summing said multiplied portions of the received ultrasound signal so as to develop therefrom said particular waveform; and converting said waveform to a series of corresponding digital signals.

33. A method as defined in claim 25 further comprising the steps of:

detecting the transmission data from which the refractive index and attenuation coefficient for said object may be determined;

determining the refractive index and the attenuation coefficient for said object; and electronically adjusting said reconstructed image of reflection in accordance with said determined refractive index and attenuation index so as to eliminate distortions arising from refraction and attenuation of ultrasound energy through said object, thereby enhancing the resolution for said reconstructed image.

34. The method defined in claim 25 wherein said transmitting step comprises the steps of:

encircling said object with a plurality of transmitter and receiver transducer arrays;

propagating semicircular wavefronts of ultrasound energy at different points around said object by sequentially triggering a plurality of said transmitter arrays; and commutating said transmitter arrays to permit transmission of ultrasound energy waves at each point around said object.

35. In an improved ultrasound imaging apparatus for reconstructing images of reflection from synthetically focused ultrasound energy, the improvement comprising:

a plurality of transmitter and receiver transducer arrays for transmitting and receiving ultrasound energy signals, said receiver arrays comprising one or more receiver arrays having a first length and one or more receiver arrays having a second length different from said first length so as to enable all sound holes caused by the transmitter arrays located between said receiver arrays to be covered by moving said receiver arrays to at least a second position, said ultrasound imaging apparatus further comprising means for moving said receiver arrays to at least said second position.

36. An improved ultrasound imaging apparatus as defined in claim 35 wherein said transmitter and receiver arrays are connected so as to encircle the object to be scanned, and wherein said receiver arrays comprise one or more arrays having a first arcuate length and one or more arrays having a second arcuate length different from said first length so as to enable all sound holes between said receiver arrays to be covered by rotating said ring of arrays to at least a second position, said ultrasound imaging apparatus further comprising means for rotating said ring of arrays to at least a second position, means for sequentially triggering said transmitter arrays so as to propagate a series of ultrasound signals through said object, and means, connected to said transducer arrays, for commutating said transmitter arrays so as to transmit said ultrasound signals from each possible position around said object.

37. An improved ultrasound imaging apparatus as defined in claim 36 further comprising means for vertically displacing said transducer arrays.

38. An ultrasound imaging apparatus for reconstructing images of reflection from synthetically focused ultrasound energy, said apparatus comprising:
    means for transmitting ultrasound energy signals;
    means for receiving ultrasound energy signals that have been either reflected by or transmitted through an object being scanned by said apparatus;
    means, electronically connected to said receiving means, for electronically storing said received ultrasound signals;
    means, electronically connected to said receiving means, for detecting transmission data from which the refractive index and attenuation coefficient for said object may be determined;
    means, electronically connected to said storage means, for combining said stored signals so as to reconstruct therefrom an image of reflection corresponding to said scanned object;
    means, electronically connected to said detecting means, for determining the refractive index and attenuation coefficient for each point in said object;
    means for correcting each corresponding point of said reconstructed image of reflection in accordance with the determined point-dependant refractive index and attenuation coefficient for said object so as to eliminate distortions arising from refraction and attenuation of ultrasound energy through said object, thereby enhancing the resolution for said reconstructed image of reflection; and
    means for visually displaying said reconstructed image of reflection.

39. An ultrasound imaging apparatus as defined in claim 38 further comprising means for developing a particular type of waveform for each said stored signal such that when said stored signals are combined so as to reconstruct therefrom an image of reflection, regions of both constructive and destructive interference will occur, said regions improving the point response of said combined signals so as to enhance the resolution of said reconstructed image of reflection.

40. An improved method of reconstructing images of reflection from synthetically focused ultrasound energy comprising the steps of:
    transmitting ultrasound energy signals;
    receiving ultrasound energy signals that have been either reflected by or transmitted through an object being scanned;
    electronically storing said receiver ultrasound signals;
    detecting transmission data from which the refractive index and attenuation coefficient for said object may be determined;
    determining the refractive index and attenuation coefficient for each point in said object;
    electronically combing said stored signals so as to reconstruct therefrom an image of reflection corresponding to said scanned object;
    correcting each corresponding point of said reconstructed image of reflection in accordance with the determined point-dependant refractive index and attenuation coefficient for said object so as to eliminate distortions in said reconstructed image arising from refraction and attenuation of ultrasound energy through said object, thereby enhancing the resolution for said reconstructed image; and visually displaying said corrected reconstructed image of reflection.

41. A method as defined in claim 40 further comprising the step of developing a particular type of waveform for each said stored signal such that when said stored signals are combined so as to reconstruct therefrom an image of reflection, regions of both constructive and destructive interference will occur, said regions improving the point response of said combined signals so as to enhance the resolution of said reconstructed image of reflection.

* * * * *